(12) United States Patent
Woodard et al.

(10) Patent No.: US 11,078,257 B2
(45) Date of Patent: Aug. 3, 2021

(54) RECOMBINANT GRAM NEGATIVE BACTERIA AND METHODS OF GENERATING AND UTILIZING SAME

(71) Applicant: The Regents of the University of Michigan, Ann Arbor, MI (US)

(72) Inventors: Ronald W. Woodard, Ann Arbor, MI (US); Andrew Pratt, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 16/321,093

(22) PCT Filed: Jul. 28, 2017

(86) PCT No.: PCT/US2017/044382
§ 371 (c)(1),
(2) Date: Jan. 28, 2019

(87) PCT Pub. No.: WO2018/023000
PCT Pub. Date: Feb. 1, 2018

(65) Prior Publication Data
US 2020/0002408 A1 Jan. 2, 2020

Related U.S. Application Data

(60) Provisional application No. 62/368,451, filed on Jul. 29, 2016.

(51) Int. Cl.
| | |
|---|---|
| *A61K 39/108* | (2006.01) |
| *A61K 35/74* | (2015.01) |
| *A61K 39/05* | (2006.01) |
| *A61K 39/095* | (2006.01) |
| *A61K 39/118* | (2006.01) |
| *A61K 39/02* | (2006.01) |
| *A61K 39/102* | (2006.01) |
| *A61K 39/106* | (2006.01) |
| *C07K 16/12* | (2006.01) |
| *C07K 14/22* | (2006.01) |
| *C12R 1/19* | (2006.01) |
| *C12N 9/10* | (2006.01) |
| *C12R 1/15* | (2006.01) |

(52) U.S. Cl.
CPC .......... *C07K 16/1232* (2013.01); *A61K 35/74* (2013.01); *A61K 39/0258* (2013.01); *A61K 39/05* (2013.01); *A61K 39/095* (2013.01); *A61K 39/102* (2013.01); *A61K 39/105* (2013.01); *A61K 39/118* (2013.01); *C07K 14/22* (2013.01); *C12R 1/19* (2013.01); *A61K 2039/106* (2013.01); *C12N 9/1048* (2013.01); *C12R 1/15* (2013.01)

(58) Field of Classification Search
None
See application file for complete search history.

(56) References Cited

U.S. PATENT DOCUMENTS

| 6,558,677 B2 | 5/2003 | Zollinger |
| 2005/0013831 A1 | 1/2005 | Foster |
| 2010/0272758 A1 | 10/2010 | Woodard et al. |
| 2010/0291153 A1 | 11/2010 | Geurtsen et al. |
| 2014/0286996 A1 | 9/2014 | Gorvel et al. |

OTHER PUBLICATIONS

Moeller et al. Infect. Immun. 71: 2142-2152, 2003.*
Reynolds et al. Biochemistry 48: 9627-9640, 2009.*
Pitcher DG. In: E. Christophers et al. (Eds) XXXII. Tagung gehalten in Westerland/Sylt vom 16. bis 20. Sep. 1980, Springer-Verlag Berlin Heidelberg 1981, pp. 273-275.*
Belunis et al., Inhibition of lipopolysaccharide biosynthesis and cell growth following inactivation of the kdtA gene in *Escherichia coli*. J Biol Chem. Nov. 17, 1995;270(46):27646-52.
Brabetz et al., Comparative analyses of secondary gene products . . . (2000) Eur J Biochem 267, 5458-5465.
Brabetz et al., 3-Deoxy-D-manno-oct-2-ulosonic Acid (Kdo) Transferase (WaaA) and Kdo Kinase (KdkA) of Haemophilus influenzae Are Both Required to Complement a waaA Knockout Mutation of *Escherichia coli*. (2000) J. Biol. Chem. 275, 34954-34962.
Chatfield, et al., Construction of a genetically defined *Salmonella typhi* Ty2 aroA, aroC mutant for the engineering of a candidate oral typhoid-tetanus vaccine. Vaccine. 1992;10(1):53-60.
Cullen et al., EptC of Campylobacter jejuni Mediates Phenotypes Involved in Host Interactions and Virulence. (2013) Infect Immun 81, 430-440.
Czyzyk et al., Lipopolysaccharide Biosynthesis without the Lipids: Recognition Promiscuity of *Escherichia coli* Heptosyltransferase I. (2011) Biochemistry 50, 10570-10572.
Datsenko and Wanner One-step inactivation of chromosomal genes in *Escherichia coli* K-12 using PCR products. (2000), PNAS 97, 6640-6645.

(Continued)

*Primary Examiner* — Sarvamangala Devi
(74) *Attorney, Agent, or Firm* — Casimir Jones, S.C.; Tanya A. Arenson

(57) ABSTRACT

The present invention provides novel, recombinant Gram-negative bacteria. In particular, the invention provides recombinant Gram-negative bacteria (e.g., *E. coli*) lacking genes involved in lipopolysaccharide (LPS, endotoxin) biosynthesis (e.g., lacking genes required for core oligosaccharide biosynthesis) and also provides recombinant Gram-negative bacteria lacking genes involved in LPS biosynthesis that contain one or more exogenous KDO transferases and/or one or more exogenous heptosyltransferases (e.g., from one or more types and/or strains of bacteria). The invention further provides methods of generating and utilizing (e.g., as or in an immunogenic composition (e.g., as or in an adjuvant and/or vaccine)) the recombinant Gram-negative bacteria therapeutic, preventative, and/or research applications.

13 Claims, 26 Drawing Sheets

Specification includes a Sequence Listing.

(56) References Cited

OTHER PUBLICATIONS

Galanos et al., A new method for the extraction of R lipopolysaccharides. (1969) Eur J Biochem 9(2), 245-249.
Garrett, et al., Accumulation of a Lipid A Precursor Lacking the 4'-Phosphate following Inactivation of the *Escherichia coli* lpxKGene. 1998, J. Biol. Chem., 273:12457-12465.
Gorfinkiel, et al., Sequence and regulation of the uapA gene encoding a uric acid-xanthine permease in the fungus *Aspergillus nidulans*. J Biol Chem. Nov. 5, 1993;268(31):23376-81.
Grizot et al., Structure of the *Escherichia coli* heptosyltransferase WaaC: binary complexes with ADP and ADP-2-deoxy-2-fluoro heptose. J Mol Biol. Oct. 20, 2006;363(2):383-94.
Gronow et al., Kdo-(2→8)-Kdo-(2→4)-Kdo but not Kdo-(2→4)-Kdo-(2→4)-Kdo is an acceptor for transfer of L-glycero-α-D-manno-heptose by *Escherichia coli* heptosyltransferase I (WaaC). (2009) Innate Immun 15, 13-23.
Harborne, et al., Transcriptional control, translation and function of the products of the five open reading frames of the *Escherichia coli* nir operon. Mol Microbiol. Oct. 1992;6(19):2805-13.
Heine et al., Endotoxic activity and chemical structure of lipopolysaccharides from Chlamydia trachomatis serotypes E and L2 and Chlamydophila psittaci 6BC. (2003) European Journal of Biochemistry 270, 440-450.
Heinrichs, D. et al. Molecular basis for structural diversity in the core regions of the lipopolysaccharides of *Escherichia coli* and *Salmonella enterica*, Molecular Microbiology, 1998 30(2), 221-232.
Hobman et al., Laboratory strains of *Escherichia coli*: model citizens or deceitful delinquents growing old disgracefully? (2007) Molecular Microbiology 64(4), 881-885.
Hone, et al., Construction of defined galE mutants of *Salmonella* for use as vaccines. 1987, J. Infect. Dis., 156:167-74.
Hone, et al., Construction of genetically defined double aro mutants of Salmonella typhi. 1991, Vaccine, 9:810-816.
International Search Report and Written Opinion, International Patent Application No. PCT/US2017/044382, dated Oct. 6, 2017, 16 pages.
Janeway and Medzhitov, Innate immune recognition. (2002) Annu. Rev. Immunol. 20, 197-216.
Kohler and Milstein Continuous cultures of fused cells secreting antibody of predefined specificity. 1975 Nature 256; 495-497.
Lee, et al., Mutation of the htrB locus of Haemophilus influenzae nontypable strain 2019 is associated with modifications of lipid A and phosphorylation of the lipo-oligosaccharide. J Biol Chem. Nov. 10, 1995;270(45):27151-9.
Liu, *Escherichia coli* K12 regains its O antigen. (1994) Microbiology 140, 49-57.
Loutet, SA et al. A Complete Lipopolysaccharide Inner Core Oligosaccharide Is Required for Resistance . . . Journal of Bacteriology, Mar. 2006, p. 2073-2080.
Mamat et al., Single amino acid substitutions in either YhjD or MsbA confer viability to 3-deoxy-d-manno-oct-2-ulosonic acid-depleted *Escherichia coli*. (2008) Molecular Microbiology 67, 633-648.
Mamat et al., WaaA of the hyperthermophilic bacterium *Aquifex aeolicus* is a monofunctional 3-deoxy-D-manno-oct-2-ulosonic acid transferase involved in lipopolysaccharide biosynthesis. J Biol Chem. Aug. 14, 2009;284(33):22248-62.
Meredith et al., Modification of lipopolysaccharide with colanic acid (M-antigen) repeats in *Escherichia coli*. J Biol Chem. Mar. 16, 2007;282(11):7790-8.
Meredith et al., Redefining the Requisite Lipopolysaccharide Structure in *Escherichia coli*. (2006) ACS chemical biology 1, 33-42.
Naito et al., Effects of Sequential Campylobacter jejuni 81-176 . . . (2010) J. Bacteriol. 192, 2182-2192.
Noah et al., Cloning, sequencing, and functional analysis of three glycosyltransferases involved in the biosynthesis of the inner core region of Klebsiella pneumoniae lipopolysaccharide. J Endotoxin Res. 2001;7(1):25-33.
Noriega, et al, Construction and characterization of attenuated delta aroA delta virG Shigella flexneri 2a strain CVD 1203, a prototype live oral vaccine. 1994, Infect. Immun., 62:5168-5172.
Odegaard, et al., Shortened hydroxyacyl chains on lipid A of *Escherichia coli* cells expressing a foreign UDP-N-acetylglucosamine O-acyltransferase. J Biol Chem. Aug. 8, 1997;272(32):19688-96.
Ozinsky et al., The repertoire for pattern recognition of pathogens by the innate immune system is defined by cooperation between Toll-like receptors. PNAS Dec. 5, 2000 97 (25) 13766-13771.
Pickard, et al., Characterization of defined ompR mutants of *Salmonella typhi*: ompR is involved in the regulation of Vi polysaccharide expression. 1994, Infect. Immun., 62:3984-3993.
Plotz et al., Characterization of a Novel Lipid A ContainingD-Galacturonic Acid That Replaces Phosphate Residues (2000) J. Biol. Chem. 275, 11222-11228.
Raetz and Whitfield, Lipopolysaccharide Endotoxins, (2002) Ann Rev of Biochem 71, 635-700.
Roncero and Casadaban, Genetic analysis of the genes involved in synthesis of the lipopolysaccharide core in *Escherichia coli* K-12: three operons in the rfa locus. (1992) J. Bacteriol. 174, 3250-3260.
Rund, et al. Structural analysis of the lipopolysaccharide from Chlamydophila psittaci strain 6BC. Eur J Biochem. Sep. 2000;267(18):5717-26.
Sambrook, J., and Russell, D. W. (2001) Molecular Cloning: A Laboratory Manual, 3rd Edition, Cold Spring Harbor Laboratory Press, Cold Spring Harbor, NY, Book, Table of Contents Only.
Schmidt et al., Immunochemistry of R Lipopolysaccharides of *Escherichia coli*. (1970) Eur J Biochem 16, 382-392.
Stauffer, Characterization of the gcv control region from *Escherichia coli*. et al., 1994, J. Bact, 176:6159-64.
Stead et al., A Novel 3-Deoxy-d-manno-Octulosonic Acid (Kdo) Hydrolase That Removes the Outer Kdo Sugar of Helicobacter pylori Lipopolysaccharide. (2005), J. Bacteriol. 187, 3374-3383.
Vaughan T J et al Human antibodies by design. 1998 Nature Biotechnology 16; 535-539.
Wang, Z et al. Influence of Core Oligosaccharide of Lipopolysaccharide to Outer Membrane Behavior of *Escherichia coli*, Mar. Drugs 2015, 13, 3325-3339.
Zahringer, et al., Structural and biological characterisation of a novel tetra-acyl lipid A from *Escherichia coli* F515 lipopolysaccharide acting as endotoxin antagonist in human monocytes. J Endotoxin Res. 2001;7(2):133-46.

\* cited by examiner

FIG. 3

| Kdo transferase | Kdo-Lipid IV$_A$ | Kdo$_2$-Lipid A | Kdo$_3$-Lipid A |
|---|---|---|---|
| HiWaaA | + | - | - |
| EcWaaA | + | + | + |
| CtWaaA | + | + | + |
| CpWaaA | + | + | + |

FIG. 4

| Heptosyltransferase | Hep-Kdo-Lipid IV$_A$ | Hep-Kdo$_2$-Lipid A | Hep-Kdo$_3$-Lipid A |
|---|---|---|---|
| HpWaaC | + | + | - |
| EcWaaC | + | + | + |
| CjWaaC | - | + | - |
| AaRfaC1 | + | - | - |

FIG. 6A

| Strain, plasmid, or primer | Description | Source |
|---|---|---|
| KPM56 | E. coli K-12 MG1655 F⁻ rph⁺ fnr⁺ ΔgutQ ΔkdsD yhjD400 kdsD⁻ ΔwaaC ΔwaaA | Mamat et al., (2009) J Biol Chem *284*, 22248-22262 |
| WOD01 | KPM50 Δ(waaF-waaA)::kan | This disclosure |
| WOD02 | KPM50 Δ(waaF-waaA) | This disclosure |
| WOD03 | WOD 02 + pETduet1 (empty vector) | This disclosure |
| WOD04 | WOD 02 + pHiA (carrying *H. influenzae* waaA gene) | This disclosure |
| WOD05 | WOD 02 + pEcA (carrying *E. coli* waaA gene) | This disclosure |
| WOD06 | WOD 02 + pCtA (carrying *C. thracomatis* waaA gene) | This disclosure |
| WOD07 | WOD 02 + pCpA (carrying *C. psittaci* waaA gene) | This disclosure |
| WOD08 | WOD 02 + pHpC (carrying *H.pylori* waaC gene) | This disclosure |
| WOD09 | WOD 02 + pEcC (carrying *E. coli* waaC gene) | This disclosure |
| WOD10 | WOD 02 + pCjC (carrying *C. jejuni* waaC gene) | This disclosure |
| WOD11 | WOD 02 + pAaC (carrying *A. aeolicus* rfaC1 gene) | This disclosure |
| WOD12 | WOD 02 + pHiAHpC (carrying *H. influenzae* waaA and *H. pylori* waaC gene) | This disclosure |
| WOD13 | WOD 02 + pHiAEcC (carrying *H. influenzae* waaA and *E.coli* waaC gene) | This disclosure |
| WOD14 | WOD 02 + pHiACjC (carrying *H. influenzae* waaA and *C. jejuni* waaC gene) | This disclosure |
| WOD15 | WOD 02 + pHiAAaC (carrying *H. influenzae* waaA and *A. aeolicus* rfaC1 gene) | This disclosure |
| WOD16 | WOD 02 + pEcAHpC (carrying *E. coli* waaA and *H. pylori* waaC gene) | This disclosure |
| WOD17 | WOD 02 + pEcAEcC (carrying *E. coli* waaA and *E. coli* waaC gene) | This disclosure |
| WOD18 | WOD 02 + pEcACjC (carrying *E. coli* waaA and *C. jejuni* waaC gene) | This disclosure |
| WOD19 | WOD 02 + pEcAAaC (carrying *E. coli* waaA and *A. aeolicus* rfaC1 gene) | This disclosure |
| WOD20 | WOD 02 + pCtAHpC (carrying *C. thracomatis* waaA and *H. pylori* waaC gene) | This disclosure |
| WOD21 | WOD 02 + pCtAEcC (carrying *C. thracomatis* waaA and *E. coli* waaC gene) | This disclosure |
| WOD22 | WOD 02 + pCtACjC (carrying *C. thracomatis* waaA and *C. jejuni* waaC gene) | This disclosure |
| WOD23 | WOD 02 + pCtAAaC (carrying *C. thracomatis* waaA and *A. aeolicus* rfaC1 gene) | This disclosure |
| WOD24 | WOD 02 + pCpAHpC (carrying *C. psittaci* waaA and *H. pylori* waaC gene) | This disclosure |
| WOD25 | WOD 02 + pCpAEcC (carrying *C. psittaci* waaA and *E. coli* waaC gene) | This disclosure |
| WOD26 | WOD 02 + pCpACjC (carrying *C. psittaci* waaA and *C. jejuni* waaC gene) | This disclosure |
| WOD27 | WOD 02 + pCpAAaC (carrying *C. psittaci* waaA and *A. aeolicus* rfaC1 gene) | This disclosure |
| pET26b | Kan$^R$, T7 expression vector | Novagen |
| p26HpC | *Helicobacter pylori* J99 waaC inserted into NdeI/BamHI sites of pET26b | This disclosure |
| p26EcC | *E. coli* K-12 waaC inserted into NdeI/BamHI sites of pET26b | This disclosure |
| p26CjC | *Campylobacter jejuni* NCTC 11168 waaC inserted into NdeI/BamHI sites of pET26b | This disclosure |
| p26AaC | *Aquifex aeolicus* rfaC1 inserted into NdeI/BamHI sites of pET26b | This disclosure |
| pUM211 | pET16b containing the waaA gene from *H. influenzae* I69 | Mamat et al., (2009) J Biol Chem *284*, 22248-22262 |
| pUM212 | pET16b containing the waaA gene from *E. coli* K-12 | Mamat et al., (2009) J Biol Chem *284*, 22248-22262 |
| pFEN207 | Amp$^R$; pUC8 plasmid containing the waaA gene from *C. trachomatis* L2 | Nano (1985), Science 228, 742-744 |
| pUM210 | pET16b containing the waaA gene from *C. psittaci* 6BC | Mamat et al., (2009) J Biol Chem *284*, 22248-22262 |

FIG. 6B

| | | |
|---|---|---|
| pETduet1 | Amp^R; T7 expression vector for dual gene expression | Novagen |
| pHiA | *Haemophilus influenzae* 169 *waaA* inserted into NdeI/XhoI of pETduet1 | This disclosure |
| pEcA | *E. coli* K-12 *waaA* inserted into NdeI/XhoI of pETduet1 | This disclosure |
| pCtA | *Chlamydia trachomatis* L2 *waaA* inserted into NdeI/XhoI of pETduet1 | This disclosure |
| pCpA | *Chlamydophila psittaci* 6BC *waaA* inserted into NdeI/XhoI of pETduet1 | This disclosure |
| pHpC | *H. pylori* J99 *waaC* inserted into XbaI/BamHI sites of pETduet1 | This disclosure |
| pEcC | *E. coli* K-12 *waaC* inserted into XbaI/BamHI sites of pETduet1 | This disclosure |
| pCjC | *C. jejuni* NCTC 11168 *waaC* inserted into XbaI/BamHI sites of pETduet1 | This disclosure |
| pAaC | *A. aeolicus rfaC1* inserted into XbaI/BamHI sites of pETduet1 | This disclosure |
| pHiAHpC | *H. influenzae* 169 *waaA* inserted into NdeI/XhoI and *H. pylori* J99 *waaC* inserted into XbaI/BamHI sites of pETduet1 | This disclosure |
| pHiAEcC | *H. influenzae* 169 *waaA* inserted into NdeI/XhoI and *E. coli* K-12 *waaC* inserted into XbaI/BamHI sites of pETduet1 | This disclosure |
| pHiACjC | *H. influenzae* 169 *waaA* inserted into NdeI/XhoI and *C. jejuni* NCTC 11168 *waaC* inserted into XbaI/BamHI sites of pETduet1 | This disclosure |
| pHiAAaC | *H. influenzae* 169 *waaA* inserted into NdeI/XhoI and *A. aeolicus rfaC1* inserted into XbaI/BamHI sites of pETduet1 | This disclosure |
| pEcAHpC | *E. coli* K-12 *waaA* inserted into NdeI/XhoI and *H. pylori* J99 *waaC* inserted into XbaI/BamHI sites of pETduet1 | This disclosure |
| pEcAEcC | *E. coli* K-12 *waaA* inserted into NdeI/XhoI and *E. coli* K-12 *waaC* inserted into XbaI/BamHI sites of pETduet1 | This disclosure |
| pEcACjC | *E. coli* K-12 *waaA* inserted into NdeI/XhoI and *C. jejuni* NCTC 11168 *waaC* inserted into XbaI/BamHI sites of pETduet1 | This disclosure |
| pEcAAaC | *E. coli* K-12 *waaA* inserted into NdeI/XhoI and *A. aeolicus rfaC1* inserted into XbaI/BamHI sites of pETduet1 | This disclosure |
| pCtAHpC | *C. trachomatis* L2 *waaA* inserted into NdeI/XhoI and *H. pylori* J99 *waaC* inserted into XbaI/BamHI sites of pETduet1 | This disclosure |
| pCtAEcC | *C. trachomatis* L2 *waaA* inserted into NdeI/XhoI and *E. coli* K-12 *waaC* inserted into XbaI/BamHI sites of pETduet1 | This disclosure |
| pCtACjC | *C. trachomatis* L2 *waaA* inserted into NdeI/XhoI and *C. jejuni* NCTC 11168 *waaC* inserted into XbaI/BamHI sites of pETduet1 | This disclosure |
| pCtAAaC | *C. trachomatis* L2 *waaA* inserted into NdeI/XhoI and *A. aeolicus rfaC1* inserted into XbaI/BamHI sites of pETduet1 | This disclosure |
| pCpAHpC | *C. psittaci* 6BC *waaA* inserted into NdeI/XhoI and *H. pylori* J99 *waaC* inserted into XbaI/BamHI sites of pETduet1 | This disclosure |
| pCpAEcC | *C. psittaci* 6BC *waaA* inserted into NdeI/XhoI and *E. coli* K-12 *waaC* inserted into XbaI/BamHI sites of pETduet1 | This disclosure |
| pCpACjC | *C. psittaci* 6BC *waaA* inserted into NdeI/XhoI and *C. jejuni* NCTC 11168 *waaC* inserted into XbaI/BamHI sites of pETduet1 | This disclosure |
| pCpAAaC | *C. psittaci* 6BC *waaA* inserted into NdeI/XhoI and *A. aeolicus rfaC1* inserted into XbaI/BamHI sites of pETduet1 | This disclosure |
| pKD46 | Amp^R; λ Red recombinase expression plasmid | Datsenko (2000) PNAS 97, 6640-6645 |
| pKD4 | Amp^R, Kan^R; template plasmid for kanamycin resistance cassette | Datsenko (2000) PNAS 97, 6640-6645 |
| pCP20 | Amp^R, Cm^R; FLP recombinase expression plasmid | Datsenko (2000) PNAS 97, 6640-6645 |
| HpWaaCfor | gattctagaattcatATGAAAATAGCGATTGTCAGGCTTTCAG (SEQ ID NO.:1) | This disclosure |
| HpWaaCrev | gaattcggatccTCATTCTTTTTCCTTTAAAACGTTTAAAACGC (SEQ ID NO.:2) | This disclosure |
| EcWaaCfor | gattctagaattcatATGCGGGTTTTGATCGTTAAAAC (SEQ ID NO.:3) | This disclosure |
| EcWaaCrev | gaattcggatccTTATAATGATGATAACTTTTCCAAAACTGC (SEQ ID NO.:4) | This disclosure |
| CjWaaCfor | tatacatATGATCTTTTTTATTATTTTTAACTTGGACGGC (SEQ ID NO.:5) | This disclosure |
| CjWaaCrev | atatggatccTTATAAGCTTTTTCTTGCATCAATTCCC (SEQ ID NO.:6) | This disclosure |
| AaRfaC1for | gattctagaattcatATGAAGAAGGCGTTAATAGTGAGG (SEQ ID NO.:7) | This disclosure |
| AaRfaC1rev | gaattcggatccTTACGGCTTGGTATTCAAAATGTTTATAG (SEQ ID NO.:8) | This disclosure |

FIG. 6C

| HiWaaAfor | atatatatcatATGTGGCGTTTTTTTTATACCAGCT (SEQ ID NO.:9) | This disclosure |
|---|---|---|
| HiWaaArev | atatctcgagTCATACATTGCGCTCCAAATAAGG (SEQ ID NO.:10) | This disclosure |
| EcWaaAfor | actccatATGCTCGAATTGCTTTACACCG (SEQ ID NO.:11) | This disclosure |
| EcWaaArev | cagtctcgagTCAATGCGTTTTCGGTGGC (SEQ ID NO.:12) | This disclosure |
| CtWaaAfor | gattctagaattcatATGATAAGACGTTGGTTAACATCTCG (SEQ ID NO.:13) | This disclosure |
| CtWaaArev | gaattcctcgagTTAGATTTTCATGCAAGTAATTTGGCTC (SEQ ID NO.:14) | This disclosure |
| CpWaaAfor | actgcatATGGTGGGGCTTCCTAGGATT (SEQ ID NO.:15) | This disclosure |
| CpWaaArev | cactctcgagCTATATTTTTACACAAGGGATATATCTTTTAAAAG (SEQ ID NO.:16) | This disclosure |
| WaaFKOfor | GTGTAACGGAATACATGGCCTGGCTGAATCGCGACGCATAAGAGCTCTGCgtgtaggctggagctgcttc (SEQ ID NO.:17) | This disclosure |
| WaaAKOrev | TAATGGGATCGAAAGTACCCGGATAAATCGCCCGTTTTTGCATAACAACCcatatgaatatcctccttag (SEQ ID NO.:18) | This disclosure |
| WaaFKOforseq | CCGTTCAAAACCGTTGCTGAAG (SEQ ID NO.:19) | This disclosure |
| WaaAKOrevseq | CGC GTC ACG ATA TCG ATA TGA CC (SEQ ID NO.:20) | This disclosure |

FIG. 7

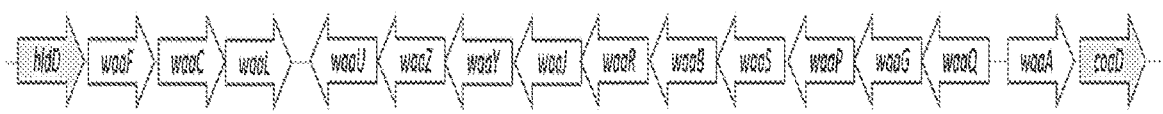

FIG. 8A

| Obs Mass | Calc Mass | Chemical Composition |
|---|---|---|
| 1178.66 | 1178.661 | 2*GlcN, 2*P, 3*(OH)-14:0 |
| 1404.85 | 1404.854 | 2*GlcN, 2*P, 4*(OH)-14:0 |
| 1484.82 | 1484.820 | 2*GlcN, 3*P, 4*(OH)-14:0 |
| 1527.56 | 1527.863 | 2*GlcN, 2*P, 4*(OH)-14:0, 1*P-EtN |
| 1624.91 | 1624.912 | 2*GlcN, 2*P, 4*(OH)-14:0, 1*Kdo |
| 1747.92 | 1747.920 | 2*GlcN, 2*P, 4*(OH)-14:0, 1*Kdo, 1*P-EtN |
| 1766.09 | 1766.092 | 2*GlcN, 2*P, 4*(OH)-14:0, 1*16:0 |
| 1800.94 | 1800.944 | 2*GlcN, 2*P, 3*(OH)-14:0, 1*12:0, 2*Kdo |
| 1816.98 | 1816.976 | 2*GlcN, 2*P, 4*(OH)-14:0, 1*Kdo, 1*Hep |
| 1835.11 | 1835.111 | 2*GlcN, 2*P, 4*(OH)-14:0, 1*14:0, 1*Kdo |
| 1844.97 | 1844.971 | 2*GlcN, 2*P, 4*(OH)-14:0, 2*Kdo |
| 1881.91 | 1880.911 | 2*GlcN, 3*P, 3*(OH)-14:0, 1*12:0, 2*Kdo |
| 1994.01 | 1993.008 | 2*GlcN, 2*P, 3*(OH)-14:0, 1*12:0, 2*Kdo, 1*Hep |
| 2000.15 | 1999.142 | 2*GlcN, 2*P, 4*(OH)-14:0, 1*12:0, 1*Kdo, 1*Hep |
| 2018.28 | 2017.278 | 2*GlcN, 2*P, 4*(OH)-14:0, 1*14:0, 1*12:0, 1*Kdo |
| 2028.14 | 2027.137 | 2*GlcN, 2*P, 4*(OH)-14:0, 1*12:0, 2*Kdo |
| 2073.98 | 2072.974 | 2*GlcN, 3*P, 3*(OH)-14:0, 1*12:0, 2*Kdo, 1*Hep |
| 2108.11 | 2107.104 | 2*GlcN, 3*P, 4*(OH)-14:0, 1*12:0, 2*Kdo |

FIG. 8B

| | | |
|---|---|---|
| 2141.29 | 2140.286 | 2*GlcN, 2*P, 4*(OH)-14:0, 1*14:0, 1*12:0, 1*Kdo, 1*Hep |
| 2220.21 | 2219.201 | 2*GlcN, 2*P, 4*(OH)-14:0, 1*12:0, 1*Kdo, 1*Hep |
| 2238.34 | 2237.336 | 2*GlcN, 2*P, 4*(OH)-14:0, 1*14:0, 1*12:0, 2*Kdo |
| 2248.20 | 2247.196 | 2*GlcN, 2*P, 4*(OH)-14:0, 1*12:0, 3*Kdo |
| 2300.17 | 2299.167 | 2*GlcN, 3*P, 4*(OH)-14:0, 1*12:0, 1*Kdo, 1*Hep |
| 2318.31 | 2317.302 | 2*GlcN, 3*P, 4*(OH)-14:0, 1*14:0, 1*12:0, 2*Kdo |
| 2328.17 | 2327.162 | 2*GlcN, 3*P, 4*(OH)-14:0, 1*12:0, 3*Kdo |
| 2429.89 | 2429.89 | ECA |
| 2430.40 | 2429.399 | 2*GlcN, 2*P, 4*(OH)-14:0, 1*14:0, 1*12:0, 2*Kdo, 1*Hep |
| 2458.40 | 2457.394 | 2*GlcN, 2*P, 4*(OH)-14:0, 1*14:0, 1*12:0, 3*Kdo |
| 2510.37 | 2509.366 | 2*GlcN, 3*P, 4*(OH)-14:0, 1*14:0, 1*12:0, 2*Kdo, 1*Hep |
| 2538.36 | 2537.360 | 2*GlcN, 3*P, 4*(OH)-14:0, 1*14:0, 1*12:0, 3*Kdo |
| 2650.46 | 2649.458 | 2*GlcN, 2*P, 4*(OH)-14:0, 1*14:0, 1*12:0, 3*Kdo, 1*Hep |

FIG. 9A
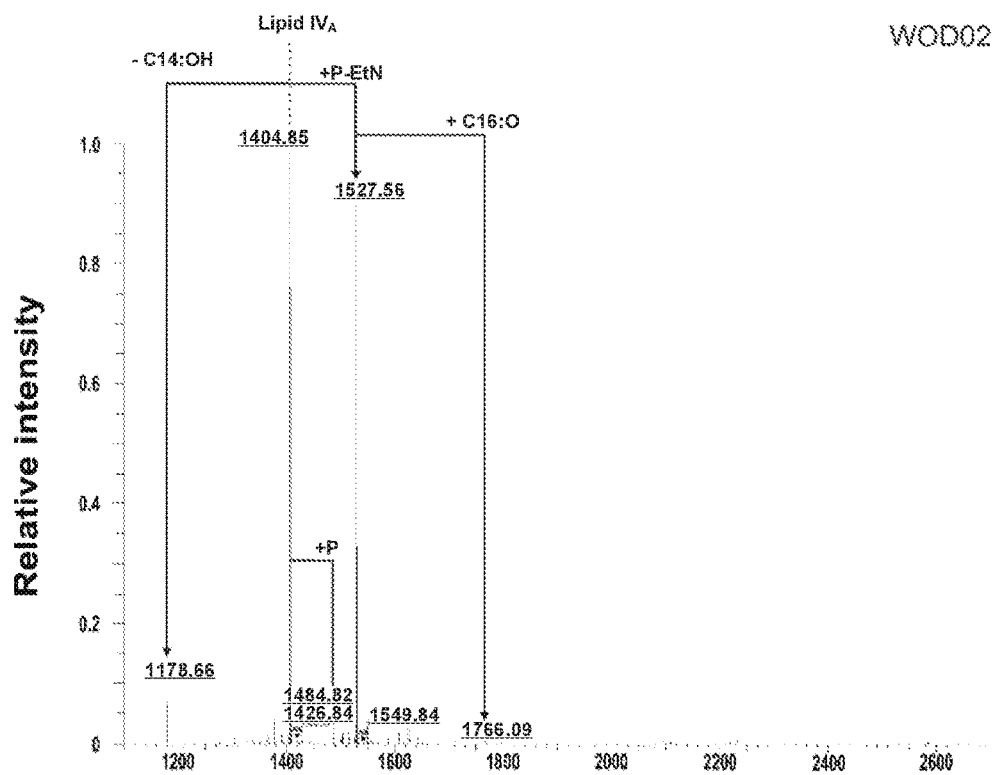
Mass spectrum of WOD02 with mass units of m/z.
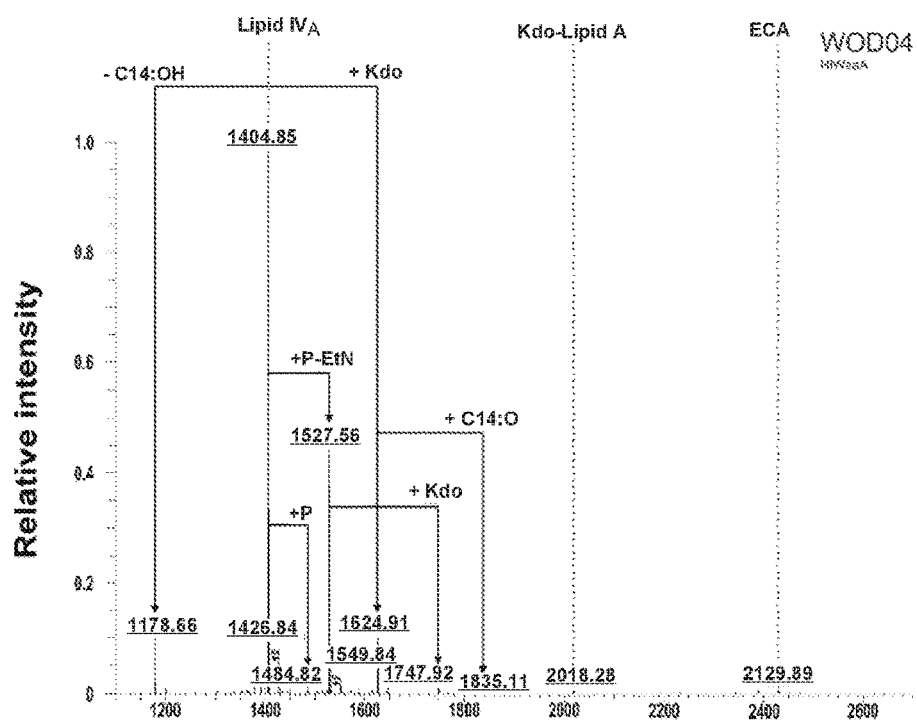
Mass spectrum of WOD04 with mass units of m/z.

FIG. 9B
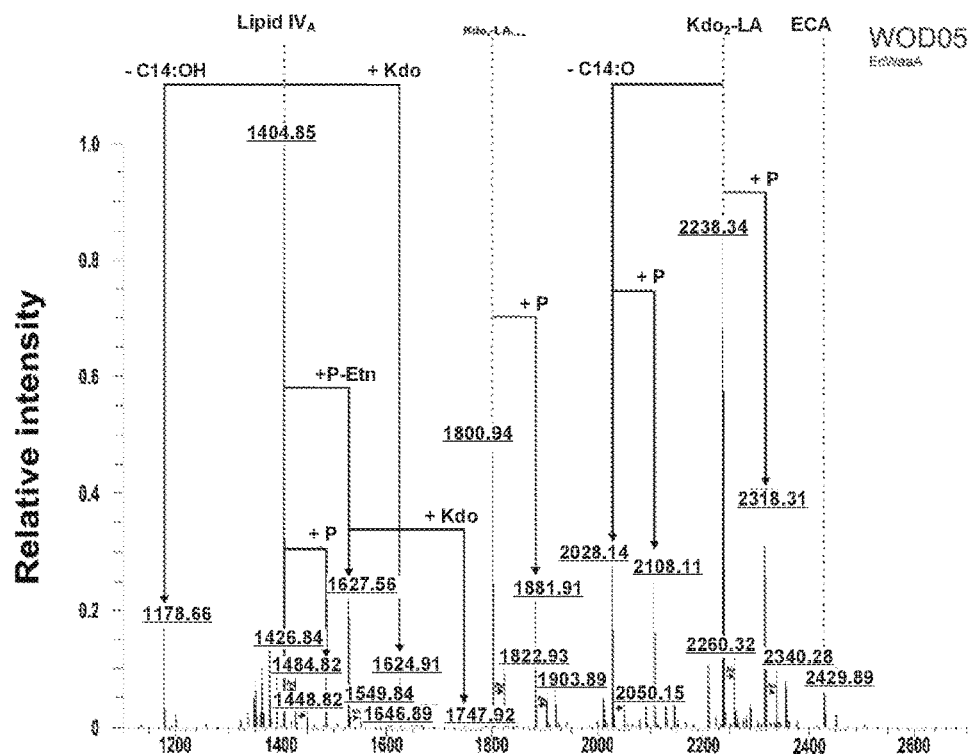
Mass spectrum of WOD05 with mass units of m/z.
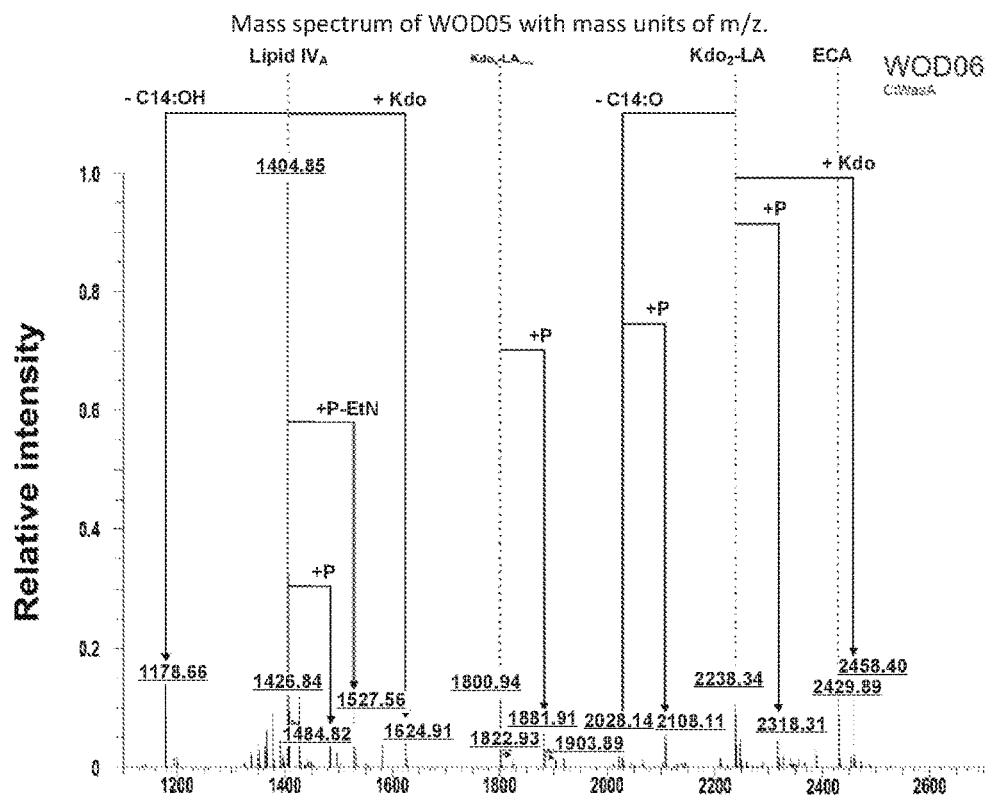
Mass spectrum of WOD06 with mass units of m/z.

FIG. 9C
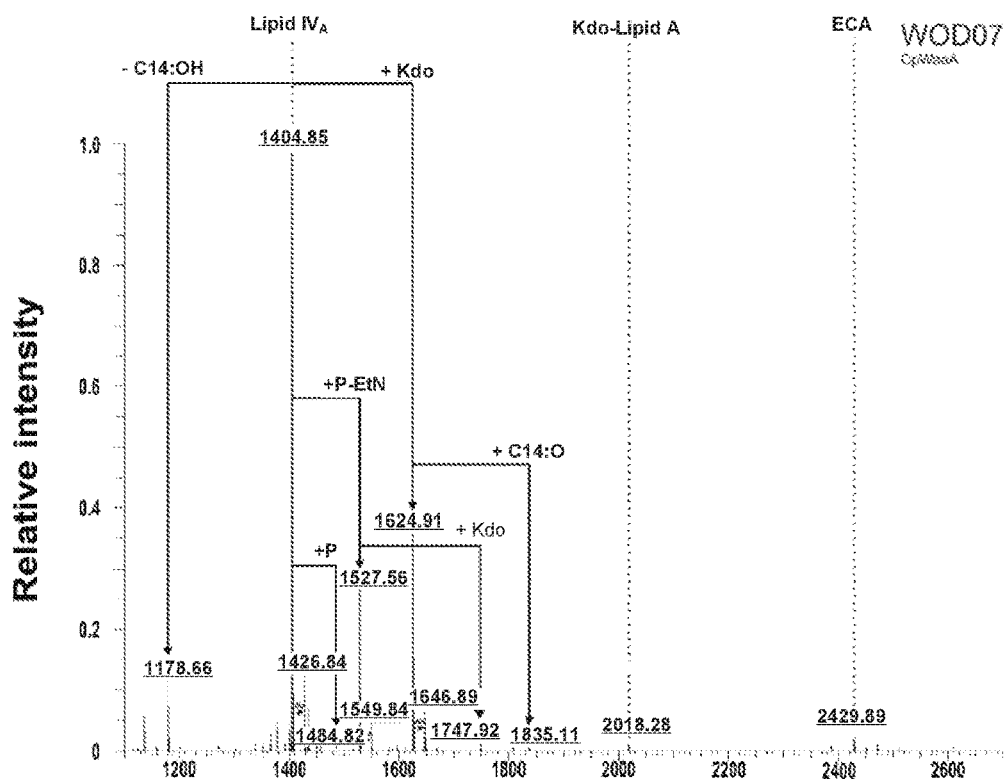
Mass spectrum of WOD07 with mass units of m/z.
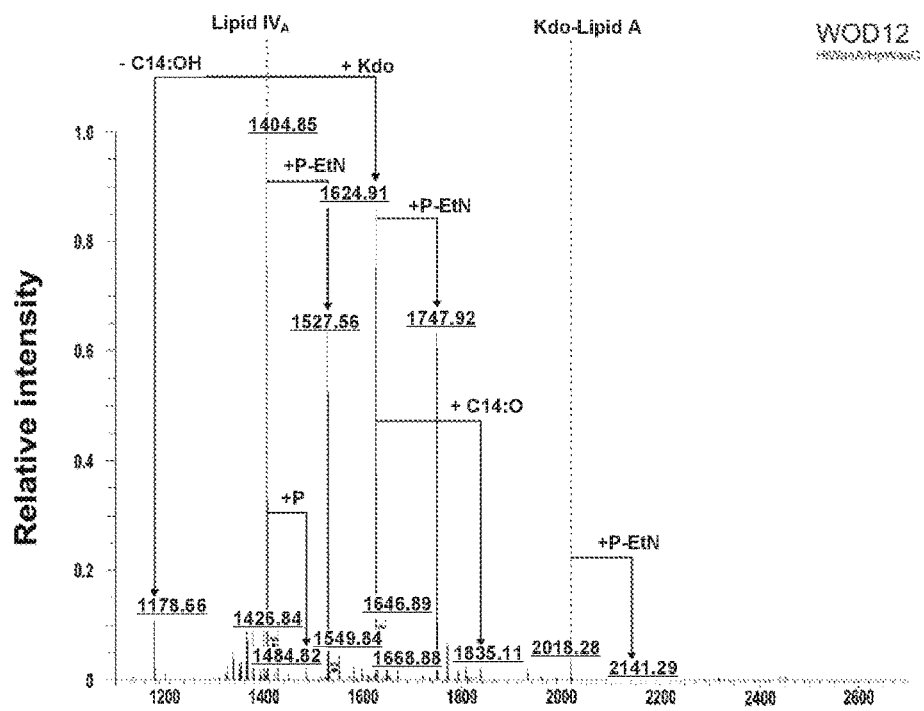
Mass spectrum of WOD08 with mass units of m/z.

Mass spectra of WOD08-11 which lack Kdo transferases with mass units of m/z.

FIG. 9E
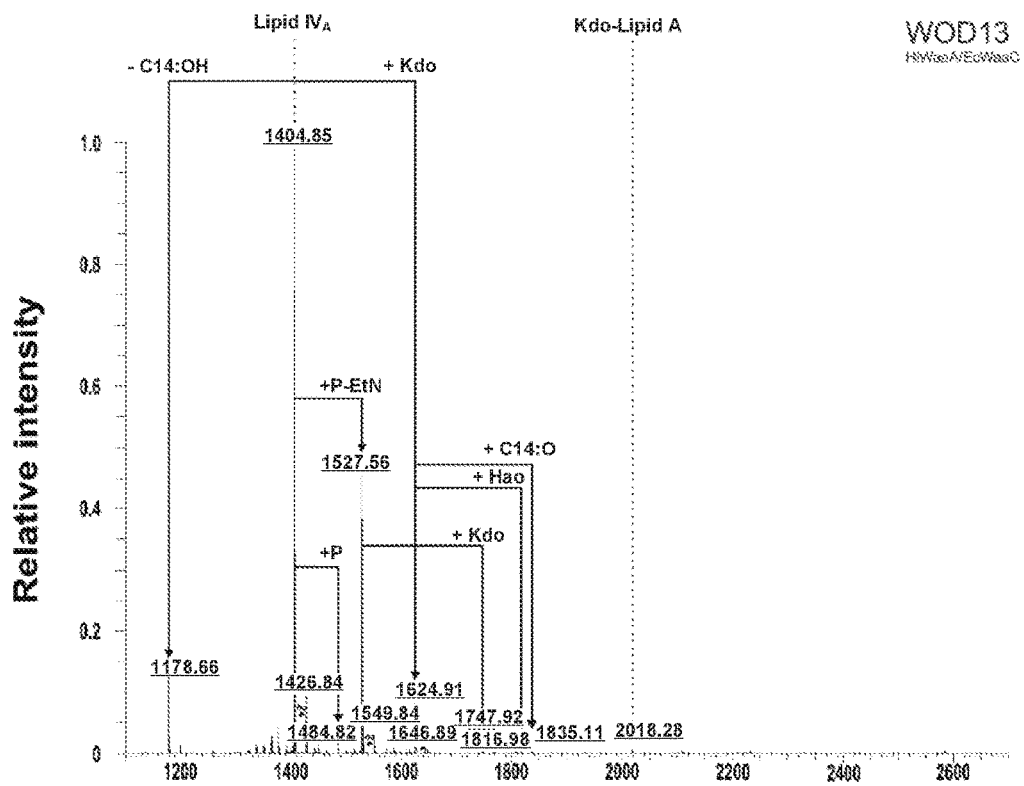
Mass spectra of WOD13 with mass units of m/z.
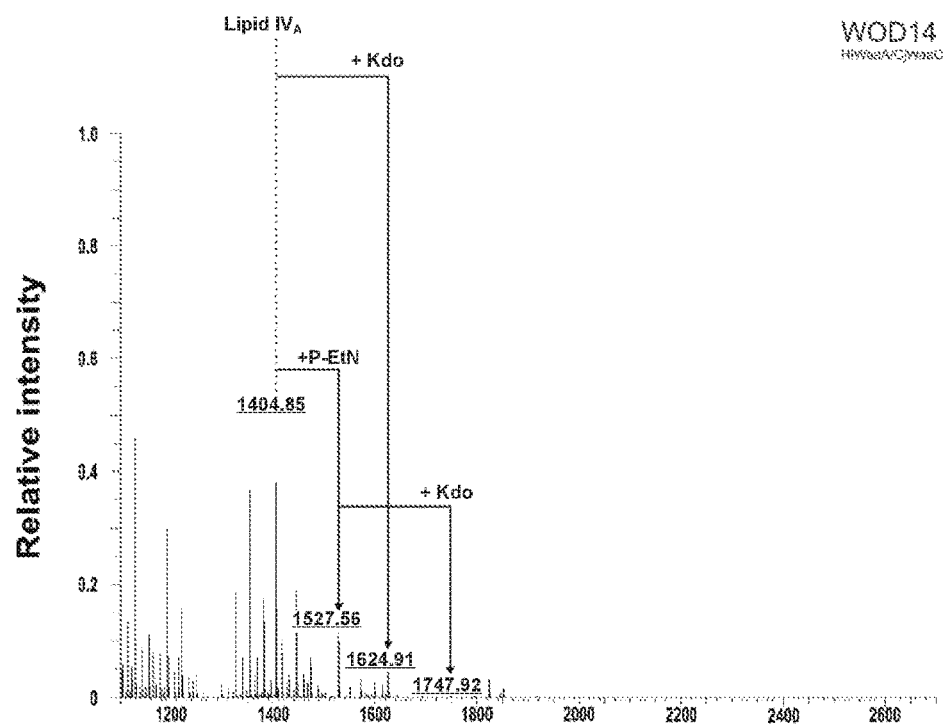
Mass spectra of WOD14 with mass units of m/z.

FIG. 9F
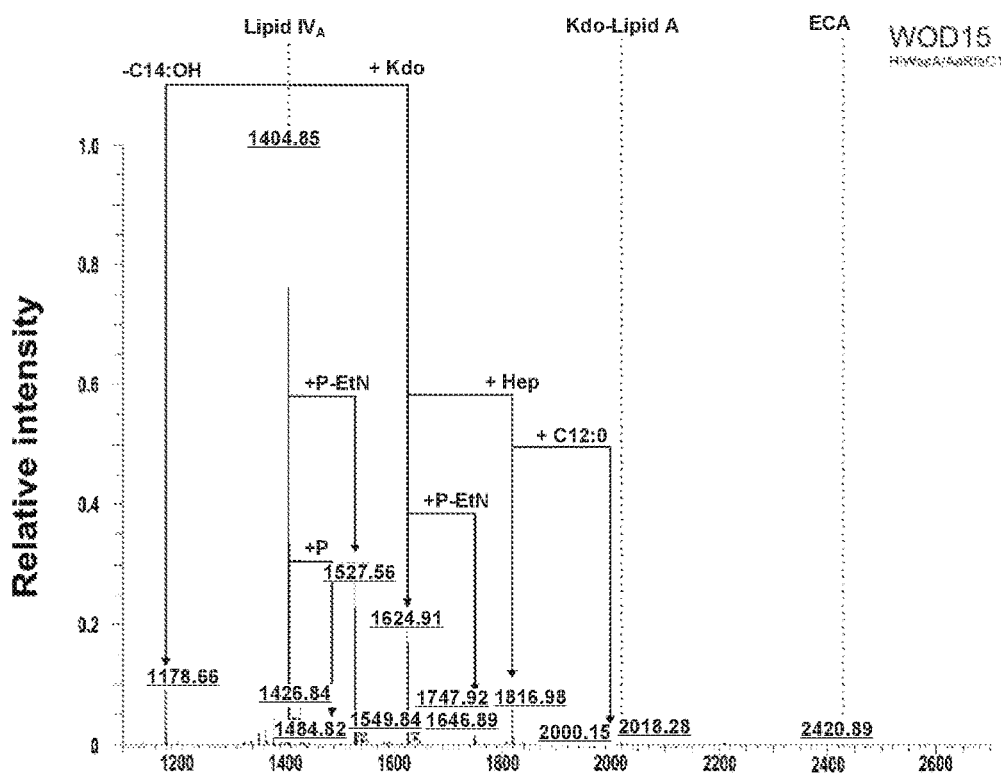
Mass spectra of WOD15 with mass units of m/z.
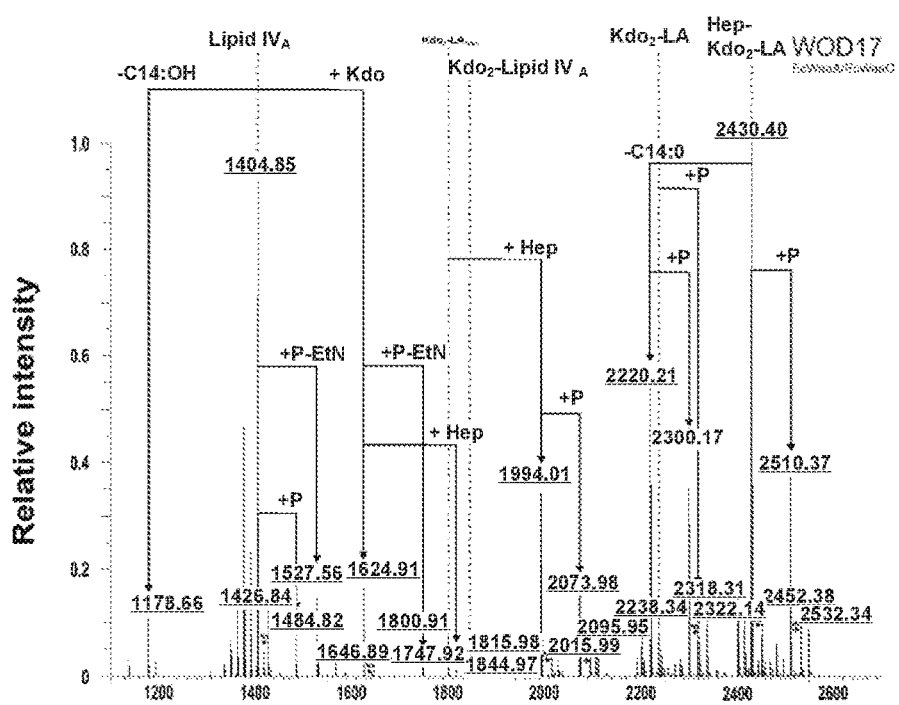
Mass spectra of WOD17 with mass units of m/z.

FIG. 9G
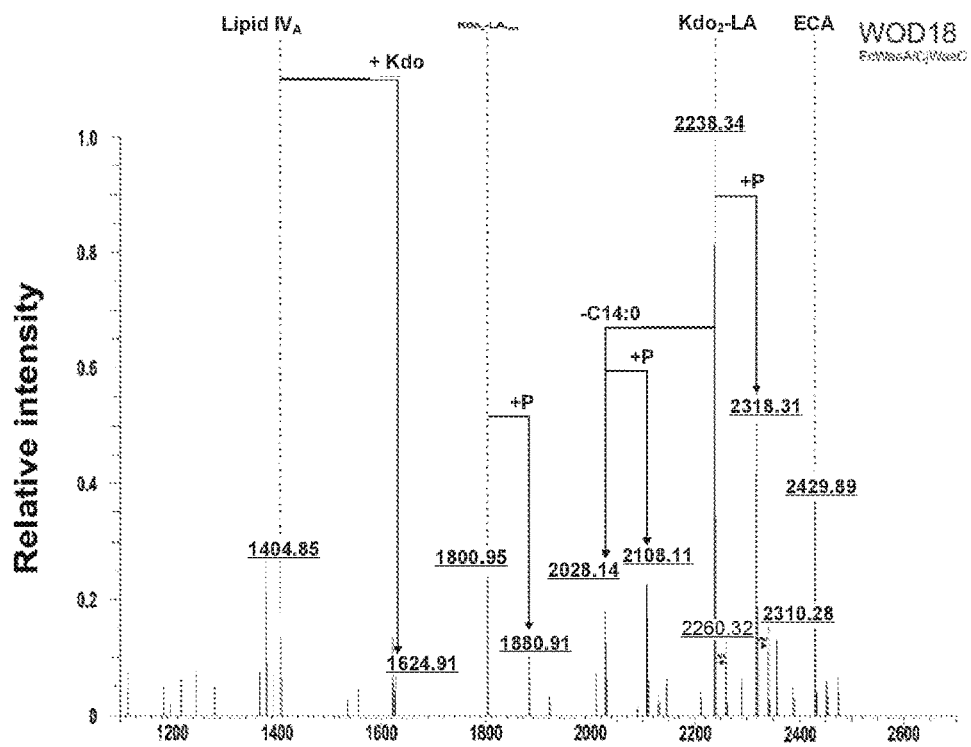
Mass spectra of WOD18 with mass units of m/z.
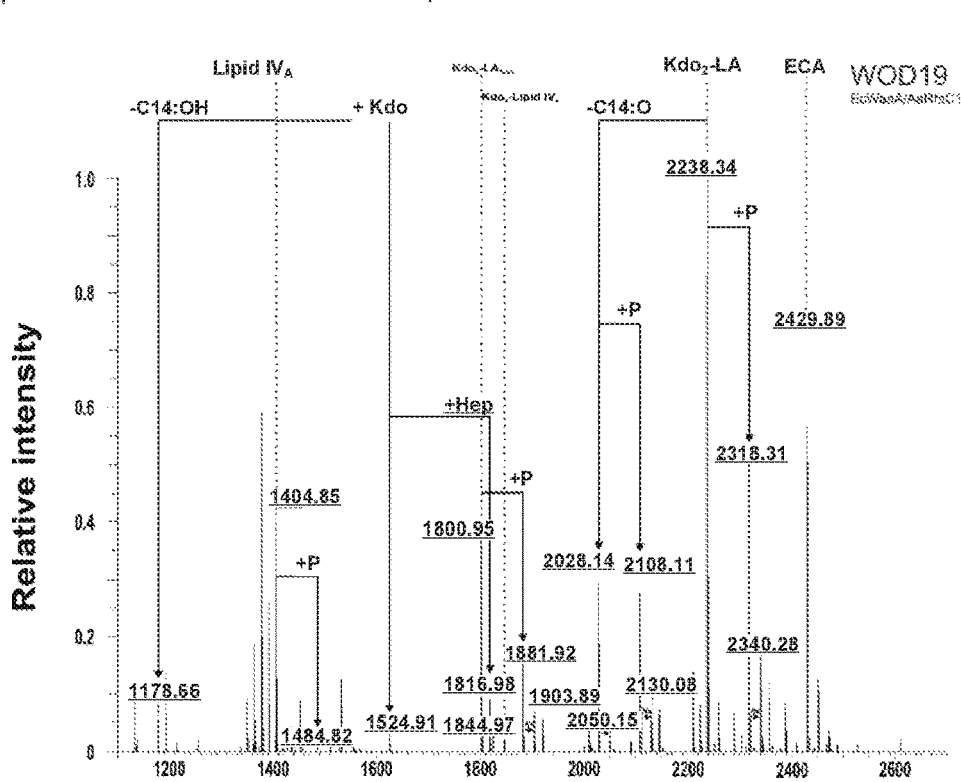
Mass spectra of WOD19 with mass units of m/z.

Mass spectra of WOD20 with mass units of m/z.

Mass spectra of WOD21 with mass units of m/z.

Mass spectra of WOD22 with mass units of m/z.

Mass spectra of WOD23 with mass units of m/z.

Mass spectra of WOD24 with mass units of m/z.

Mass spectra of WOD25 with mass units of m/z.

Mass spectra of WOD26 with mass units of m/z.

Mass spectra of WOD27 with mass units of m/z.

RECOMBINANT GRAM NEGATIVE BACTERIA AND METHODS OF GENERATING AND UTILIZING SAME

FIELD OF THE INVENTION

The present invention provides novel, recombinant Gram-negative bacteria. In particular, the invention provides recombinant Gram-negative bacteria (e.g., *E. coli*) lacking genes involved in lipopolysaccharide (LPS, endotoxin) biosynthesis (e.g., lacking genes required for core oligosaccharide biosynthesis) and also provides recombinant Gram-negative bacteria lacking genes involved in LPS biosynthesis that contain one or more exogenous KDO transferases and/or one or more exogenous heptosyltransferases (e.g., from one or more types and/or strains of bacteria). The invention further provides methods of generating and utilizing the recombinant Gram-negative bacteria in therapeutic, preventative, and/or research applications (e.g., as or in an immunogenic composition (e.g., as or in an adjuvant and/or vaccine)).

BACKGROUND OF THE INVENTION

Lipopolysaccharide (LPS) is the major component of the outer membrane of Gram-negative bacteria, contributing greatly to the structural integrity of the bacteria, and protecting the membrane from certain types of chemical attack. LPS also increases the negative charge of the cell membrane and helps stabilize the overall membrane structure. It is of crucial importance to Gram-negative bacteria, whose death may result if it is mutated or removed. LPS induces a strong response from normal animal immune systems. It has also been implicated in non-pathogenic aspects of bacterial ecology, including surface adhesion, bacteriophage sensitivity, and interactions with predators such as amoebae.

LPS is composed of three major components: lipid A, core oligosaccharide, and O-antigen. The lipid A portion is the region of least variability between different species and is often a hexaacylated disaccharide molecule. The core oligosaccharide is the linking region between the lipid A moiety and the O-antigen which show little variability between closely related species. The most variable region of LPS is the O-antigen which can vary widely even within different strains of the same species and is often composed of a repeating oligosaccharide and is often not present in common laboratory strains of Gram-negative bacteria such as in *Escherichia coli* K-12 MG1655 (See, e.g., Hobman et al., (2007) Molecular Microbiology 64, 881-885; Liu (1994) Microbiology 140, 49-57)

LPS acts as a prototypical endotoxin because it binds the CD14/TLR4/MD2 receptor complex in many cell types, but especially in monocytes, dendritic cells, macrophages and B cells, which promotes the secretion of pro-inflammatory cytokines, nitric oxide, and eicosanoids.

As part of the cellular stress response, superoxide is one of the major ROS species induced by LPS in various TLR expressing cell types. LPS is also an exogenous pyrogen (external fever-inducing substance). LPS produces many types of mediators involved in septic shock. Humans are much more sensitive to LPS than other animals (e.g., mice). For example, a dose of 1 µg/kg induces shock in humans, but mice will tolerate a dose up to a thousand times higher.

Endotoxins are in large part responsible for the dramatic clinical manifestations of infections with pathogenic Gram-negative bacteria, such as *Neisseria meningitidis*, the pathogen that causes meningococcal disease, including meningococcemia, Waterhouse-Friderichsen syndrome, and meningitis.

SUMMARY OF THE INVENTION

The present invention provides novel, recombinant Gram-negative bacteria. In particular, the invention provides recombinant Gram-negative bacteria (e.g., *E. coli*) lacking genes involved in lipopolysaccharide (LPS, endotoxin) biosynthesis (e.g., lacking genes required for core oligosaccharide biosynthesis) and also provides recombinant Gram-negative bacteria lacking genes involved in LPS biosynthesis that contain one or more exogenous KDO transferases and/or one or more exogenous heptosyltransferases (e.g., from one or more types and/or strains of bacteria). The invention further provides methods of generating and utilizing (e.g., as or in an immunogenic composition (e.g., as or in an adjuvant and/or vaccine)) the recombinant Gram-negative bacteria in therapeutic, preventative, and/or research applications.

Accordingly, in one embodiment, the invention provides a recombinant Gram-negative bacterial cell lacking endogenous glycosyltransferases involved in core oligosaccharide biosynthesis within lipopolysaccharide (LPS). For example, in one embodiment, the invention provides a recombinant Gram-negative bacterial cell lacking endogenous glycosyltransferase (e.g., KDO transferase) enzymes. The invention is not limited by the type or number of glycosyltransferase enzymes (e.g., KDO transferases) for which the bacterial cell is deficient. In one embodiment, the Gram-negative bacterial cell is deficient for two, three, four, five, six, seven, eight, nine, ten, eleven, twelve, thirteen or all of the genes waaF, waaC, waaL, waaU, waaZ, waaY, waaJ, waaR, waaB, waaS, waaP, waaG, waaQ, and waaA encoding glycosyltransferase (e.g., KDO transferase) enzymes. In another embodiment, the Gram-negative bacterial cell comprises the machinery required to generate sugar precursors of core oligonucleotide biosynthesis but lacks the capability to transfer these sugars to the Lipid $IV_A$ molecule. Thus, in a preferred embodiment, the invention provides a Gram-negative bacterial cell and/or cell line that generates sugar precursors of core oligonucleotide biosynthesis but lacks the capability to transfer these sugars to the Lipid $IV_A$ molecule (e.g., due to deficiency of (e.g., genetic modification to remove) two, three, four, five, six, seven, eight, nine, ten, eleven, twelve, thirteen or all of the genes waaF, waaC, waaL, waaU, waaZ, waaY, waaJ, waaR, waaB, waaS, waaP, waaG, waaQ, and waaA encoding glycosyltransferase (e.g., KDO transferase) enzymes. In one embodiment, the Gram-negative bacterial cell contains endogenous hldD and coaD genes. The invention is not limited by the type of Gram-negative bacterial cell. Indeed, any Gram-negative bacterial cell may be utilized to make a recombinant Gram-negative bacterial cell of the invention including, but not limited to, a bacterial cell is from the genus *Escherichia, Shigella., Salmonella, Campylobacter, Neisseria, Haemophilus, Aeromonas, Francisella, Yersinia, Klebsiella, Bordetella, Legionella, Corynebacteria, Citrobacter, Chlamydia, Brucella, Pseudomonas, Helicobacter,* and/or *Vibrio.*

In another embodiment, the invention provides a Gram-negative bacterial cell and/or cell line lacking/deficient for endogenous glycosyltransferases (e.g., KDO transferases) that are further modified (e.g., genetically modified) to display inner and/or outer core oligosaccharides from a separate second, third, fourth or more different Gram-negative bacteria. For example, as one non-limiting example, the invention provides a specific Gram-negative bacterial cell (e.g., *E. coli*) that is modified to lack endogenous glycosyltransferases (e.g., KDO transferases) and is further modified to display the appearance of other pathogenic Gram-negative bacteria (e.g., *Aquifex aeolicus, Haemophilus influenzae, Campylobacter jejuni, Klebsiella pneumoniae, Helicobacter pylori, Chlamydia trachomatis, Acinetobacter baumannii, Coxiella burnetii, Chlamydophila psittaci*, or even a different strain of *Escherichia coli*) via the expression of one or more exogenous KDO transferases and/or heptosyltransferases. For example, in one embodiment, the invention provides recombinant Gram-negative bacterial cells and/or cell lines (e.g., cell or cell line lacking its endogenous waa operon) that generate and/or express inner core oligosaccharides (e.g., due to expression of one or more exongenous WaaA species (e.g., expression of one or more monofunctional, bifunctional, trifunctional and/or tetrafunctional WaaA species) not found in their wild type counterparts. The recombinant Gram-negative bacterial cell and/or cell line may be any Gram-negative cell or cell line lacking endogenous glycosyltransferases involved in core oligosaccharide biosynthesis within lipopolysaccharide (LPS) (e.g., responsible for transferring sugars to the Lipid $IV_A$ molecule) that contain one or more exogenous KDO transferases and/or heptosyltransferases (e.g., from a separate Gram-negative bacteria or separate bacterial strain thereby providing the cell the capacity to generate LPS glycoforms not found in the native, wild-type Gram-negative cell prior to its modification (e.g., recombinant modification) to remove its endogenous glycosyltransferases). The invention is not limited by the type or source of WaaA/KDO transferase for incorporation (e.g., recombinant modification) into a Gram-negative bacterial cell lacking its endogenous glycosyltransferases (e.g., KDO transferases). Indeed, any WaaA/KDO transferase from any Gram-negative bacteria may be used including, but not limited to, any one or more monofunctional, bifunctional, trifunctional and/or tetrafunctional WaaA species/KDO transferases from a Gram negative bacteria including, but not limited to, *Aquifex aeolicus, Haemophilus influenzae, Campylobacter jejuni, Klebsiella pneumoniae, Helicobacter pylori, Chlamydia trachomatis, Acinetobacter baumannii, Coxiella burnetii, Chlamydophila psittaci*, and/or *E. coli*. In one embodiment, the WaaA species is a monofunctional KDO transferase from a Gram negative bacteria such as *Aquifex aeolicus, Haemophilus influenzae, Campylobacter jejuni*, or other Gram negative bacteria known in the art to possess a monofunctional KDO transferase (e.g., that transfers a single KDO molecule to Lipid A). In another embodiment, the WaaA species is a bifunctional KDO transferase from a Gram negative bacteria such as *Escherichia coli, Klebsiella pneumoniae, Helicobacter pylori*, or other Gram negative bacteria known in the art to possess a bifunctional KDO transferase (e.g., that transfers two KDO molecules to Lipid A). In yet another embodiment, the WaaA species is a trifunctional KDO transferase from a Gram negative bacteria such as *Chlamydia trachomatis, Acinetobacter baumannii, Coxiella burnetii*, or other Gram negative bacteria known in the art to possess a trifunctional KDO transferase (e.g., that transfers three KDO molecules to Lipid A). In another embodiment, the WaaA species is a tetrafunctional KDO transferase from a Gram negative bacteria such as *Chlamydophila psittaci* or other Gram negative bacteria known in the art to possess a tetrafunctional KDO transferase (e.g., that transfers four KDO molecules to Lipid A). Similarly, the invention is not limited by type or source of heptosyltransferase for incorporation (e.g., recombinant modification) into a Gram-negative bacterial cell lacking its endogenous glycosyltransferases (e.g., KDO transferases). Indeed, any heptosyltransferase from any Gram-negative bacteria may be used including, but not limited to, a heptosyltransferase from *Helicobacter pylori*, a heptosyltransferase from *E. coli*, a heptosyltransferase from *Campylobacter jejuni*, and/or a heptosyltransferase from *Aquifex aeolicus*. Indeed, any KDO transferase and/or heptosyltransferase from any source (e.g., from any Gram-negative bacterial cell from the genus *Escherichia, Shigella., Salmonella, Campylobacter, Neisseria, Haemophilus, Aeromonas, Francisella, Yersinia, Klebsiella, Bordetella, Legionella, Corynebacteria, Citrobacter, Chlamydia, Brucella, Pseudomonas, Helicobacter*, and/or *Vibrio*) may be obtained and incorporated into (e.g., genetically recombined to be expressed in) a Gram-negative bacterial cell lacking its endogenous glycosyltransferases (e.g., KDO transferases) of the invention.

The invention is not limited by the type of Gram-negative bacteria utilized (e.g., for generation of recombinant bacterial cells and cell lines described herein). Indeed, the invention contemplates the use of any type of Gram-negative bacterial strain in the construction of Gram-negative bacterial cells and/or cell lines lacking/deficient for endogenous glycosyltransferases (e.g., that transfer sugar precursors of core oligonucleotide biosynthesis to the Lipid $IV_A$ molecule (e.g., that are optionally further modified (e.g., genetically modified) to display inner and/or outer core oligosaccharides of a second, third, fourth or more Gram-negative bacteria)). Examples of Gram-negative bacteria useful in the present invention include, but are not limited to, a bacteria from any one of the genera *Escherichia, Shigella., Salmonella, Campylobacter, Neisseria, Haemophilus, Aeromonas, Francisella, Yersinia, Klebsiella, Bordetella, Legionella, Corynebacteria, Citrobacter, Chlamydia, Brucella, Pseudomonas, Helicobacter*, and *Vibrio*. In a preferred embodiment, *E. coli* is used.

In a further embodiment, the invention provides lipopolysaccharide (LPS) isolated from a strain of recombinant Gram-negative bacteria of the invention (e.g., Gram-negative bacterial cell or cell line genetically modified to lack endogenous glycosyltransferases involved in core oligosaccharide biosynthesis within lipopolysaccharide (LPS) and optionally further modified to contain one or more exogenous KDO transferases and/or heptosyltransferases).

In another embodiment, the invention provides an immunogenic composition comprising recombinant Gram-negative bacterial cells, or an antigenic component thereof, of the invention (e.g., Gram-negative bacterial cell or cell line genetically modified to lack endogenous glycosyltransferases involved in core oligosaccharide biosynthesis within lipopolysaccharide (LPS) and optionally further modified to contain one or more exogenous KDO transferases and/or heptosyltransferases). The invention is not limited by the type of antigenic component used in an immunogenic composition of the invention. Non-limiting examples of antigenic components include, but are not limited to, antigenic polypeptides, antigenic proteins, antigenic glycoprotein, antigenic lipoprotein, antigenic glycopeptide, antigenic toxoid, antigenic carbohydrate, antigenic polysaccharides, antigenic membrane components, and combinations thereof.

In a further embodiment, the invention provides a method of inducing an immune response in a subject (e.g., a mammal (e.g., a human) comprising administering to the subject an immunogenic composition of the invention. As one non-limiting example, in one embodiment, the invention provides a method of generating an immune response in a subject, including a human, comprising administering thereto an immunogenic composition of the present invention (e.g., comprising one or more antigens/immunogens together with LPS isolated from a strain of recombinant Gram-negative bacteria of the invention). The invention is not limited by the type of immune response generated and refers to any type of immune response, including, but not limited to, innate immune responses (e.g., activation of Toll receptor signaling cascade), cell-mediated immune responses (e.g., responses mediated by T cells (e.g., antigen-specific T cells) and non-specific cells of the immune system), and humoral immune responses (e.g., responses mediated by B cells (e.g., via generation and secretion of antibodies into the plasma, lymph, and/or tissue fluids). Immune response is meant to refer to the ability of a subject's immune system to respond to antigens and/or immunogens (e.g., both the initial response to an immunogen (e.g., a pathogen) as well as acquired (e.g., memory) responses that are a result of an adaptive immune response). Immune responses include, but are not limited to, detectable alteration (e.g., increase) in Toll-like receptor (TLR) activation, lymphokine (e.g., cytokine (e.g., Th1 or Th2 type cytokines) or chemokine) expression and/or secretion, macrophage activation, dendritic cell activation, T cell activation (e.g., CD4+ or CD8+ T cells), NK cell activation, B cell activation (e.g., antibody generation and/or secretion), binding of an immunogen (e.g., antigen (e.g., immunogenic polypeptide)) to an MHC molecule and inducing a cytotoxic T lymphocyte ("CTL") response, inducing a B cell response (e.g., antibody production), T-helper lymphocyte response, a delayed type hypersensitivity (DTH) response against antigen (e.g., from which an immunogenic polypeptide is derived), expansion (e.g., growth of a population of cells) of cells of the immune system (e.g., T cells, B cells (e.g., of any stage of development (e.g., plasma cells), and/or increased processing and presentation of antigen by antigen presenting cells.

BRIEF DESCRIPTION OF THE DRAWINGS

FIG. 3 shows a table depicting a summary of the activities of the KDO transferases used in experiments conducted during development of embodiments of the invention.

FIG. 4 shows a table depicting a summary of the activities of the heptosyltransferases used in experiments conducted during development of embodiments of the invention.

FIG. 6A-FIG. 6C shows bacterial strains, plasmids, growth conditions, and primer sequences used in experiments conducted during development of embodiments of the invention.

FIG. 7 shows the gene clusters containing the waa genes involved in core oligosaccharide biosynthesis.

FIG. 8A-FIG. 8B shows electrospray ionization Fourier transform ion cyclotron resonance mass spectrometry (ESI FT ICR MS) spectra of LPS samples generated from WODO2 cells described herein. A list of mass peaks of LPS analogs identified is provided. Due to isotopic distributions above 1844.97 major peaks are 1 u higher.

DEFINITIONS

Figure 1:
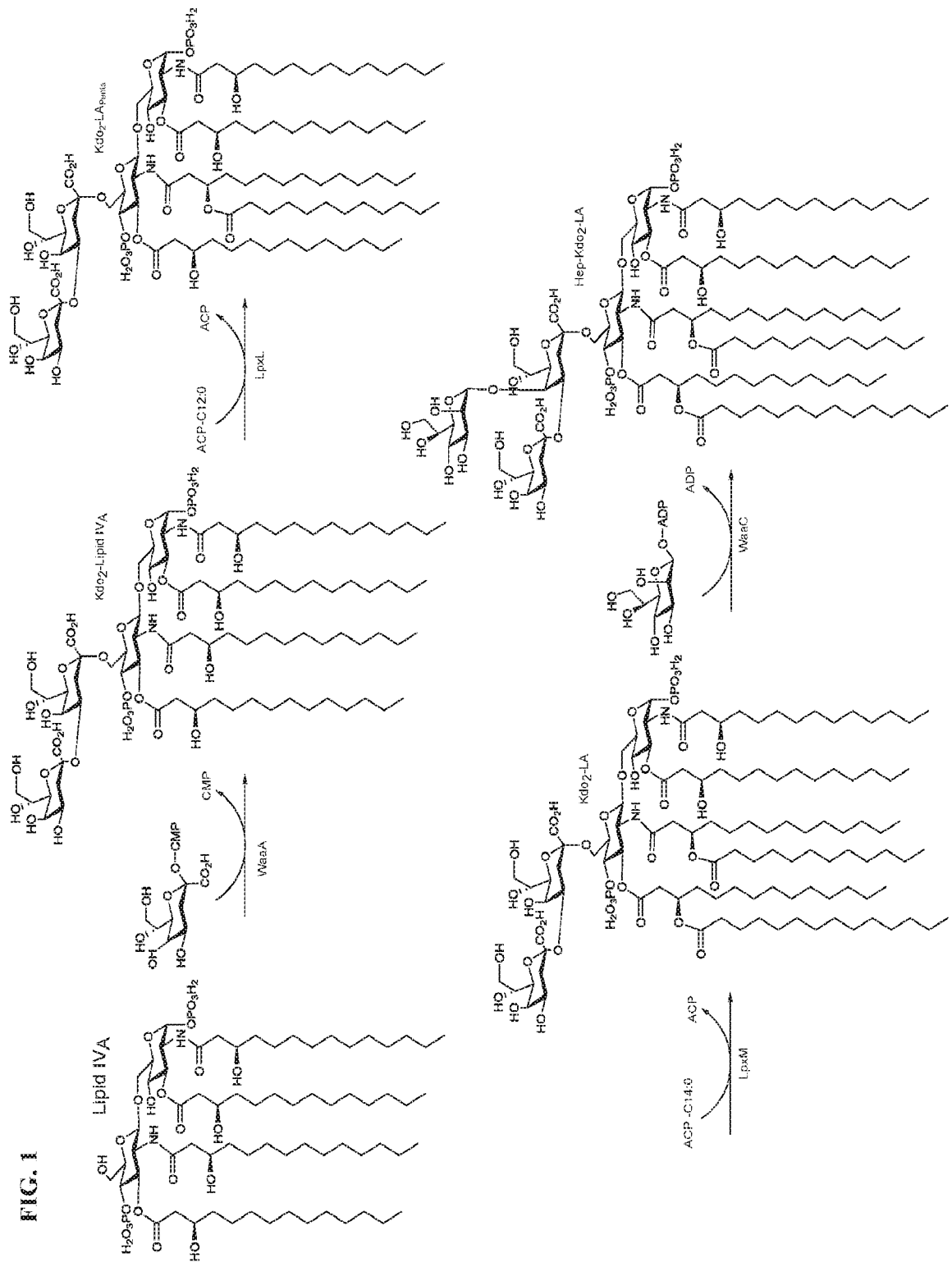
FIG. 1 depicts a biosynthetic scheme of the early modification of Lipid $IV_A$ in *E. coli* K-12 including the glycosylation by WaaA, fatty acid acylation by LpxL and LpxM to generate the endotoxic Lipid A anchor followed by heptosylation by WaaC.
Figure 2:
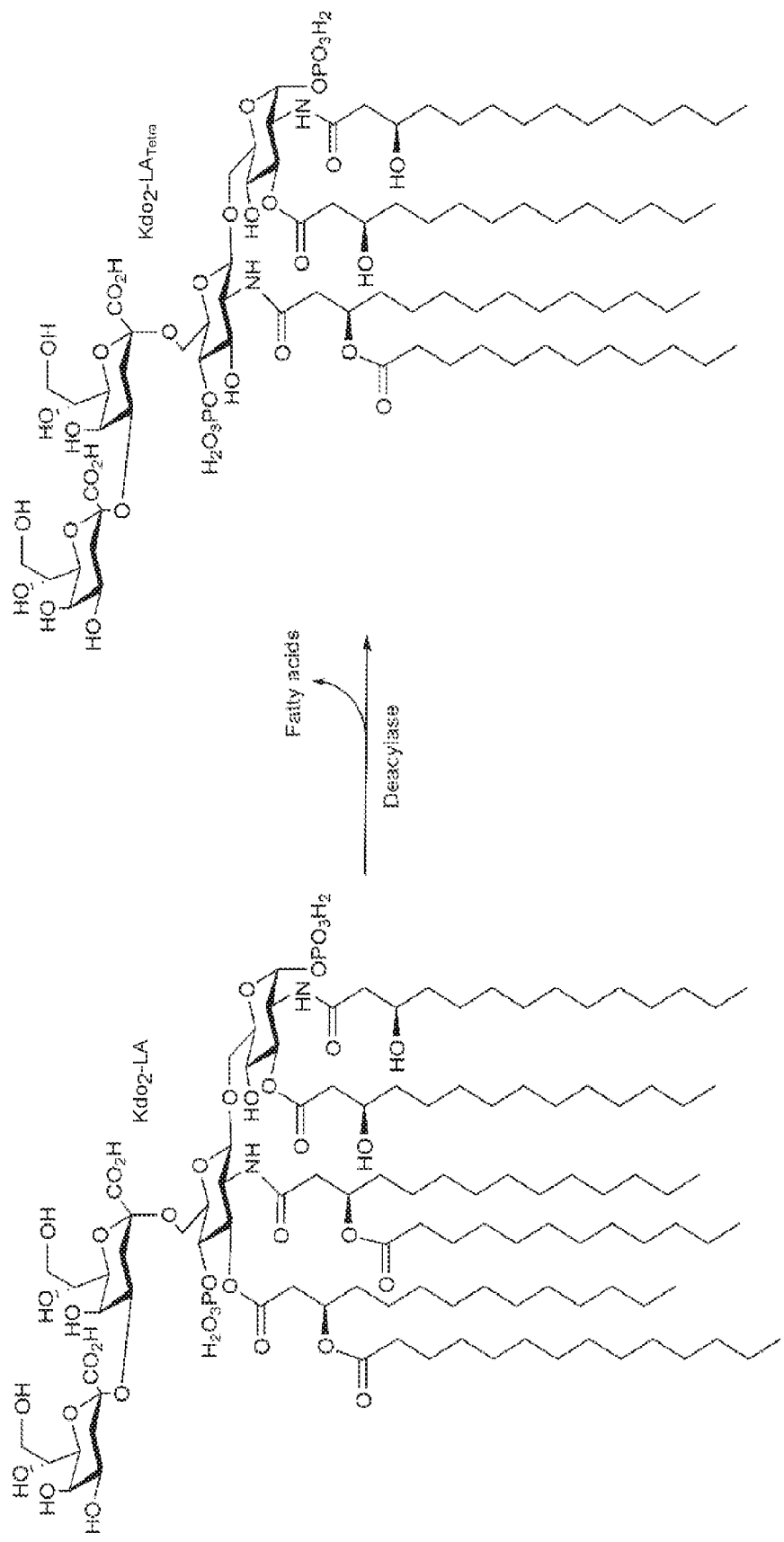
FIG. 2 shows a schematic of the predicted activity of O-deacylation.
Figure 5A:
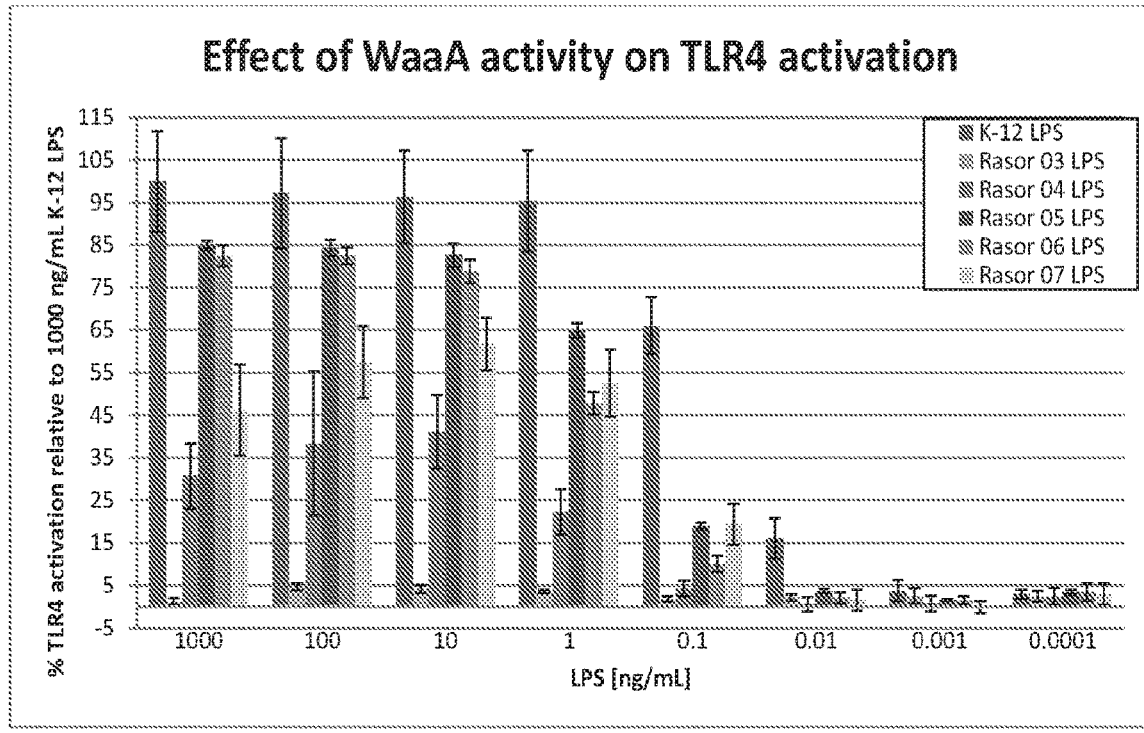
FIG. 5A-5E show activation of hTLR4 using LPS samples purified from waa operon deletion (WOD) 03 which lacks all glycosyltransferases for core region biosynthesis was observed to be the lowest of all samples tested with lower than 2% activity compared to full *E. coli* K-12 LPS at the same concentration. The addition of KDO transferases helped to return hTLR4 activation to these cells. The addition of only a single KDO (seen in WOD04) returned a low hTLR4 activation while the other cell lines displayed a higher return of hTLR4 activation. A comparison each KDO transferase with each heptosyltransferase indicated that in general, the addition of a heptosyltransferase for EcWaaA, CtWaaA, and to a lesser extent CpWaaA, appeared to have little to no difference on the overall hTLR4 activation.
Figure 5B:
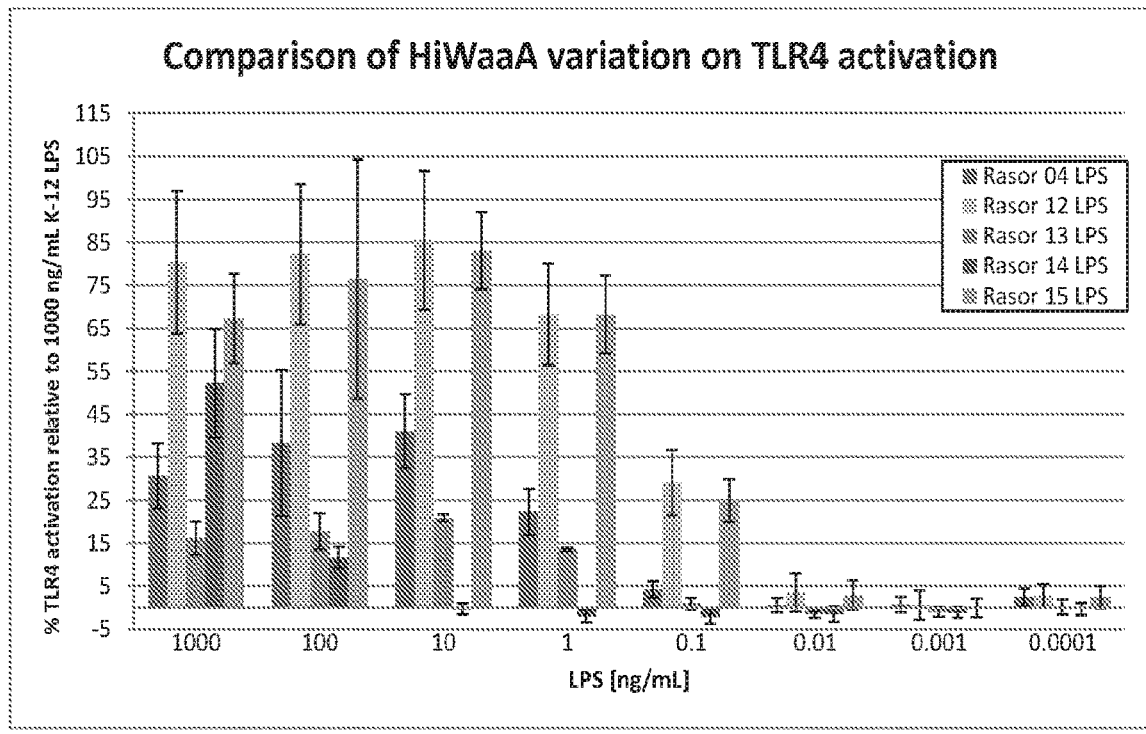
Figure 5C:
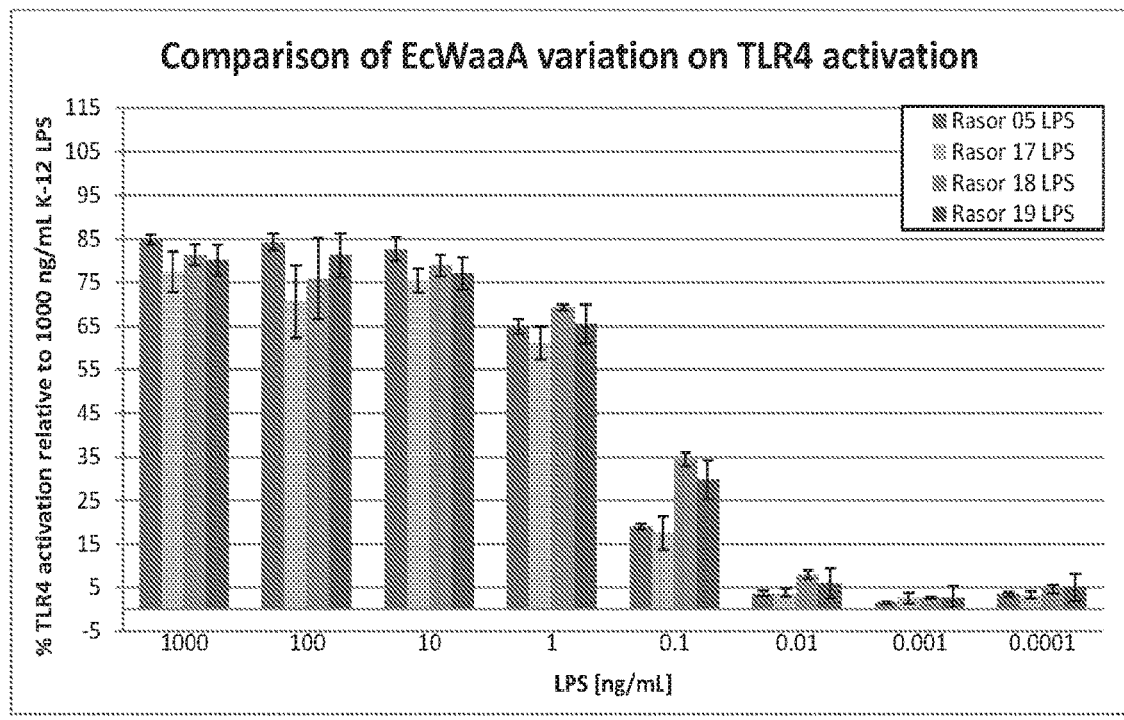
Figure 5D:
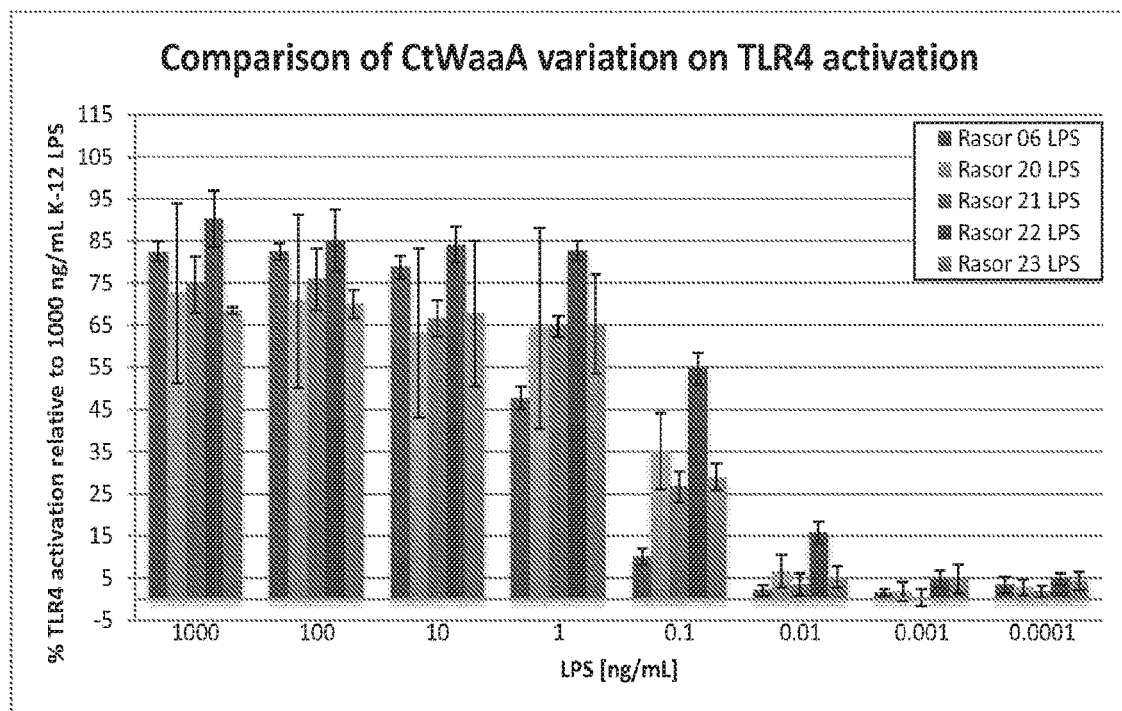
Figure 5E:
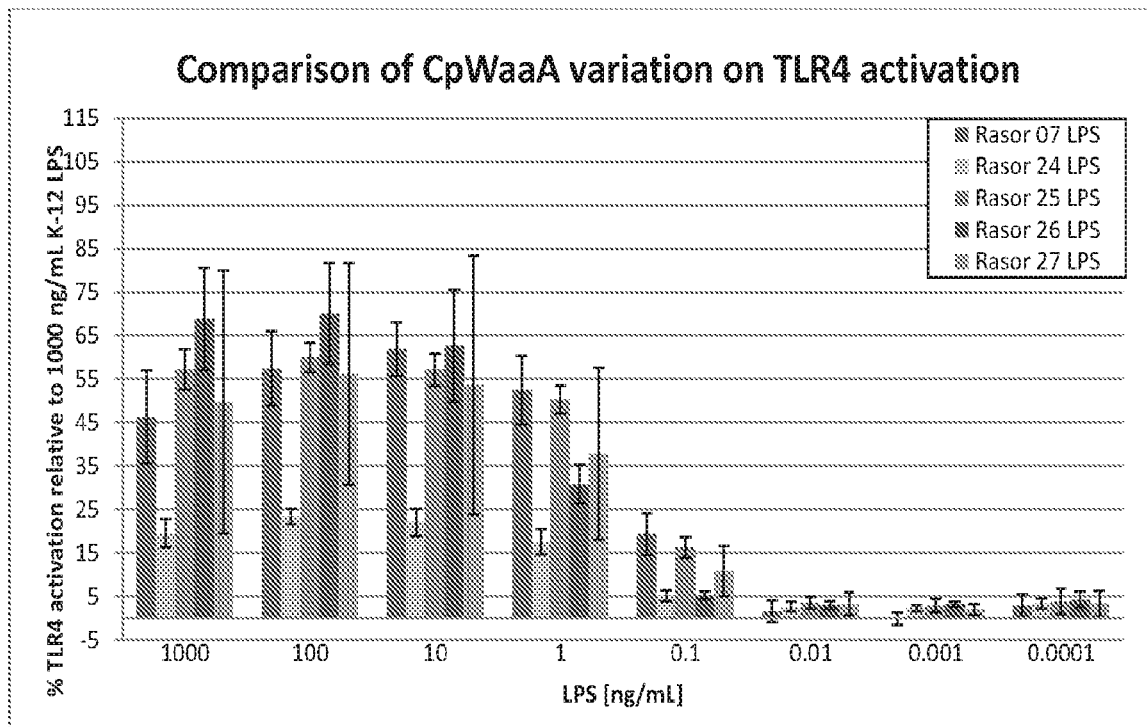
Figure 9D:
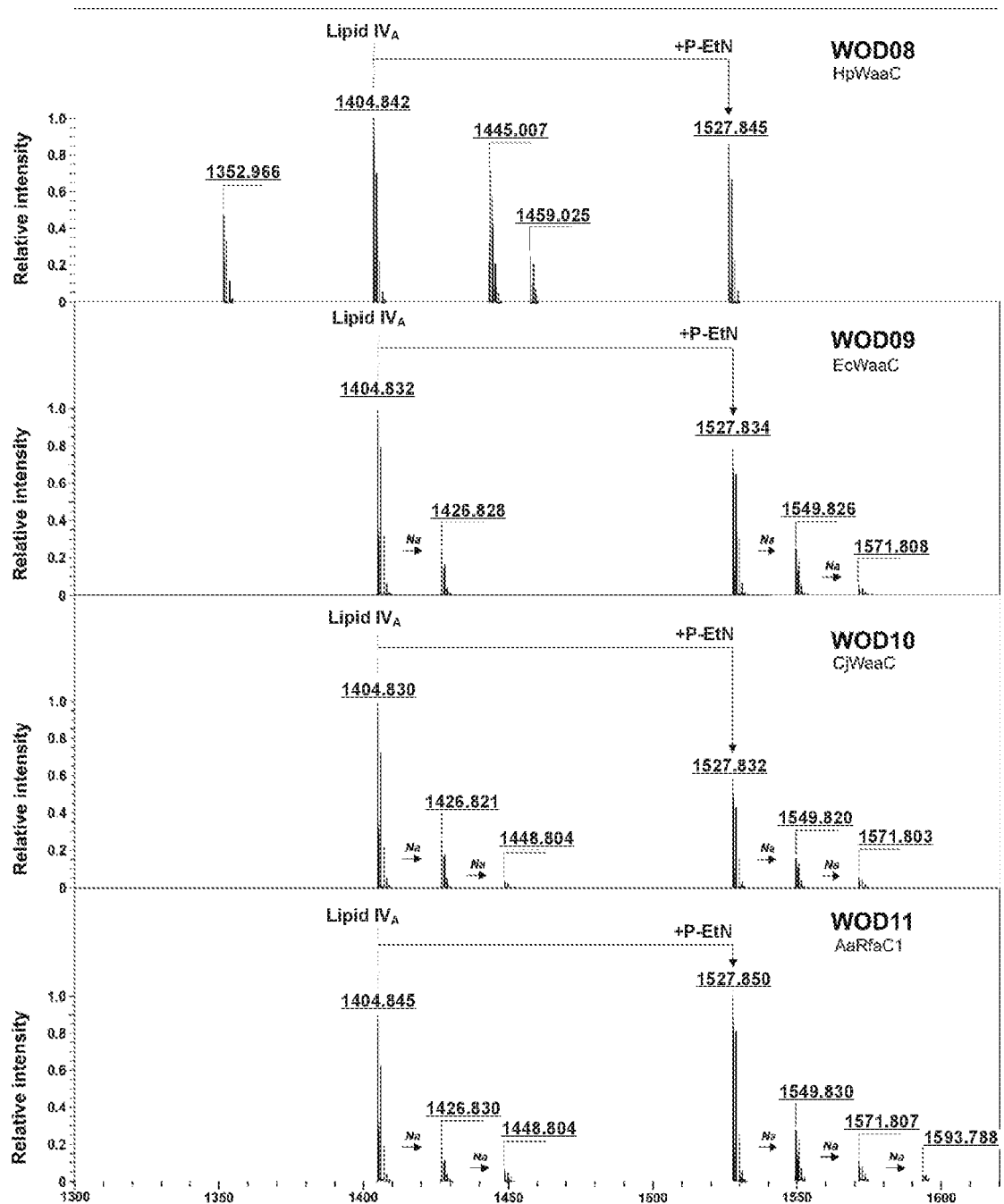
FIG. 9A-FIG. 9O shows mass spectra of purified LPS samples from WODO2 derivatives, generated during development of embodiments of the invention, from m/z 1100-2700 u.
Figure 9H:
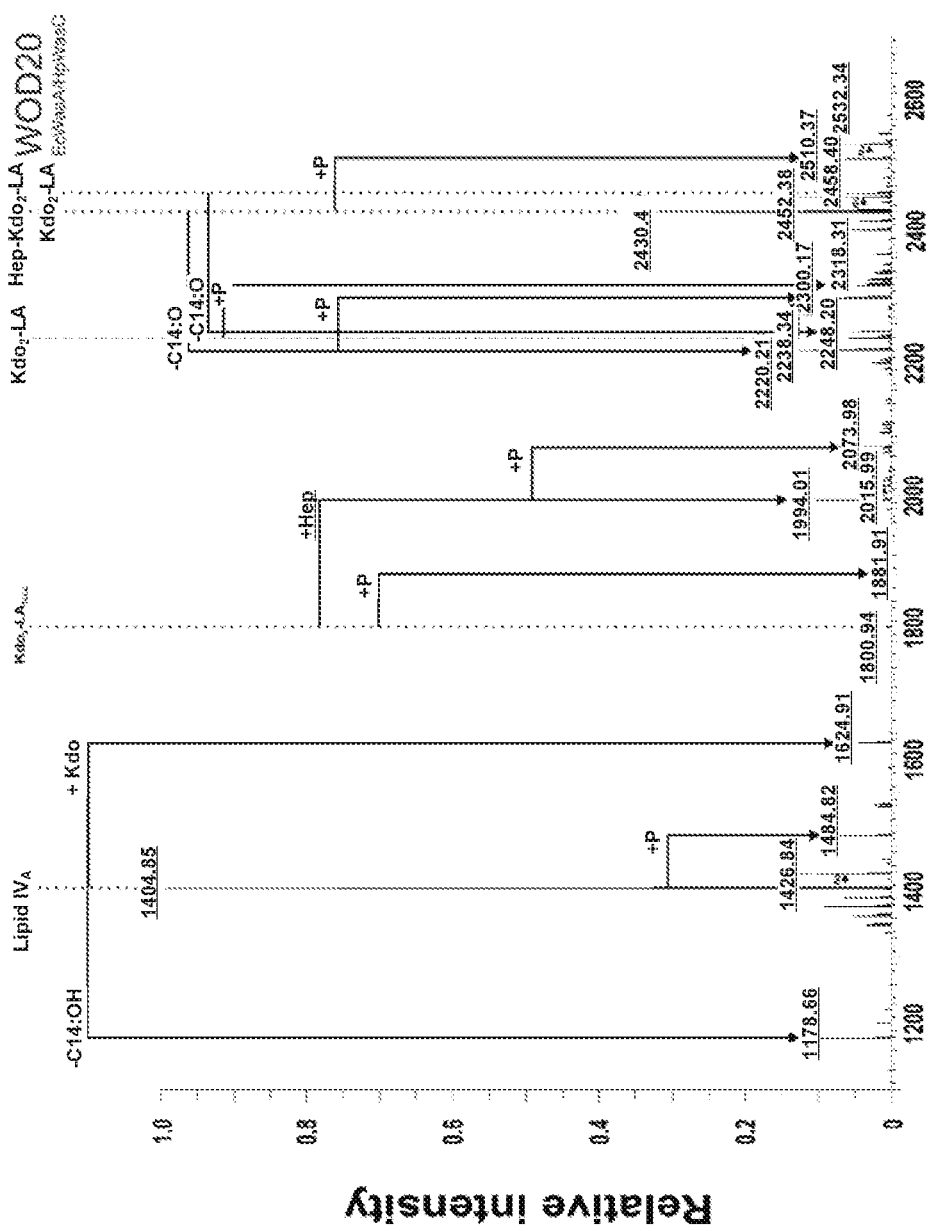
Figure 9I:
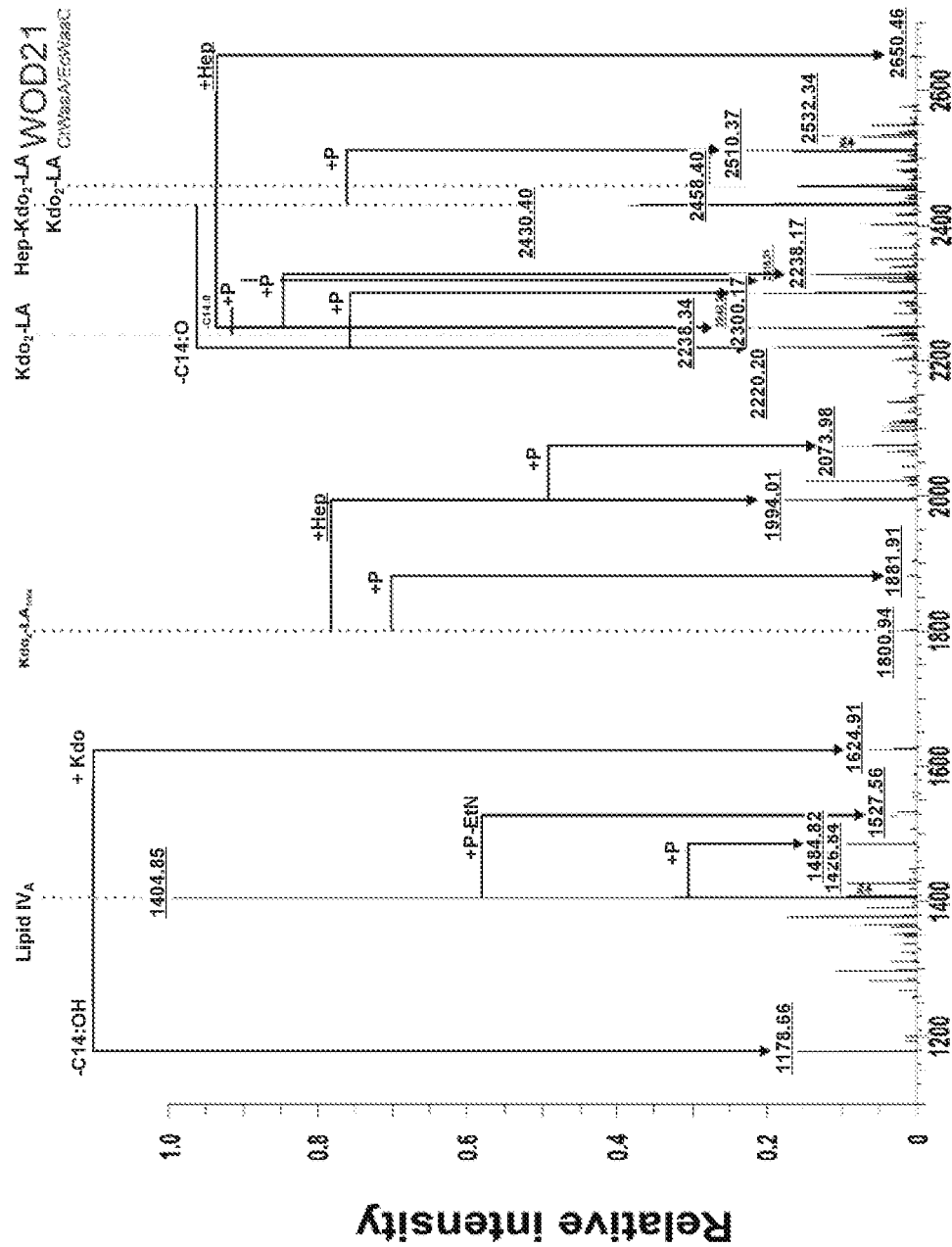
Figure 9J:
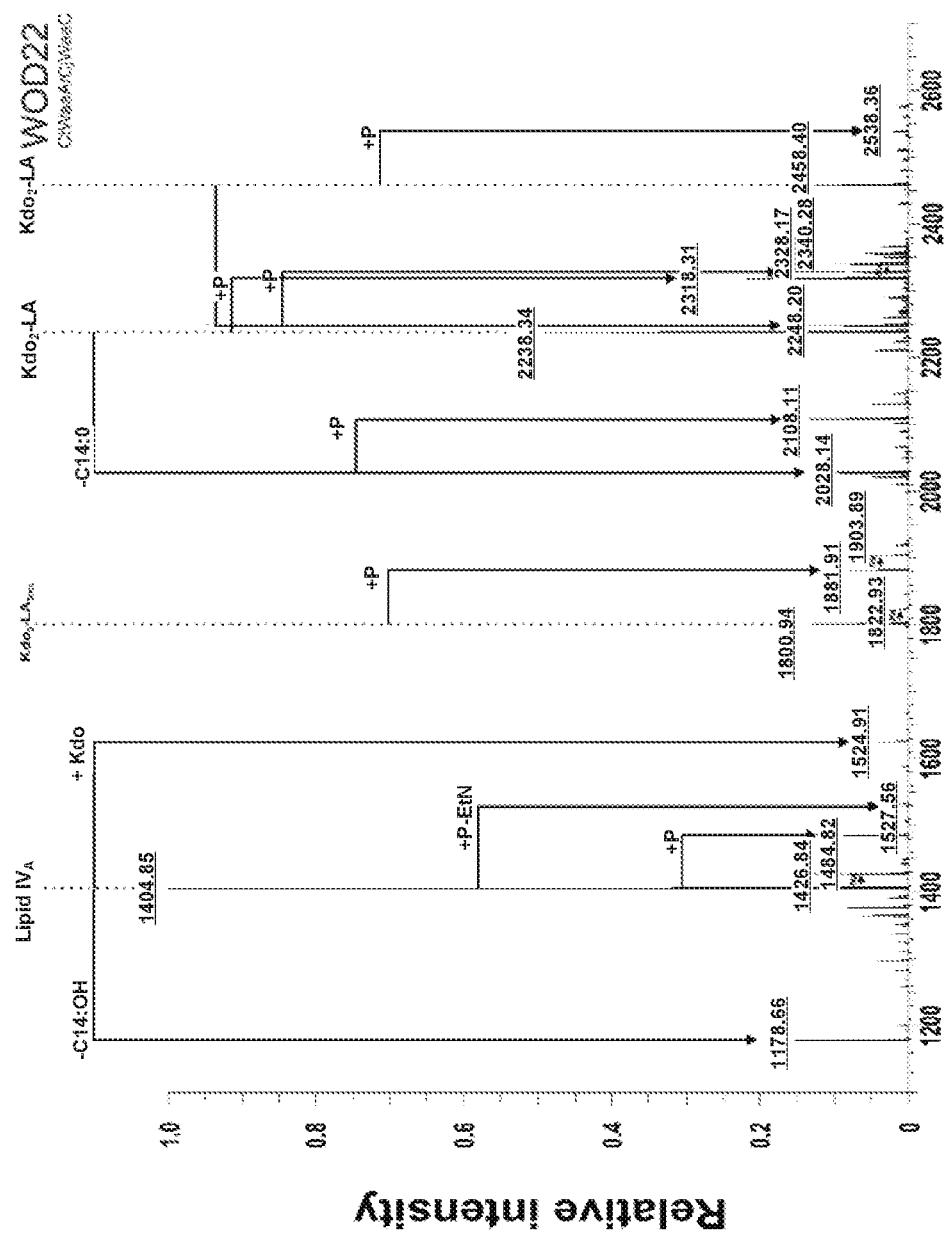
Figure 9K:
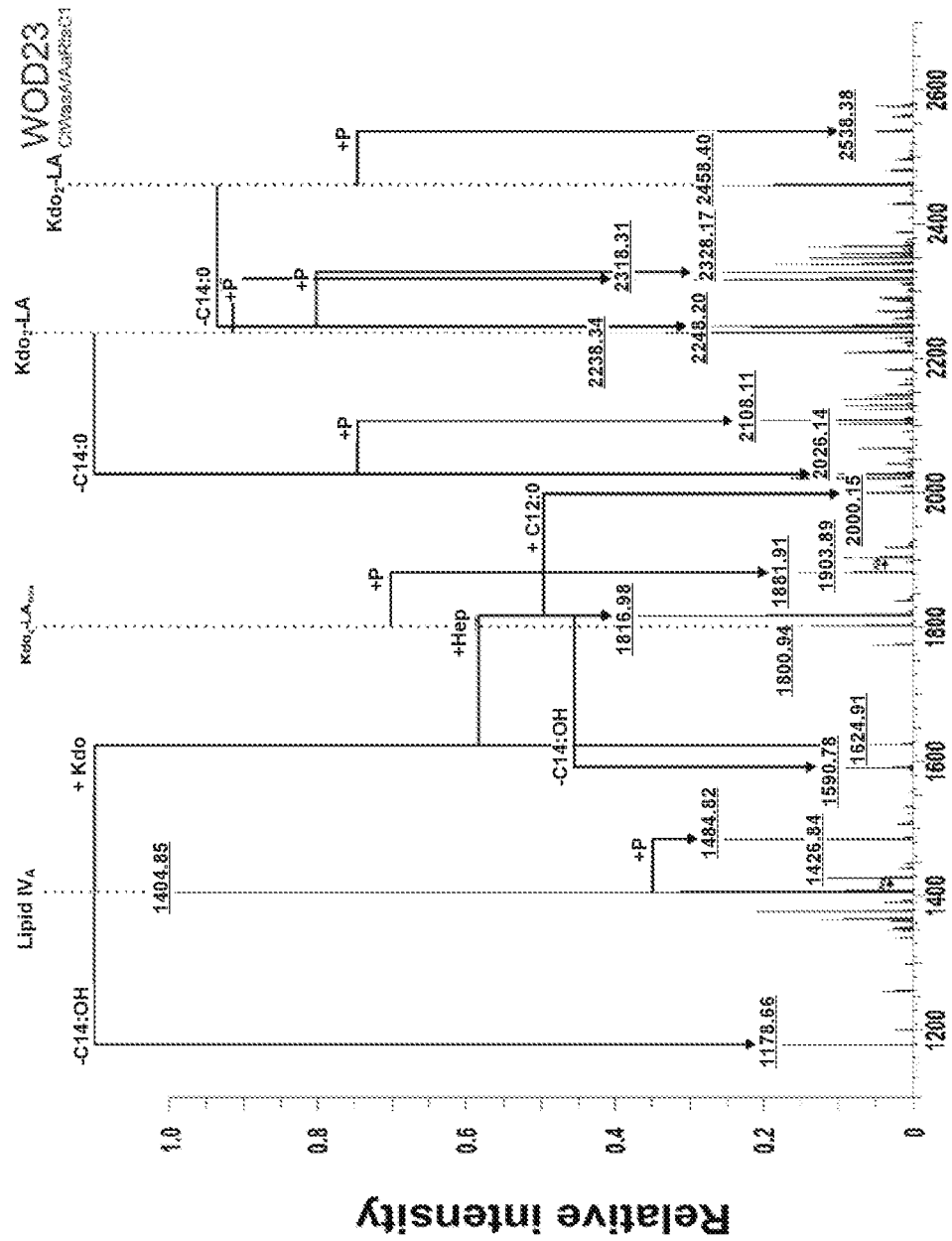
Figure 9L:
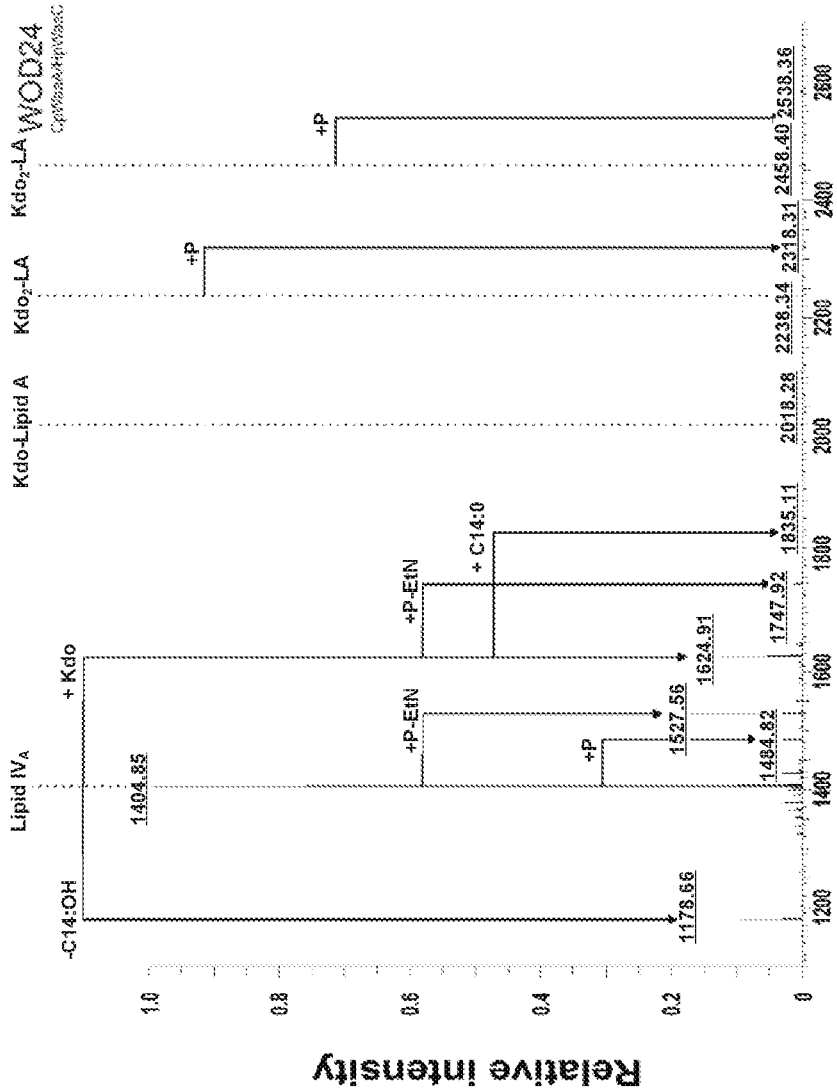
Figure 9M:
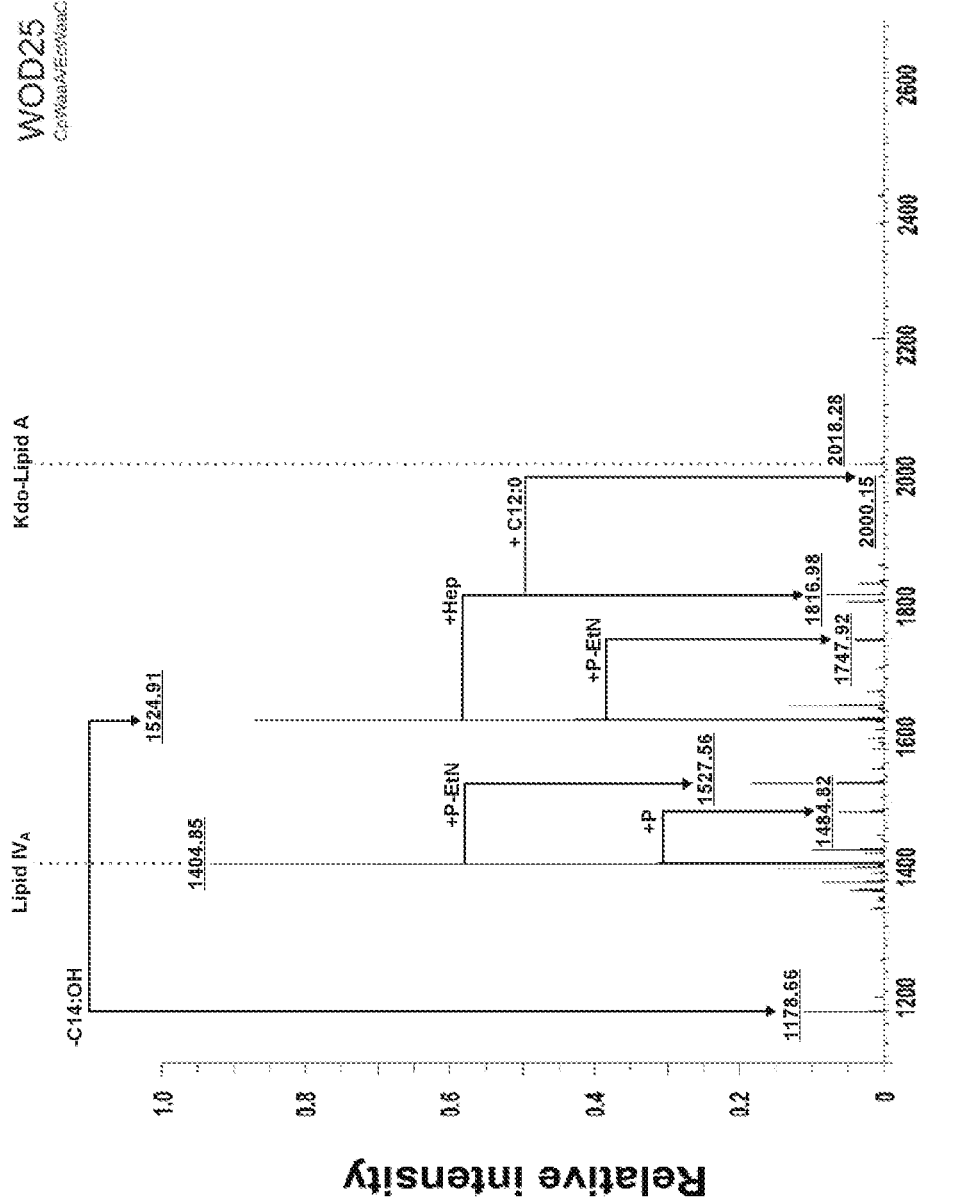
Figure 9N:
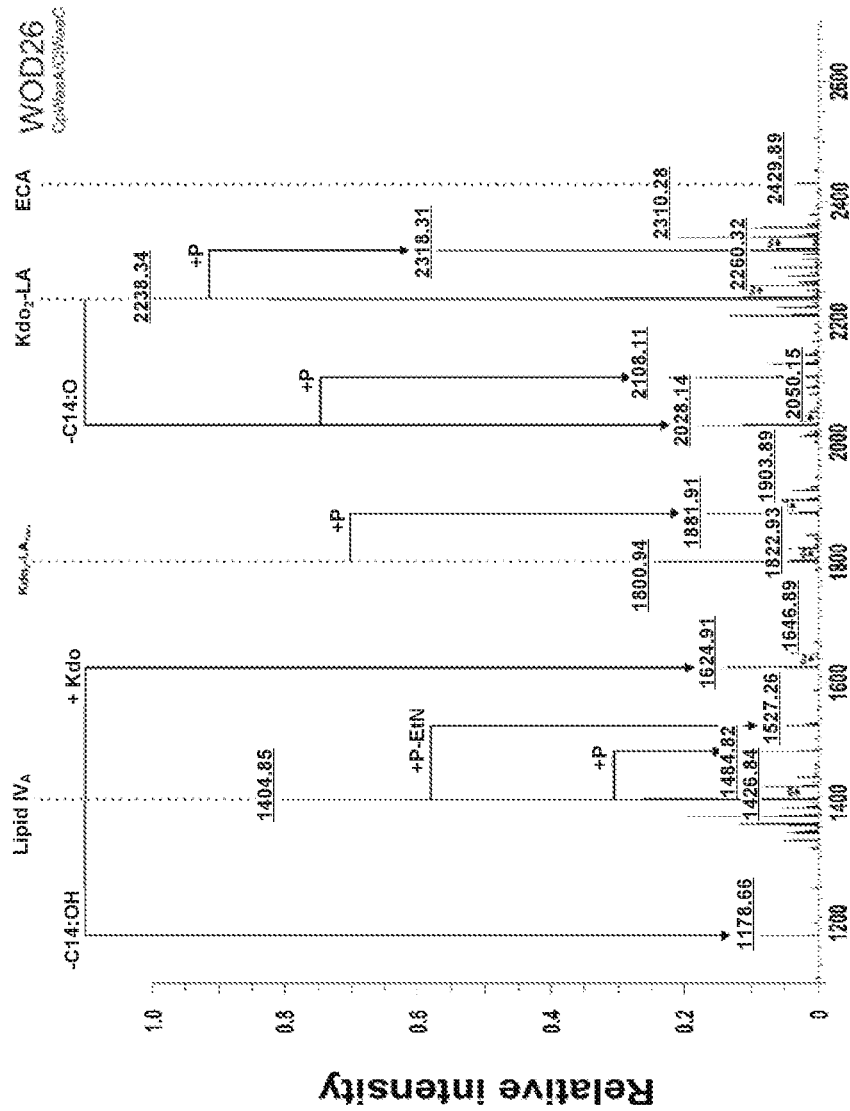
Figure 9O:
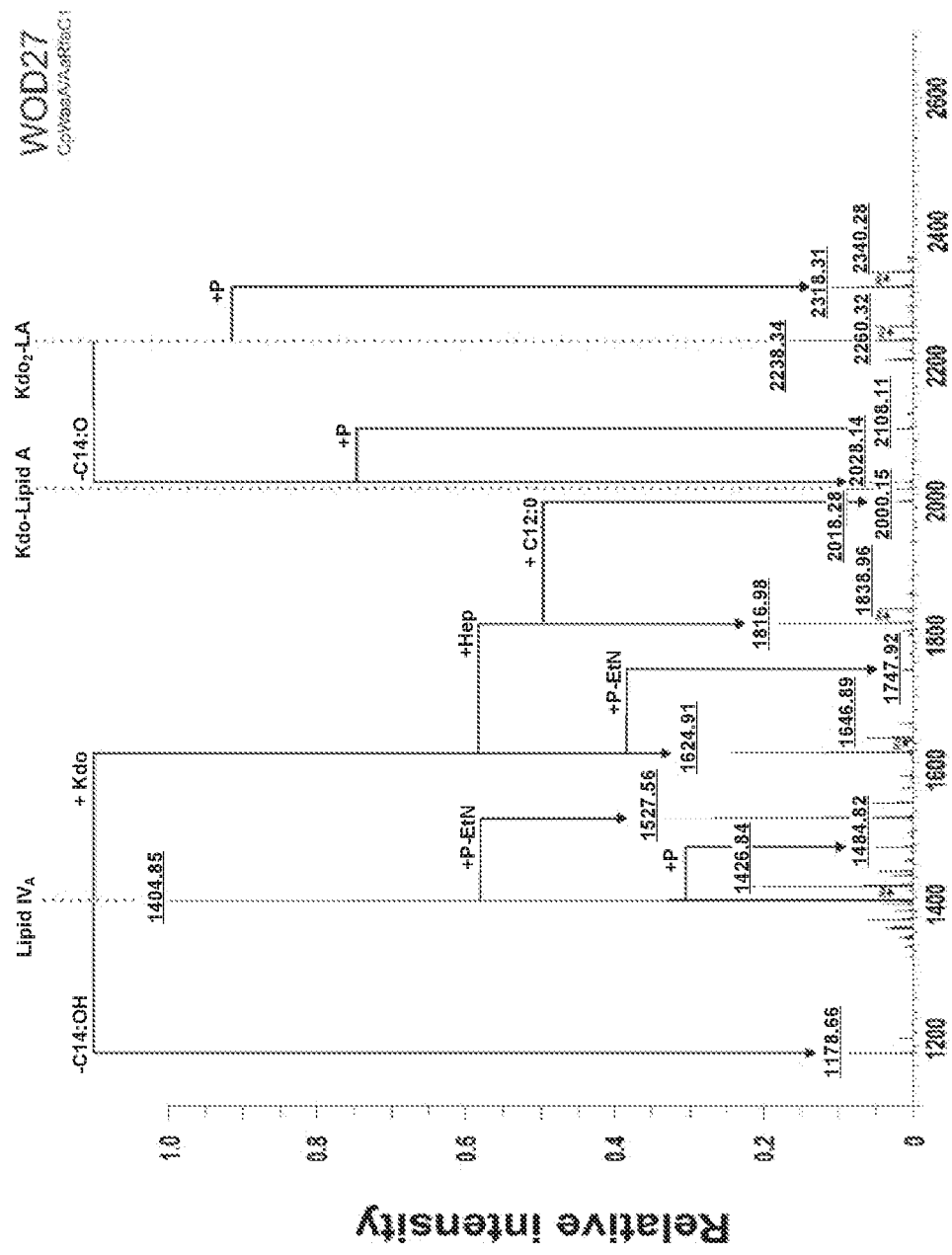

To facilitate an understanding of the present invention, a number of terms and phrases are defined below.

As used herein the terms "disease" and "pathologic condition" are used interchangeably, unless indicated otherwise herein, to describe a deviation from the condition regarded as normal or average for members of a species or group (e.g., humans), and which is detrimental to an affected individual under conditions that are not inimical to the majority of individuals of that species or group. Such a deviation can manifest as a state, signs, and/or symptoms (e.g., diarrhea, nausea, fever, pain, blisters, boils, rash, hyper-immune responses, hyper-sensitivity, immune suppression, inflammation, etc.) that are associated with any impairment of the normal state of a subject or of any of its organs or tissues that interrupts or modifies the performance of normal functions. A disease or pathological condition may be caused by or result from contact with a microorganism (e.g., a pathogen or other infective agent (e.g., a gram negative bacteria)), may be responsive to environmental factors (e.g., allergens, malnutrition, industrial hazards, and/or climate), may be responsive to an inherent defect of the organism (e.g., genetic anomalies) or to combinations of these and other factors.

The terms "host," "subject," "patient" and the like, as used herein, include, but are not limited to, mammals (e.g., murines, simians, equines, bovines, porcines, canines, felines, and the like), and most preferably includes humans. In the context of the invention, the term "subject" generally refers to an individual that will be administered or that has been administered one or more compositions of the present invention (e.g., a recombinant Gram negative bacteria of the invention and/or LPS (e.g., isolated and/or purified from) a Gram negative bacteria of the invention. Thus, a subject may be an individual administered an immunogenic composition (e.g., comprising LPS (e.g., isolated and/or purified from) from a recombinant Gram negative bacteria) of the invention. A subject may also be an individual that will be administered or that has been administered a recombinant Gram negative bacteria of the invention (e.g., to compete with or to populate the subject's microbiome).

The terms "buffer" or "buffering agents" refer to materials, that when added to a solution, cause the solution to resist changes in pH.

The terms "reducing agent" and "electron donor" refer to a material that donates electrons to a second material to reduce the oxidation state of one or more of the second material's atoms.

The term "monovalent salt" refers to any salt in which the metal (e.g., Na, K, or Li) has a net 1+ charge in solution (i.e., one more proton than electron).

The term "divalent salt" refers to any salt in which a metal (e.g., Mg, Ca, or Sr) has a net 2+ charge in solution.

The terms "chelator" or "chelating agent" refer to any materials having more than one atom with a lone pair of electrons that are available to bond to a metal ion.

The term "solution" refers to an aqueous or non-aqueous mixture.

As used herein, the term "a composition for inducing an immune response" refers to a composition that, once administered to a subject (e.g., once, twice, three times or more (e.g., separated by weeks, months or years)), stimulates, generates and/or elicits an immune response in the subject (e.g., resulting in total or partial immunity to a microorganism (e.g., pathogen (e.g., Gram negative bacteria)) capable of causing disease). In one embodiment of the invention, the composition comprises one or more antigens/immunogens together with LPS isolated and/or purified from a Gram negative bacteria of the invention. In a further embodiment, the composition comprising one or more antigens/immunogens and LPS is formulated for administration (e.g., via injectable route (e.g., intradermal, intramuscular, subcutaneously, etc.), mucosal route (e.g., nasally or vaginally), or other route) to a subject. In further preferred embodiments, the immunogenic composition comprises one or more other compounds or agents including, but not limited to, therapeutic agents, physiologically tolerable liquids, gels, carriers, diluents, adjuvants, excipients, salicylates, steroids, immunosuppressants, immunostimulants, antibodies, cytokines, antibiotics, binders, fillers, preservatives, stabilizing agents, emulsifiers, and/or buffers. An immune response may be an innate (e.g., a non-specific) immune response or a learned (e.g., acquired) immune response (e.g. that decreases the infectivity, morbidity, or onset of mortality in a subject (e.g., caused by exposure to a pathogenic microorganism) or that prevents infectivity, morbidity, or onset of mortality in a subject (e.g., caused by exposure to a pathogenic microorganism)). Thus, in some preferred embodiments, an immunogenic composition of the invention is administered to a subject as a vaccine (e.g., to prevent or attenuate a disease (e.g., allergic disease (e.g., by providing to the subject total or partial immunity against the disease or the total or partial attenuation (e.g., suppression) of a sign, symptom or condition of the disease))).

As used herein, the term "adjuvant" refers to any substance that can stimulate an immune response. Some adjuvants can cause activation of a cell of the immune system (e.g., an adjuvant can cause an immune cell to produce and secrete a cytokine). LPS isolated and/or purified from a Gram negative bacteria of the invention is an example of an adjuvant. Other examples include, but are not limited to, saponins purified from the bark of the Q. saponaria tree, such as QS21 (a glycolipid that elutes in the 21st peak with HPLC fractionation; Aquila Biopharmaceuticals, Inc., Worcester, Mass.);

poly(di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); emulsions (e.g., Freund's adjuvants), OM-174 (a glucosamine disaccharide related to lipid A; OM Pharma SA, Meyrin, Switzerland); and Leishmania elongation factor (a purified Leishmania protein; Corixa Corporation, Seattle, Wash.) as well as traditional adjuvants well known in the art (for example, aluminum phosphate or hydroxide salts ("alum")).

As used herein, the term "an amount effective to induce an immune response" (e.g., of a composition for inducing an immune response comprising LPS from a Gram negative bacteria of the invention), refers to the dosage level required (e.g., when administered to a subject) to stimulate, generate and/or elicit an immune response in the subject. An effective amount can be administered in one or more administrations (e.g., via the same or different route), applications or dosages and is not intended to be limited to a particular formulation or administration route. Accordingly, a "therapeutically effective amount" (e.g., of a composition for inducing an immune response) refers to the dosage level or amount of a composition required (e.g., when administered to a subject (e.g., administered via injection)) to stimulate, generate and/or elicit a therapeutic benefit in a subject. A therapeutically effective amount can be administered in one or more administrations (e.g., via the same or different route), applications or dosages and is not intended to be limited to a particular formulation or administration route.

As used herein, the term "under conditions such that said subject generates an immune response" and grammatical equivalents refer to any qualitative or quantitative induction, generation, and/or stimulation of an immune response (e.g., innate or acquired).

A used herein, the term "immune response" and grammatical equivalents refer to a response by the immune system of a subject. For example, immune responses include, but are not limited to, a detectable alteration (e.g., increase) in Toll-like receptor (TLR) activation, lymphokine (e.g., cytokine (e.g., Th1 or Th2 type cytokines) or chemokine) expression and/or secretion, macrophage activation, dendritic cell activation, T cell activation (e.g., CD4+ or CD8+ T cells), NK cell activation, and/or B cell activation (e.g., antibody generation and/or secretion). Additional examples of immune responses include binding of an immunogen (e.g., antigen (e.g., immunogenic polypeptide)) to an MHC molecule and inducing a cytotoxic T lymphocyte ("CTL") response, inducing a B cell response (e.g., antibody production), and/or T-helper lymphocyte response, and/or a delayed type hypersensitivity (DTH) response against the antigen from which an immunogenic polypeptide is derived, expansion (e.g., growth of a population of cells) of cells of the immune system (e.g., T cells, B cells (e.g., of any stage of development (e.g., plasma cells), and increased processing and presentation of antigen by antigen presenting cells. An immune response may be to antigens/immunogens that the subject's immune system recognizes as foreign (e.g., non-self antigens from microorganisms (e.g., pathogens), or self-antigens recognized as foreign). Thus, it is to be understood that, as used herein, "immune response" refers to any type of immune response, including, but not limited to, innate immune responses (e.g., activation of Toll receptor signaling cascade), cell-mediated immune responses (e.g., responses mediated by T cells (e.g., antigen-specific T cells) and non-specific cells of the immune system), and humoral immune responses (e.g., responses mediated by B cells (e.g., via generation and secretion of antibodies into the plasma, lymph, and/or tissue fluids). The term "immune response" is meant to encompass all aspects of the capability of a subject's immune system to respond to antigens and/or immunogens (e.g., both the initial response to an immunogen (e.g., a pathogen) as well as acquired (e.g., memory) responses that are a result of an adaptive immune response).

As used herein, the terms "toll receptors" and "TLRs" refer to a class of receptors (e.g., TLR1, TLR2, TLR3, TLR4, TLR5, TLR6, TLR7, TLR8, TLR9, TLRT0, TLR11) that recognize special patterns of pathogens, termed pathogen-associated molecular patterns (See, e.g., Janeway and Medzhitov, (2002) Annu. Rev. Immunol. 20, 197-216). These receptors are expressed in innate immune cells (e.g., neutrophils, monocytes, macrophages, dendritic cells) and in other types of cells such as endothelial cells. Their ligands include bacterial products such as LPS, peptidoglycans, and lipopeptides. TLRs are receptors that bind to exogenous ligands and mediate innate immune responses leading to the elimination of invading microbes. The TLR-triggered signaling pathway leads to activation of transcription factors including NFkB, which is important for the induced expression of proinflammatory cytokines and chemokines. TLRs also interact with each other. For example, TLR2 can form functional heterodimers with TLR1 or TLR6. The TLR2/1 dimer has different ligand binding profile than the TLR2/6 dimer (See, e.g., Ozinsky et al., 2000). Thus, methods described herein include adjuvant composition (e.g., composition comprising LPS isolated and/or purified from a Gram negative bacteria of the invention) optionally combined with one or more antigens/immunogens (e.g., protein antigens or other antigen described herein)) that when administered to a subject, activates one or more TLRs and stimulates an immune response (e.g., innate and/or adaptive/ acquired immune response) in a subject. Adjuvant may activate TLRs by, for example, interacting with TLRs (e.g., LPS binding to TLRs) or activating any downstream cellular pathway that occurs upon binding of a ligand (e.g., LPS) to a TLR. LPS isolated and/or purified from a Gram negative bacteria of the invention described herein that activate TLRs can also enhance the availability or accessibility of any endogenous or naturally occurring ligand of TLRs. LPS isolated and/or purified from a Gram negative bacteria of the invention that activates one or more TLRs can alter transcription of genes, increase translation of mRNA or increase the activity of proteins that are involved in mediating TLR cellular processes. For example, LPS isolated and/or purified from a Gram negative bacteria of the invention described herein that activate one or more TLRs can induce expression of one or more cytokines (e.g., Th1 and/or Th2 type cytokines).

As used herein, the term "immunity" refers to protection from disease (e.g., preventing or attenuating (e.g., suppression) of a sign, symptom or condition of the disease) upon exposure to a microorganism (e.g., pathogen) capable of causing the disease. Immunity can be innate (e.g., non-adaptive (e.g., non-acquired) immune responses that exist in the absence of a previous exposure to an antigen) and/or acquired/adaptive (e.g., immune responses that are mediated by B and T cells following a previous exposure to antigen (e.g., that exhibit increased specificity and reactivity to the antigen)).

As used herein, the terms "immunogen" and "antigen" are used interchangeably to refer to an agent (e.g., a microorganism (e.g., bacterium, virus or fungus) and/or portion or component thereof (e.g., protein, glycoprotein, lipoprotein, peptide, glycopeptide, lipopeptide, toxoid, carbohydrate, membrane fraction, etc.)) that is capable of eliciting an immune response in a subject. In preferred embodiments, immunogens elicit immunity against the immunogen (e.g., microorganism (e.g., pathogen or a pathogen product)) when administered in combination with LPS isolated and/or purified from a Gram negative bacteria of the invention.

As used herein, the term "pathogen product" refers to any component or product derived from a pathogen including, but not limited to, polypeptides, peptides, proteins, nucleic acids, membrane fractions, and polysaccharides.

As used herein, the term "enhanced immunity" refers to an increase in the level of adaptive and/or acquired immunity in a subject to a given immunogen (e.g., microorganism (e.g., pathogen)) following administration of a composition (e.g., composition for inducing an immune response of the present invention) relative to the level of adaptive and/or acquired immunity in a subject that has not been administered the composition (e.g., composition for inducing an immune response of the present invention).

As used herein, the terms "purified" or "to purify" refer to the removal of contaminants or undesired compounds from a sample or composition. As used herein, the term "substantially purified" refers to the removal of from about 70 to 90%, up to 100%, of the contaminants or undesired compounds from a sample or composition.

As used herein, the term "isolated" as in "isolated LPS" is intended to indicate a biological component no longer in its naturally occurring milieu. For example, "isolated LPS) is intended to indicate LPS which has been removed from its naturally occurring milieu (e.g., from Gram negative bacteria and/or free from Gram negative proteins, sugars, lipids and/or other components with which it would normally be found. The 'isolation" of a biological component (e.g., LPS), as used herein, requires no particular level of purification.

As used herein, the terms "administration" and "administering" refer to the act of giving a composition of the present invention (e.g., a composition for inducing an immune response) to a subject. Exemplary routes of administration to the human body include, but are not limited to, through the eyes (ophthalmic), mouth (oral), skin (transdermal), nose (nasal), lungs (inhalant), oral mucosa (buccal), ear, rectal, by injection (e.g., intravenously, subcutaneously, intraperitoneally, etc.), topically, and the like.

As used herein, the terms "co-administration" and "co-administering" refer to the administration of at least two agent(s) (e.g., LPS isolated and/or purified from a Gram negative bacteria of the invention and one or more other agents or therapies to a subject). In some embodiments, the co-administration of two or more agents or therapies is concurrent. In other embodiments, a first agent/therapy is administered prior to a second agent/therapy. In some embodiments, co-administration can be via the same or different route of administration. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s) (e.g., lowers the level of toxic immunostimulatory agent (e.g., LPS) needed to be administered to generate a desired immune response), and/or when co-administration of two or more agents results in sensitization of a subject to beneficial effects of one of the agents via co-administration of the other agent. In other embodiments, co-administration is preferable to elicit an immune response in a subject to two or more different immunogens (e.g., antigens) at or near the same time (e.g., when a subject is unlikely to be available for subsequent administration of a second, third, or more composition for inducing an immune response).

As used herein, the terms, "LPS related disorder", "condition associated with endotoxin", "endotoxin associated disorder", "endotoxin-related disorder", "sepsis", "sepsis related disorder", or similar terms, describes any condition associated with LPS, e.g., a condition associated with bacteremia or introduction of LPS into the blood stream or onto an extra-gastrointestinal mucosal surface (e.g., the lung). Such disorders include, but are not limited to, endotoxin-related shock, endotoxin-related disseminated intravascular coagulation, endotoxin-related anemia, endotoxin-related thrombocytopenia, endotoxin-related adult respiratory distress syndrome, endotoxin-related renal failure, endotoxin-related liver disease or hepatitis, systemic immune response syndrome (SIRS) resulting from Gram-negative infection, Gram-negative neonatal sepsis, Gram-negative meningitis, Gram-negative pneumonia, neutropenia and/or leucopenia resulting from Gram-negative infection, hemodynamic shock and endotoxin-related pyresis.

As used herein, the term, "recombinant Gram-negative bacteria" is used to refer to viable Gram-negative bacteria that have been genetically modified (e.g., to be deficient for one or more genes involved in LPS biosynthesis (e.g., lacking genes required for core oligosaccharide biosynthesis) and/or that have been genetically modified to contain one or more exogenous KDO transferase genes and/or one or more exogenous heptosyltransferase genes (e.g., from one or more types and/or strains of bacteria)).

The terms "cells" and "host cells" and "recombinant host cells", which are used interchangeably herein, refer to cells that are capable of or have been transformed with a vector, typically an expression vector. The host cells used herein are preferably Gram-negative bacteria. It is understood that such terms refer not only to the particular subject cell, but to the progeny or potential progeny of such a cell. Because certain modifications may occur in succeeding generations due to either mutation or environmental influences, such progeny may not, in fact, be identical to the parent cell, but are still included within the scope of the term as used herein.

The term "culture medium" is recognized in the art, and refers generally to any substance or preparation used for the cultivation of living cells.

The term "derived from," as used, for example, in the context of deriving LPS from a strain of Gram-negative bacteria, refers to LPS that can be obtained from the bacteria and is intended to include fragments or portions of LPS.

The term "defective" as used herein, with regard to a gene or gene expression, means that the gene is not a wildtype gene and that the organism does not have a wildtype genotype and/or a wildtype phenotype. The defective gene, genotype or phenotype may be the consequence of a mutation in that gene, or of a gene that regulates the expression of that gene (e.g., transcriptional or post-transcriptional), such that its normal expression is disrupted or extinguished. "Disrupted gene expression" is intended to include both complete inhibition and decreased gene expression (e.g., as in a leaky mutation), below wildtype gene expression.

The term "Gram-negative bacteria" is recognized in the art, and refers generally to bacteria that do not retain Gram stain (e.g., the deposition of a colored complex between crystal violet and iodine). In an exemplary Gram stain, cells are first fixed to a slide by heat and stained with a basic dye (e.g., crystal violet), which is taken up by all bacteria (i.e., both Gram-negative and Gram-positive). The slides are then treated with an iodine-KI mixture to fix the stain, washed with acetone or alcohol, and finally counterstained with a paler dye of different color (e.g., safranin). Gram-positive organisms retain the initial violet stain, while Gram-negative organisms are decolorized by the organic solvent and hence show the counterstain. Exemplary Gram-negative bacteria and cell lines include, but are not limited to, *Escherichia* spp., *Shigella* spp., *Salmonella* spp., *Campylobacter* spp., *Neisseria* spp., *Haemophilus* spp., *Aeromonas* spp., *Francisella* spp., *Yersinia* spp., *Klebsiella* spp., *Bordetella* spp., *Legionella* spp., *Corynebacteria* spp., *Citrobacter* spp., *Chlamydia* spp., *Brucella* spp., *Pseudomonas* spp., *Helicobacter* spp. and *Vibrio* spp.

As used herein, the term "portion" when used in reference to a sequence (e.g., an amino acid sequence of a protein, a nucleic acid sequence of a gene) represents any amount of the referenced sequence (e.g., 0.001%, 0.1%, 1%, 10%, 30%, 50%, 75%, 80%, 85%, 90%, 95%, 98%, 99.999% of an amino acid sequence or nucleic acid sequence).

The term "modulation" as used herein refers to both upregulation (i.e., activation or stimulation (e.g., by agonizing or potentiating)) and downregulation (i.e., inhibition or suppression (e.g., by antagonizing, decreasing or inhibiting)). The term "inducible" refers in particular to gene expression which is not constitutive but which takes place in response to a stimulus (e.g., temperature, heavy metals or other medium additive).

The term "non-human animals" includes any animal that can be treated or used in testing the present invention, including mammals such as non-human primates, rodents, sheep, dogs, cows, pigs, chickens, as well as amphibians, reptiles, etc. Preferred non-human animals are selected from the primate family or rodent family (e.g., rat and mouse).

The term "nucleic acid" refers to polynucleotides or oligonucleotides such as deoxyribonucleic acid (DNA), and, where appropriate, ribonucleic acid (RNA). The term should also be understood to include, as equivalents, analogs of either RNA or DNA made from nucleotide analogs and as applicable to the embodiment being described, single (sense or antisense) and double-stranded polynucleotides.

The term "pyrogenic" or "pyrogenicity" refers to the ability of a compound to induce fever or a febrile response when administered to a subject. Such febrile responses are generally mediated by the host proinflammatory cytokines IL-1, IL-6 and/or TNF-α, the secretion of which is induced, e.g., by LPS.

A substance having "reduced pyrogenicity" or a "reduced pyrogenic derivative" refers to a substance having less pyrogenic activity than the counterpart substance, e.g., less than about 80% pyrogenic relative to a counterpart substance, preferably less than about 70% pyrogenic, more preferably less than about 60% pyrogenic, more preferably less than about 50° pyrogenic, more preferably less than about 40% pyrogenic, and even more preferably less than about 30% pyrogenic. In other terms, a substance having reduced pyrogenicity is at least about 20%, 30%, 40%, 50%, 60%, or 70% less pyrogenic than the corresponding substance as determined by any of the assays described herein or known in the art.

"Substantially reduced pyrogenicity" or "substantially reduced pyrogenic derivative" refers to a substance (e.g., produced by viable non-toxic Gram-negative bacteria) which has been altered such that it has less than 20% pyrogenicity relative to the wildtype substance, preferably less than 10% pyrogenicity, preferably less than 1% pyrogenicity, preferably less than $10^{-1}$% pyrogenicity, preferably less than $10^{-2}$% pyrogenicity, preferably less than $10^{-3}$% pyrogenicity, preferably less than $10^{-4}$% pyrogenicity, preferably less than $10^{-5}$% pyrogenicity, and most preferably less than $10^{-6}$% pyrogenicity relative to the wildtype substance. In other terms, a substance that has substantially reduced pyrogenicity is at least about 90%, 99%, 10 fold, about $10^{-2}$ fold, about $10^{-3}$ fold, at least about $10^{-4}$ fold, at least about $10^{-5}$ fold, at least about $10^{-6}$ fold less pyrogenic relative to the corresponding unaltered substance as determined by any of the assays described herein or known in the art.

As used herein, the term "transfection" means the introduction of a nucleic acid (e.g., via an expression vector) into a recipient cell by nucleic acid-mediated gene transfer.

"Transformation", as used herein, refers to a process in which a cell's genotype is changed as a result of the cellular uptake of exogenous DNA or RNA. In an illustrative embodiment, a transformed cell is one that expresses a mutant form of one or more of the genes involved in LPS biosynthesis (e.g., lacking genes required for core oligosaccharide biosynthesis).

As used herein, the term "transgene" means a nucleic acid (e.g., a nucleic acid encoding a KDO transferase and/or a nucleic acid encoding a heptosyltransferase) that has been introduced into a cell. A transgene could be partly or entirely heterologous, i.e., foreign, to the transgenic animal or cell into which it is introduced, or, can be homologous to an endogenous gene of the organism or cell into which it is introduced, but which is designed to be inserted, or is inserted, into the animal or cell's genome in such a way as to alter the genome of the cell into which it is inserted. A transgene can also be present in a cell in the form of an episome.

The term "treating" a subject for a condition or disease, as used herein, is intended to encompass curing, as well as ameliorating at least one symptom of the condition or disease.

The term "vector" refers to a nucleic acid molecule, which is capable of transporting another nucleic acid to which it has been linked. Vectors capable of directing the expression of genes to which they are operatively linked are referred to herein as "expression vectors." The term "expression system" as used herein refers to an expression vector under conditions whereby an mRNA may be transcribed and/or an mRNA may be translated into protein, structural RNA, or other cellular component. The expression system may be an in vitro expression system, which is commercially available or readily made according to art known techniques, or may be an in vivo expression system, such as a eukaryotic or prokaryotic cell containing the expression vector. In general, expression vectors of utility in recombinant DNA techniques are often in the form of "plasmids" which refer generally to circular double stranded DNA loops that, in their vector form, are not bound to the chromosome. In the present specification, "plasmid" and "vector" are used interchangeably as the plasmid is the most commonly used form of vector. However, the invention is intended to include such other forms of expression vectors which serve equivalent functions and are well known in the art or which become known in the art subsequently hereto (e.g., cosmid, phagemid and bacteriophage vectors).

The terms "pharmaceutically acceptable" or "pharmacologically acceptable," as used herein, refer to compositions that do not substantially produce adverse reactions (e.g., toxic, allergic or immunological reactions) when administered to a subject.

As used herein, the term "pharmaceutically acceptable carrier" refers to any of the standard pharmaceutical carriers including, but not limited to, phosphate buffered saline solution, water, and various types of wetting agents (e.g., sodium lauryl sulfate), any and all solvents, dispersion media, coatings, sodium lauryl sulfate, isotonic and absorption delaying agents, disintrigrants (e.g., potato starch or sodium starch glycolate), polyethylethe glycol, and the like. The compositions also can include stabilizers and preservatives. Examples of carriers, stabilizers and adjuvants have been described and are known in the art (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a composition of the present invention that is physiologically tolerated in the target subject. "Salts" of the compositions of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compositions of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^{+'}$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compositions of the present invention are contemplated as being pharmaceutically acceptable. However, salts of acids and bases that are non-pharmaceutically acceptable may also find use, for example, in the preparation or purification of a pharmaceutically acceptable composition.

As used herein, the term "kit" refers to any delivery system for delivering materials. In the context of immunogenic agents (e.g., a composition comprising one or more antigens/immunogens together with LPS isolated and/or purified from a Gram negative bacteria of the invention), such delivery systems include systems that allow for the storage, transport, or delivery of immunogenic agents and/or supporting materials (e.g., written instructions for using the materials, a syringe and/or needle, etc.). For example, kits include one or more enclosures (e.g., boxes) containing the relevant immunogenic agents (e.g., LPS isolated and/or purified from a Gram negative bacteria of the invention) and/or supporting materials. As used herein, the term "fragmented kit" refers to delivery systems comprising two or more separate containers that each contain a sub-portion of the total kit components. The containers may be delivered to the intended recipient together or separately. For example, a first container may contain a composition comprising one or more antigens/immunogens together with LPS isolated and/or purified from a Gram negative bacteria of the invention for a particular use, while a second container contains a second agent (e.g., a syringe and/or needle). Indeed, any delivery system comprising two or more separate containers that each contains a sub-portion of the total kit components are included in the term "fragmented kit." In contrast, a "combined kit" refers to a delivery system containing all of the components of an immunogenic agent needed for a particular use in a single container (e.g., in a single box housing each of the desired components). The term "kit" includes both fragmented and combined kits.

DETAILED DESCRIPTION

The present invention provides novel, recombinant Gram-negative bacteria. In particular, the invention provides recombinant Gram-negative bacteria (e.g., *E. coli*) lacking genes involved in lipopolysaccharide (LPS, endotoxin) biosynthesis (e.g., lacking genes required for core oligosaccharide biosynthesis) and also provides recombinant Gram-negative bacteria lacking genes involved in LPS biosynthesis that contain one or more exogenous KDO transferases and/or one or more exogenous heptosyltransferases (e.g., from one or more types and/or strains of bacteria). The invention further provides methods of generating and utilizing (e.g., as or in an immunogenic composition (e.g., as or in an adjuvant and/or vaccine)) the recombinant Gram-negative bacteria in therapeutic, preventative, and/or research applications.

Lipid A (endotoxin), the hydrophobic anchor of lipopolysaccharide (LPS), is a glucosamine based phospholipid that makes up the outer monolayer of the outer membranes of most Gram negative bacteria. The minimal LPS required for the growth of *E. coli* consists of the lipid A and KDO (3-deoxy-D-manno-oct-2-ulosonic acid) domains. In wild-type strains, additional core and O-antigen sugars are present. These are generally not required for growth in the laboratory, but help bacteria resist antibiotics, the complement system, and other environmental stresses.

The unique eight carbon sugar 2-keto-3-deoxy-D-manno-octulosonic acid, KDO, is found in the majority of LPS glycoforms found in Gram-negative bacteria and serves to bridge the Lipid A portion with the core oligosaccharide. For wild-type *Escherichia coli* a minimal LPS structure, $KDO_2$-Lipid A or Re-LPS, is required for survivability of the cell line (See, e.g., Raetz, and Whitfield (2002) Ann Rev of Biochem 71, 635-700). The attachment of KDO is catalyzed from the activated sugar nucleotide CMP-KDO by the enzyme KDO transferase, WaaA or KdtA, which depending on the species can be mono-, bi-, tri-, or tetra-functional (See, e.g., Brabetz et al., (2000) J. Biol. Chem. 275, 34954-34962; Mamat et al., (2009) J. Biol Chem 284, 22248-22262; Belunis and Raetz, (1992), J Biol Chem 267, 9988-9997; Stead et al., (2005), J. Bacteriol. 187, 3374-3383; Noah et al., (2000) Journal of Endotoxin Research 7, 25-33; Heine et al., (2003) European Journal of Biochemistry 270, 440-450; Rund et al., (2000) European Journal of Biochemistry 267, 5717-5726), transferring either one, two, three, or four KDO molecules, respectively, to the tetra-acylated Lipid A precursor, Lipid $IV_a$.

The mechanism and selectivity by which multifunctional KDO transferases operate is currently unknown. Work by Chung and Raetz has shown that the functionality of KDO transferases can be changed by swapping a few amino acids between the KDO transferases of *Haemophilus influenzae* and *E. coli* showing that the functionality is enzyme specific rather than by some external factor. Additionally, the first crystal structure of a WaaA from *Aquifex aeolicus* co-crystallized with the substrate analog CMP was determined giving insight into the binding of substrate though the mechanism by which enzyme functionality is determined is as yet unknown.

After the addition of the KDO moieties in *E. coli*, the late acyltransferases, LpxL and LpxM, transfer the final fatty acids to the $KDO_2$-Lipid $IV_A$ giving the hexaacylated $KDO_2$-Lipid A. For some species this simple KDO glycosylated Lipid A is the complete LPS, such as with *Chlamydia trachomatis*, while most other species move on to further elaboration. In *E. coli* as in most enterobactericeae, the next step is the addition of the seven carbon sugar L-glycero-D-manno-heptose which is transferred by the heptosyltransferase I, WaaC with the pathway from Lipid $IV_A$ to the first heptosylation being shown in FIG. 1.

The inability to transfer this heptose in mutant *E. coli* strains leaves the cells with a deep-rough phenotype which causes increased susceptibility to hydrophobic antibiotics and increased susceptibility to phagocytosis by macrophages. This makes Lipid A biosynthesis and incorporation of these unusual sugars into LPS interesting targets for novel antibacterial development. Additionally, vaccines of the highly conserved inner core of some species such as *Neisseria meningitidis* have been under investigation as well as in the longstanding use for vaccine adjuvants. Studying the selectivity of the enzymes involved in core biosynthesis and having the ability to generate these inner core for further use often requires the growth of virulent, slow-growing bacteria, which has heretofore inhibited research and understanding of LPS, in particular its inner core.

As described in detail herein, experiments were conducted during development of embodiments of the invention in an effort to establish and characterize Gram-negative bacterial cells and cell lines lacking endogenous glycosyltransferases involved in core oligosaccharide biosynthesis within lipopolysaccharide (LPS). Furthermore, experiments were conducted during development of embodiments of the invention in an effort to establish and characterize Gram-negative bacterial cells and cell lines genetically modified to lack endogenous glycosyltransferases involved in core oligosaccharide biosynthesis within LPS and that also contain one or more exogenous KDO transferases and/or heptosyltransferases.

As shown in the Examples, Gram-negative bacterial cells and cell lines were generated that lacked endogenous glycosyltransferases involved in core oligosaccharide biosynthesis within LPS (See Examples 1-2). Furthermore, the recombinant Gram-negative bacterial cells lacking endogenous glycosyltransferases involved in core oligosaccharide biosynthesis within LPS were further and successfully modified to generate glycoforms of LPS using components (e.g., KDO transferases and/or heptosyltransferases) from a variety of Gram-negative bacteria (See Examples 3-4).

Accordingly, in one embodiment, the invention provides Gram-negative bacterial cells and/or cell lines deficient for glycosyltransferase (e.g., KDO transferase) enzymes (e.g., lacking 2 or more or all of waaF, waaC, waaL, waaU, waaZ, waaY, waaJ, waaR, waaB, waaS, waaP, waaG, waaQ, and waaA genes). Recombinant Gram-negative bacterial cells and cell lines of the invention are not limited by the number of KDO transferase enzymes for which they are deficient. For example, in one embodiment, the invention provides a Gram-negative bacterial cell and/or cell line that generates sugar precursors of core oligonucleotide biosynthesis but lacks the capability to transfer these sugars to the Lipid IV$_A$ molecule (e.g., due to deficiency of (e.g., genetic modification to remove) two, three, four, five, six, seven, eight, nine, ten, eleven, twelve, thirteen or all of the genes waaF, waaC, waaL, waaU, waaZ, waaY, waaJ, waaR, waaB, waaS, waaP, waaG, waaQ, and waaA encoding glycosyltransferase (e.g., KDO transferase) enzymes. While in a preferred embodiment the invention provides recombinant Gram-negative cells and/or cell lines in which the genes encoding glycosyltransferase (e.g., KDO transferase) enzymes are removed (e.g., genetically deleted), the invention is not so limited. For example, Gram-negative bacteria lacking glycosyltransferase (e.g., KDO transferase) enzymes may be generated by any mechanism. A variety of different mechanisms for generating such bacteria exist and may be used. That is, the present invention is not limited to gene mutation and/or genetic modification. In some embodiments, expression is altered using RNA interference or other techniques. In some embodiments, protein function is altered by providing inhibitors (e.g., synthetic or natural competitive or non-competitive ligands, antibodies, etc.). In some embodiments, modified bacteria are further supplied with nutrients, other modifications, or other components useful for maintaining health, growth, etc. in view of the alterations made to affect or alter glycosyltransferase (e.g., KDO transferase) enzyme activity.

In another embodiment, the invention provides Gram-negative bacterial cells and/or cell lines lacking/deficient for endogenous glycosyltransferases (e.g., that transfer sugar precursors of core oligonucleotide biosynthesis to the Lipid IV$_A$ molecule) that are further modified (e.g., genetically modified) to display inner and/or outer core oligosaccharides of a second, third, fourth or more Gram-negative bacteria (e.g., a specific Gram-negative bacterial cell (e.g., *E. coli*) is modified to lack endogenous glycosyltransferases and to display the appearance of other pathogenic Gram-negative bacteria (e.g., *H. influenzae, C. trachomatis, Chlamydophila psittaci, Helicobacter pylori, Campylobacter jejuni, Aquifex aeolicus*, or even a different *E. coli* strain)). Thus, in one embodiment, the invention provides recombinant Gram-negative bacterial cells and/or cell lines that generate and/or express inner core oligosaccharides not found in their wild type counterparts (See, e.g., Example s 1-3). For example, studying the selectivity of the enzymes involved in core biosynthesis and having the ability to generate inner core for further use often requires the growth of virulent, slow-growing bacteria. In order to develop a cell line capable of generating inner core oligosaccharides not found in wild type *E. coli*, the genes involved in core oligosaccharide biosynthesis were deleted using a unique mutant of *E. coli*, KPM56 (See, e.g., Mamat et al., (2009) J. Biol. Chem. 284, 22248-22262), which is capable of surviving with only Lipid IV$_A$ due to the presence of the phenotypic suppressor mutant in a gene of unknown function, yhjD400 (See, e.g., Mamat et al., (2008) Molecular Microbiology 67, 633-648). The recombinant Gram-negative cell line, WOD (waa operon deletion (e.g., described in the Examples)), can be modified (e.g., genetically) in order to be capable of biosynthesizing early inner core structure using KDO transferases and heptosyltransferases from a variety of Gram-negative bacteria. The invention is not limited by the type or source of KDO transferase or the type or source of heptosyltransferase used. Indeed, any KDO transferase or heptosyltransferases may be used in a construction scheme disclosed herein.

The invention is not limited by the type of Gram-negative bacteria utilized (e.g., for generation of recombinant bacterial cells and cell lines described herein). Indeed, the invention contemplates the use of any type of Gram-negative bacterial strain in the construction of Gram-negative bacterial cells and/or cell lines lacking/deficient for endogenous glycosyltransferases (e.g., that transfer sugar precursors of core oligonucleotide biosynthesis to the Lipid IV$_A$ molecule (e.g., that are optionally further modified (e.g., genetically modified) to display inner and/or outer core oligosaccharides of a second, third, fourth or more Gram-negative bacteria)). Examples of Gram-negative bacteria useful in the present invention include, but are not limited to, a bacteria from any one of the genera *Escherichia, Shigella., Salmonella, Campylobacter, Neisseria, Haemophilus, Aeromonas, Francisella, Yersinia, Klebsiella, Bordetella, Legionella, Corynebacteria, Citrobacter, Chlamydia, Brucella, Pseudomonas, Helicobacter,* and *Vibrio*. In a preferred embodiment, *E. coli* is used.

The invention contemplates the use of any technique for introducing genetic mutations within Gram-negative bacteria. Such techniques include, but are not limited to, non-specific mutagenesis, using chemical agents such as N-methyl-N'-nitro N-nitrosoguanidine, acridine orange, ethidium bromide, or non-lethal exposure to ultraviolet light (see, e.g., Miller (Ed.), 1991, In: A Short Course in Bacterial Genetics, Cold Spring Harbor Press, Cold Spring Harbor, N.Y.; herein incorporated by reference in its entirety). In a preferred embodiment, the mutation is a specific mutation made using recombinant genetic techniques. In another embodiment, the mutations can be introduced using Tn10 mutagenesis, bacteriophage-mediated transduction, lambda phage-mediated allelic exchange, or conjugational transfer, or site directed mutagenesis using recombinant DNA techniques (see, e.g., Miller (Ed.), 1991, supra; Hone, et al., 1987, J. Infect. Dis., 156:167; Noriega, et al, 1994, Infect. Immun., 62:5168; Hone, et al., 1991, Vaccine, 9:810; Chatfield, et al., 1992, Vaccine, 10:53; Pickard, et al., 1994, Infect. Immun., 62:3984; Odegaard, et al., 1997, J. Biol. Chem., 272:19688; Lee, et al., 1995, J. Biol. Chem., 270: 27151; Garrett, et al., 1998, J. Biol. Chem., 273:12457; each herein incorporated by reference in their entireties).

In some embodiments, mutations within Gram-negative bacteria are either constitutively expressed or under the control of inducible promoters, such as, for example, the temperature sensitive heat shock family of promoters, or the anaerobically-induced nirB promoter (see, e.g., Harborne, et al., 1992, Mol. Micro., 6:2805; herein incorporated by reference in its entirety) or repressible promoters, such as uapA (see, e.g., Gorfinkiel, et al., 1993, J. Biol. Chem., 268:23376; herein incorporated by reference in its entirety) or gcv (see, e.g., Stauffer, et al., 1994, J. Bact, 176:6159; herein incorporated by reference in its entirety). Selection of an appropriate promoter may depend on the host bacterial strain and will be obvious to those skilled in the art.

In some embodiments, the invention provides non-toxic (e.g., endotoxin free (e.g., due to a deficiency of endogenous glycosyltransferases (e.g., that transfer sugar precursors of core oligonucleotide biosynthesis to the Lipid IV$_A$ molecule)) Gram-negative bacteria (e.g., *E. coli*). The present invention is not limited to a particular method of providing non-toxic Gram-negative bacteria.

In some embodiments, the non-toxic Gram-negative bacteria is genetically engineered via cloning methods known to those skilled in the art (See, e.g., Sambrook et al., Molecular Cloning; A Laboratory Manual, Cold Spring Harbor Laboratory Press; incorporated herein by reference in its entirety) to express, produce and display non-native proteins and peptides such as, but not limited to, LPS or LPS components from other bacterial organisms, unique lipid derivatives, human protein or peptide production, non-human protein or peptide production, vaccine production, and the like. Such products produced find utility in a variety of applications, including but not limited to, clinical therapeutics and basic research applications (e.g., described herein).

The invention is not limited by or to any particular use of the Gram negative cells, cell lines, and/or components thereof (e.g., protein, glycoprotein, lipoprotein, peptide, glycopeptide, lipopeptide, toxoid, carbohydrate, membrane fraction, etc.) of the invention. Indeed, as described herein recombinant negative cells, cell lines, and/or components thereof (e.g., protein, glycoprotein, lipoprotein, peptide, glycopeptide, lipopeptide, toxoid, carbohydrate, membrane fraction, etc.) of the invention find a variety of uses and applications. In one embodiment, Gram-negative bacterial cells and/or cell lines (e.g., that are lacking and/or deficient for endogenous glycosyltransferases (e.g., KDO transferases and/or heptosyltransferases) and that express one or more exogenous KDO transferases and/or heptosyltransferases (e.g., thereby displaying inner and/or outer core oligosaccharides of a different second, third, fourth and/or more Gram-negative bacteria)) and/or components thereof of the invention are used to identify, determine, characterize, and/or refine the substrate specificity of a glycosyltransferase. In another embodiment, Gram negative cells, cell lines, and/or components thereof (e.g., protein, glycoprotein, lipoprotein, peptide, glycopeptide, lipopeptide, toxoid, carbohydrate, membrane fraction, etc.) of the invention are used to identify, determine, characterize, and/or elucidate one or mechanisms by which a glycosyltransferase operates (e.g., glycosyltransferase biologically activity, mechanism of action, and/or pathway sequence properties). In yet another embodiment, Gram negative cells, cell lines, and/or components thereof (e.g., protein, glycoprotein, lipoprotein, peptide, glycopeptide, lipopeptide, toxoid, carbohydrate, membrane fraction, etc.) of the invention are used to identify, determine, characterize, and/or elucidate new glycosyl backbone modifications (e.g., new/unique peripheral glycosyl backbone modifications). In another embodiment, Gram negative cells, cell lines, and/or components thereof (e.g., protein, glycoprotein, lipoprotein, peptide, glycopeptide, lipopeptide, toxoid, carbohydrate, membrane fraction, etc.) of the invention are used to identify, determine, characterize, and/or elucidate how Gram negative cells behave (e.g., react) in various stress conditions. In another embodiment, Gram negative cells, cell lines, and/or components thereof (e.g., protein, glycoprotein, lipoprotein, peptide, glycopeptide, lipopeptide, toxoid, carbohydrate, membrane fraction, etc.) of the invention are used to identify, determine, characterize, and/or elucidate the behavior and/or biological activity of the Gram negative cells, cell lines, and/or components thereof (e.g., recombinant techniques and cells and/or cell lines of the invention may be used to display pathogenic lipo-oligosaccharide in a non-virulent cell line and its biological properties identified, determined, and/or characterized). In another embodiment, Gram negative cells, cell lines, and/or components thereof (e.g., protein, glycoprotein, lipoprotein, peptide, glycopeptide, lipopeptide, toxoid, carbohydrate, membrane fraction, etc.) of the invention are used to identify and/or characterize Gram negative outer membrane structures. In still another embodiment, Gram negative cells, cell lines, and/or components thereof (e.g., protein, glycoprotein, lipoprotein, peptide, glycopeptide, lipopeptide, toxoid, carbohydrate, membrane fraction, etc.) of the invention are used to identify, characterize, or otherwise determine the permeability small molecules (e.g., into and/or out of Gram negative bacteria and/or host cells).

In some embodiments, the invention provides one or more components of LPS(e.g., Lipid IVa, O-antigen, KDO, etc.) isolated and/or purified from Gram-negative bacterial cells and/or cell lines lacking/deficient for endogenous glycosyltransferases (e.g., that transfer sugar precursors of core oligonucleotide biosynthesis to the Lipid $IV_A$ molecule) that are further modified (e.g., genetically modified) to display inner and/or outer core oligosaccharides of a second, third, fourth or more Gram-negative bacteria. The invention is not limited by the way in which a component of LPS is so isolated and/or purified. For example, current methods for isolating lipid IVa involve traditional total organic synthesis, degradation of mature LPS, or purification from conditional mutants that elaborate a heterogeneous LPS layer that contains a fraction of the desired lipid IVa.

In some embodiments, the present invention provides outer membrane vesicles isolated and/or purified from Gram-negative bacterial cells and/or cell lines lacking/deficient for endogenous glycosyltransferases (e.g., that transfer sugar precursors of core oligonucleotide biosynthesis to the Lipid $IV_A$ molecule) that are further modified (e.g., genetically modified) to display inner and/or outer core oligosaccharides of a second, third, fourth or more Gram-negative bacteria. In some embodiments, isolated outer membrane vesicles are used to treat, or prophylactically prevent, sepsis related disorders. In some embodiments, outer membrane vesicles of the invention are used for or in an immunogenic composition (e.g., an adjuvant or a vaccine).

In some embodiments, Gram-negative bacterial cells and/or cell lines of the invention (e.g., lacking/deficient for endogenous glycosyltransferases (e.g., that transfer sugar precursors of core oligonucleotide biosynthesis to the Lipid $IV_A$ molecule) that are optionally further modified (e.g., genetically modified) to display inner and/or outer core oligosaccharides of a second, third, fourth or more Gram-negative bacteria) are used as hosts for the production of endotoxin free therapeutic molecules. The present invention is not limited to particular therapeutic molecules. Production of therapeutic molecules in Gram-negative bacteria, whether it be outer membrane vesicles for vaccines, LPS type molecules (such as monophosphoryl lipid A (MPLA)) to be used as adjuvants, recombinant pharmaceutical proteins, macromolecules, or DNA for mammalian cell transfection/gene therapy, can be plagued by the presence of endotoxin from the bacterial host. Contamination of the therapeutic molecule with endotoxin is a concern, as the immunogenic potential of LPS is well documented. Current production strategies to alleviate endotoxin contamination include various purification techniques, such as the kits marketed for endotoxin free DNA plasmid purification, followed by assays to measure endotoxin levels. As the Gram-negative bacterial cells and/or cell lines of the invention do not produce endotoxin, such purification steps are not required. Accordingly, Gram-negative bacterial cells and/or cell lines of the invention provide improved methods of isolating endotoxin free therapeutic molecules (e.g., lipid IVa).

In some embodiments, Gram-negative bacterial cells and/or cell lines of the invention are used for production of immunogenic compositions (e.g., vaccines) used to stimulate immune responses. For example, cells of the invention and components thereof may be used to generate vaccines and other compositions for inducing immune responses that are free of endotoxin contamination or that contain LPS or components thereof of multiple bacterial species. For example, attenuated or OM vaccines can be prepared using procedures as described in US Patent Application 2005/0013831 or U.S. Pat. No. 6,558,677, incorporated herein by reference in their entireties. Vaccines may find use in immunizing subjects at risk of acquiring septic shock (e.g., from *E. coli*), such as surgery patients. Further, endotoxin free attenuated or OM vaccines can be developed for immunization against, for example, whooping cough (e.g., *Bordetella* sp.), brucellosis or endotoxic shock (e.g., *Brucella* sp.), pulmonary and respiratory infections (e.g., *Pseudomonas* sp., *Haemophilus* sp., *Moraxella* sp.), cholera (e.g., *Vibrio* sp.), pneumonia (e.g., *Klebsiella* sp., *Haemophilus* sp.), stomach ulcers (e.g., *Helicobacter* sp.), meningitis (e.g., *Neisseria* sp., *Haemophilus* sp.), otitis media (e.g., *Haemophilus* sp., *Moraxella* sp.), dysentery and diarrhea (e.g., *Shigella* sp., *E. coli, Vibrio* sp., *Campylobacter* sp., *Yersenia* sp.), enteric fevers (e.g., *Salmonella* sp.), trachoma and sexually transmitted diseases (e.g., *Chlamydia* sp.), tularemia (e.g., *Franciscella* sp.), and plague (e.g., *Yersinia* sp.).

In a preferred embodiment, Gram-negative bacterial cells and/or cell lines of the invention and/or components thereof (e.g., LPS isolated and/or purified therefrom) are used in an immunogenic composition (e.g., to form a vaccine).

A vaccine preparation of the present invention may be used to protect or treat a mammal susceptible to infection, by means of administering the vaccine via systemic or mucosal route. These administrations may include injection via the intramuscular, intraperitoneal, intradermal or subcutaneous routes; or via mucosal administration to the oral/alimentary, respiratory, genitourinary tracts. Although a vaccine of the invention may be administered as a single dose, components thereof may also be co-administered together at the same time or at different times (for instance, wild type or genetically modified LPS could be administered separately, at the same time or 1-2 weeks after the administration of any Gram-negative bacterial antigen component of the vaccine for optimal coordination of the immune responses with respect to each other. In addition to a single route of administration, 2 different routes of administration may be used. For example, polysaccharides may be administered IM (or ID) and proteins may be administered IN. In addition, a vaccines may be administered IM for priming doses and IN for booster doses, or, may be administered IN for priming doses and IM for booster doses.

Vaccine preparation is generally described in Vaccine Design ("The subunit and adjuvant approach" (eds Powell M. F. & Newman M. J.) (1995) Plenum Press New York).

In some embodiments, vaccines are stored in solution or lyophilized. If lyophilized, preferably the solution is lyophilized in the presence of a sugar such as sucrose, trehalose or lactose. It is still further preferable that they are lyophilized and extemporaneously reconstituted prior to use. Lyophilizing may result in a more stable composition (vaccine) and may possibly lead to higher antibody titers.

Antibodies and Passive Immunization. Another aspect of the invention is a method of preparing an immune globulin for use in prevention or treatment of infection and/or disease caused by Gram-negative bacteria comprising the steps of immunizing a recipient with a vaccine (e.g., comprising vaccine components described herein) and isolating immune globulin from the recipient. An immune globulin prepared by this method is a further aspect of the invention. A pharmaceutical composition comprising the immune globulin of the invention and a pharmaceutically acceptable carrier is a further aspect of the invention which could be used in the manufacture of a medicament for the treatment or prevention of infection and/or disease caused by Gram-negative bacteria. A method for treatment or prevention of infection and/or disease caused by Gram-negative bacteria comprising a step of administering to a patient an effective amount of the pharmaceutical preparation containing immune globulin and/or antibodies of the invention is a further aspect of the invention.

Inocula for polyclonal antibody production are typically prepared by dispersing the immunogenic composition (e.g., an immunogenic composition described herein) in a physiologically tolerable diluent such as saline or other adjuvants suitable for human use to form an aqueous composition. An immunostimulatory amount of inoculum is administered to a mammal and the inoculated mammal is then maintained for a time sufficient for the antigenic composition to induce protective antibodies.

The antibodies can be isolated to the extent desired by well-known techniques such as affinity chromatography (Harlow and Lane Antibodies; a laboratory manual 1988).

Antibodies can include antiserum preparations from a variety of commonly used animals e.g. goats, primates, donkeys, swine, horses, guinea pigs, rats or man. The animals are bled and serum recovered.

An immune globulin produced in accordance with the present invention can include whole antibodies, antibody fragments or subfragments. Antibodies can be whole immunoglobulins of any class e.g. IgG, IgM, IgA, IgD or IgE, chimeric antibodies or hybrid antibodies with dual specificity to two or more antigens of the invention. They may also be fragments e.g. F(ab')2, Fab', Fab, Fv and the like including hybrid fragments. An immune globulin also includes natural, synthetic or genetically engineered proteins that act like an antibody by binding to specific antigens to form a complex.

A vaccine of the present invention can be administered to a recipient who then acts as a source of immune globulin, produced in response to challenge from the specific vaccine. A subject thus treated would donate plasma from which hyperimmune globulin would be obtained via conventional plasma fractionation methodology. The hyperimmune globulin would be administered to another subject in order to impart resistance against or treat infection and/or disease caused by Gram-negative bacteria. Hyperimmune globulins of the invention are particularly useful for treatment or prevention of infection and/or disease caused by Gram-negative bacteria in infants, immune compromised individuals or where treatment is required and there is no time for the individual to produce antibodies in response to vaccination.

An additional aspect of the invention is a pharmaceutical composition comprising two of more monoclonal antibodies (or fragments thereof; preferably human or humanized) reactive against at least two constituents of an immunogenic composition of the invention, which could be used to treat or prevent infection and/or disease caused by Gram-negative bacteria.

Such pharmaceutical compositions comprise monoclonal antibodies that can be whole immunoglobulins of any class e.g. IgG, IgM, IgA, IgD or IgE, chimeric antibodies or hybrid antibodies with specificity to two or more antigens of the invention. They may also be fragments e.g. F(ab')2, Fab', Fab, Fv and the like including hybrid fragments.

Methods of making monoclonal antibodies are well known in the art and can include the fusion of splenocytes with myeloma cells (Kohler and Milstein 1975 Nature 256; 495; Antibodies—a laboratory manual Harlow and Lane 1988). Alternatively, monoclonal Fv fragments can be obtained by screening a suitable phage display library (Vaughan T J et al 1998 Nature Biotechnology 16; 535). Monoclonal antibodies may be humanized or part humanized by known methods.

Immunogenic compositions of the present invention described herein may be used to protect or treat a mammal (e.g., a human) susceptible to infection, by means of administering the immunogenic composition via systemic or mucosal route. These administrations may include injection via the intramuscular, intraperitoneal, intradermal or subcutaneous routes; or via mucosal administration to the oral/alimentary, respiratory, genitourinary tracts.

As described herein, the invention provides methods of preventing and/or treating infection and/or disease caused by Gram-negative bacteria comprising administering an effective amount of an immunogenic composition of the invention to a subject. For example, the invention provides the use of an immunogenic composition of the invention for the manufacture of a medicament (e.g., a vaccine) for the treatment of infection and/or disease caused by Gram-negative bacteria. For example, in some embodiments, methods of treating subjects protects the subject against Gram-negative bacteria colonization (e.g., prevents a subject administered the immunogenic composition against infection and disease caused by Gram-negative bacteria and/or eliminates carriage of Gram-negative bacteria in subjects administered the immunogenic composition (e.g., thereby providing herd immunity and/or eliminating a species of Gram-negative bacteria from a population of subjects)). While an understanding of a mechanism of action is not needed to practice the present invention, and while the present invention is not limited to any particular mechanism of action, in one embodiment, administration of an immunogenic composition of the invention confers systemic and mucosal immunity and protects against colonization and transmission of a Gram-negative bacteria. The invention is not limited by the type of subject administered an immunogenic composition of the invention. Indeed, any subject that can be administered an effective amount of an immunogenic composition of the invention (e.g., to induce an immune response specific to a specific Gram-negative bacteria in the subject) is contemplated to benefits from the immunogenic compositions of the invention. In one embodiment, the subject is an adult (e.g., of child bearing age). In one embodiment, the adult is a parent, a grandparent or other adult (e.g., a teacher, a daycare provider, a health care professional, or other adult) that is physically around and exposed to children on a daily basis. In one embodiment, the subject is not an adult (e.g., is a child) but is physically around and exposed to other non-adults/children on a daily basis.

In one embodiment, immunization with an immunogenic composition of the invention reduces and/or prevents carriage of a Gram-negative bacteria and reduces and/or prevents transmission of the Gram-negative bacteria.

In some embodiments of the invention, the compositions of the invention are administered to a subject who is at risk of or likely to experience Gram-negative bacteria exposure, or who is known or likely to have been or exposed, but has not yet developed infection. However, in other embodiments, the composition is administered to individuals who have already developed an infection, in order to curtail the extent of infection in the individual and hasten recovery, and/or to prevent transmission to others.

A further preferred embodiment of the invention is a use of the immunogenic composition of the invention in the manufacture of a vaccine for treatment or prevention of Gram-negative bacterial infection or disease.

The invention is further described by reference to the following examples, which are provided for illustration only. The invention is not limited to the examples, but rather includes all variations that are evident from the teachings provided herein. All publicly available documents referenced herein, including but not limited to U.S. patents are specifically incorporated by reference.

EXAMPLES

The following examples serve to illustrate certain preferred embodiments and aspects of the present invention and are not to be construed as limiting the scope of the invention in any way.

Example 1

Construction of Chromosomal Deletion of LPS Core Oligosaccharide Biosynthesis

Materials and Methods.

Bacterial Strains, Plasmids, and Growth Conditions. All strains and plasmids used are described in FIG. 6. Standard cultures of *E. coli* were routinely grown aerobically with shaking (250 rpm) at 37° C. in LB medium (10 g/liter Bacto-tryptone, 5 g/liter yeast extract, 10 g/liter NaCl). When necessary, kanamycin (30 µg/ml), chloramphenicol (30 µg/ml), or ampicillin (100 µg/ml), was added to the media.

DNA Methods. Standard recombinant DNA methods were used for nucleic acid preparation and analysis (See, e.g., Sambrook, J., and Russell, D. W. (2001) *Molecular Cloning: A Laboratory Manual*, 3rd Edition, Cold Spring Harbor Laboratory Press, Cold Spring Harbor, N.Y.). Primer sequences are also provided in FIG. 6. To construct gene deletions, the phage λ Red recombinase procedure of Datsenko and Wanner was used (See, e.g., Datsenko and Wanner (2000), *PNAS* 97, 6640-6645) as described, except plasmids pKD46 and pCP20 were cured at 37° C. to accommodate the temperature sensitive phenotype of lipid $IV_A$-expressing *E. coli* derivatives. For generation of a cell line lacking all genes involved in core oligosaccharide biosynthesis, WaaFfor and WaaArev were used to generate the KAN resistance cassette from pKD4 which targeted the gene region from the nucleotides 3794929-3809817 which includes the genes waaF, waaC, waaL, waaU, waaZ, waaY, waaJ, waaR, waaB, waaS, waaP, waaG, waaQ, and waaA within three separate operons. Transformation of this linear cassette into KPM56/pKD46 generated the kanamycin-resistant strain, WOD (waa operon deletion) 01. Removal of the kanamycin resistance gene by curing with pCP20 generated the strain WOD02.

To clone the heptosyltransferases, WaaC from *Helicobacter pylori* (HpwaaC) (jhp_0264), WaaC from *Escherichia coli* (EcwaaC) (b3621), WaaC from *Campylobacter jejuni* (CjwaaC) (cj1133), and WaaC from *Aquifex aeolicus* (AarfaC1) (aq 1542) from *H. pylori* J99, *E. coli* K-12 MG1655, *C. jejuni* Strain NCTC 11168, and *A. aeolicus* VF5, respectively, into pET26b and the KDO transferases WaaA from *Haemophilus influenzae* (HiwaaA), WaaA from *Escherichia coli* (EcwaaA) (b3633), WaaA from *Chlamydia trachomatis* (CtwaaA), and WaaA from *Chlamydophila psittaci* (CpwaaA) from *H. influenzae* 169, *E. coli* K-12 MG1655, *C. trachomatis* L2, and *C. psittaci* 6BC, respectively, into pETduet1, the appropriate primers were chosen. For the heptosyltransferases the appropriate genomic DNAs were used as templates, while for the KDO transferases pUM211, pUM212, pFEN207, or pUM210 were used as the appropriate templates. The heptosyltransferases were subcloned into the multiple cloning site of pET26b using the restriction sites for NdeI and BamHI while the KDO transferases were subcloned into pETduet1 using the restriction sites NdeI and XhoI. In order to use pETduet1 to coexpress both a heptosyltransferase and a KDO transferase each of the four pETduet1 plasmids containing each KDO transferase gene were cut with XbaI and BamHI removing the promoter and ribosomal binding site of the empty multiple cloning site. The pET26b plasmids containing the heptosyltransferases were similarly restricted giving a fragment carrying the promoter region, ribosomal binding site, and heptosyltransferase gene. These fragments were subcloned into the KDO transferase containing pETduet1 or a similarly digested empty pETduet1 plasmid giving a total of 24 pETduet1 plasmids generated. These plasmids underwent DNA sequencing to verify sequences of the desired genes. Each pETduet1 plasmid were transformed into WOD02 by electroporation.

Cell growth for LPS Production. Transformed cells were grown on LB agar plates supplemented with 100 μg/mL ampicillin. A 2 mL culture of liquid LB medium, also supplemented with ampicillin, was inoculated from single colonies at 37° C. overnight with shaking at 200 rpm. This culture was diluted 1:100 in 200 mL fresh LB medium and incubated at 37° C., 200 rpm overnight. Cells were then sedimented by centrifugation at 4000×g, 4° C., 30 min (Eppendorf Centrifuge 5804R). The resulting pellet was resuspended in 30 mL of phosphate buffered saline before being recentrifuged. The cells were then resuspended in 20 mL of ethanol and stirred at 4° C. overnight. Cells were once again centrifuged before being resuspended in 20 mL of acetone which was left at 4° C. stirring for 2 h. This process of centrifuging, resuspending in acetone, and stirring was repeated once more. The suspension was centrifuged a final time. To the resulting biomass was added a small volume of diethyl ether to make a slurry which was subjected to filtration by indirect vacuum. The biomass was left to dry overnight and then pulverized to a homogenous fine particulate.

LPS purification. LPS samples were purified by a modified version of the phenol-chloroform-petroleum ether procedure (See, e.g., Galanos et al., (1969) Eur J Biochem 9, 245-249; Mamat et al., (2008) Molecular Microbiology 67, 633-648). Samples were resuspended into LPS-free water (Braun water) to a concentration of 1 mg/mL for mass spectrometry analysis and TLR4 activation assays.

Electrospray-Ionization Fourier-transformed Ion Cyclotron Mass Spectrometry. LPS samples (1 mg/ml) were diluted 15-fold in a solution consisting of 50% 2-propanol supplemented with 4 mM triethylamine and 0.35 mM acetic acid resulting in a pH of approx. 8.5. All samples were analyzed in the negative ion mode using a Q Exactive Plus instrument (Thermo, Bremen, Germany) with Electrospray Ionization (ESI). Samples were delivered with a syringe pump at a flow rate of 5 uL/min using a sheath gas flow of 5 L/min, transfer capillary temperature of 250 C and a S-lens level of 100. Spectra were recorded at highest resolution (280,000 FWHM defined at m/z 200) with no further collisional activation or all ion fragmentation activated with NCE set to 25V.

TLR4 stimulation assays. Using the diluted LPS samples, TLR4 activation was assayed using the HEK-BLUE™ hTLR4 and HEK-BLUE™ Null2 cells in accordance with the specifications of the supplier of the cell lines (INVIVOGEN) (See, e.g., Mamat et al., (2015), Microb Cell Fact 14.

Example 2

Construction of Chromosomal Deletion of LPS Core Oligosaccharide Biosynthesis—KDO and Heptosyltransferases Plasmid Construction Construction of chromosomal deletion of LPS core oligosaccharide biosynthesis. Experiments were conducted in an effort to generate cells capable of synthesizing inner core oligosaccharides not found in wild type *E. coli*. The cell line KPM56 was chosen for the construction of an *E. coli* mutant lacking the genes involved in core oligosaccharide biosynthesis based on its ability, as well as that of its progenitor KPM22(See, e.g., Meredith et al., (2006) *ACS chemical biology* 1, 33-42), to survive chromosomal deletions of genes required for LPS biosynthesis (e.g., KdsD, GutQ, WaaA, and WaaC). Additionally, unlike in many species of Gram-negative bacteria, *E. coli* K-12 MG1655 contains all genes in core oligosaccharide biosynthesis in a single gene cluster (See FIG. 7, and See Roncero and Casadaban, (1992) J. Bacteriol. 174, 3250-3260) thereby facilitating removal in this cell line. In total, 14 genes (including waaA and waaC) were removed by the Datsenko-Wanner method from this gene cluster. hldD, the gene encoding ADP-L-glycero-D-mannoheptose epimerase, and coaD, the gene encoding panthethine-phosphate adenylyltransferase, were left intact as confirmed by DNA sequencing of this region. The resulting cell line, WOD02, was capable of generating the appropriate sugar precursors of core biosynthesis, but lacked the capability to transfer these sugars to the Lipid $IV_A$ molecule. Unlike the KPM56 progenitor, the WOD02 cells formed highly mucoid colonies on standard LB-miller agar plates. This mucoid morphology may be attributed to colonic acid production due to lack of WaaL (See, e.g., Meredith et al., (2007) J. Biol. Chem. 282, 7790-7798).

Example 3

WOD02 is Capable of Expressing Non-Native Inner Core

In order to characterize and test the functionality of the WOD02 cell line, KDO transferases and heptosyltransferases from various Gram-negative species were identified and tested for expression and function in the cell line (e.g., in order to generate various glycoforms using these functional components from other Gram-negative bacteria). In particular, it was tested whether different KDO transferases (e.g., representing mono-, bi-, tri-, and tetrafunctional KDO transferases) could be expressed and function within the cell line. Experiments were performed in order to characterize the number of Kdo glycosylation events catalyzed by the WaaA of various Gram-negative bacteria and toward probing the substrate specificities of WaaC, the next enzyme in the biosynthetic pathway of a number of diverse microorganisms. For example, one would assume that a WaaC from an organism that displays two Kdos would not glycosylate a mono-Kdo glycosylated Lipid A species since no such species have been observed in their native organism. This approach, therefore, was used to determine if a microorganism in which WaaC normally glycosylates a single Kdo-Lipid A would transfer a heptose to a di- or tri-Kdo glycosylated species. Novel, as well as natural, LPS molecules may be generated via these experiments.

Experiments were first conducted in order to introduce a WaaA from an organism observed to have mono-, bi-, tri-, or tetrafunctional activity with *H. influenzae* (See, e.g., Brabetz et al., (2000) *J. Biol. Chem.* 275, 34954-34962), *E. coli* (See, e.g., Belunis and Raetz, (1992) *J Biol Chem* 267, 9988-9997), *C. trachomatis* (See, e.g., Heine et al., (2003) European Journal of Biochemistry 270, 440-450), and *Chlamydophila psittaci* (See Rund (2000) *European Journal of Biochemistry* 267, 5717-5726) respectively chosen to represent each group, and analysis of the number of Kdos displayed in the cell line assessed.

In order to create a matrix as well as to probe substrate specificities, four different WaaCs were co-expressed in tandem with the WaaA in each of the above stains containing the various Kdo derivatives. The heptosyltransferases were chosen based on predicted specificity and possible enhanced promiscuity. Results from the various combinations and permutations are shown FIG. 3 and FIG. 4 and are further described below.

In order to test and to determine the ability of WOD02 cells to generate glycoforms from other Gram-negative bacteria, the LPS of WOD02 was purified and analyzed by electrospray ionization Fourier transform ion cyclotron mass spectrometry in negative ion mode. Cell lines lacking the waa gene cluster were unable to glycosylate LPS thereby displaying major peaks of 1404.85 u and 1527.86 u for only Lipid IV$_A$ (1,4'-bisphosphorylated tetraacylated Lipid A, calculated mass 1404.854 u) and the phosphoethanolamine (P-EtN) modified Lipid IV$_A$ (calculated mass 1527.862 u), respectively, similar to the LPS found in the cell lines KPM22 (See, e.g., Meredith et al., (2006), *ACS chemical biology* 1, 33-4) and KPM56 (See, e.g., Mamat et al., (2009) *J Biol Chem* 284, 22248-22262).

The cell lines WOD03 (Empty Vector), WOD08 (HpWaaC), WOD09 (EcWaaC), WOD10 (CjWaaC), and WOD11 (AaRfaC1), all of which lack KDO transferases, displayed a similar production of Lipid IV$_A$ and P-EtN-Lipid IV$_A$ which indicated that neither the vector alone nor any of the heptosyltransferases were able to cause modification of the truncated LPS.

WOD02 cells heterologously expressing KDO transferases, namely WOD04 (HiWaaA), WOD05 (EcWaaA), WOD06 (CtWaaA) and WOD07 (CpWaaA), each displayed a restored ability to transfer KDO to Lipid IV$_A$. WOD04, WOD05, WOD06, and WOD07 all displayed a peak of 1624.91 u representing a single KDO to Lipid IV$_A$ (KDO-Lipid IV$_A$, calculated mass 1624.912 u). Additionally, WOD04, WOD05, and WOD06 each displayed an M+1 peak, 2018.28 u, for the fully acylated KDO-Lipid IV$_A$, KDO-Lipid A (calculated mass 2017.277 u). WOD05 and WOD06 displayed an M+1 peak at 2238.34 u which corresponded to KDO$_2$-Lipid A (calculated mass 2237.336 u). WOD06 also displayed the presence of the triglycosylated KDO$_3$-Lipid A (M+1 exact mass 2458.40 u, calculated mass 2457.39 u). Surprisingly, although CpWaaA had previously been shown to have tetrafunctional KDO transferase activity (See, e.g., Brabetz et al., (2000) Eur J Biochem 267, 5458-5465), no samples tested were observed to contain the peak for KDO$_4$-Lipid A (calculated mass 2677.45 u).

Other KDO transferase activities were more readily seen in other samples, namely, the presence of KDO$_3$-Lipid A in WOD17 (EcWaaA and EcWaaC) and the presence of KDO$_2$-Lipid A in WOD24 (CpWaaA and HpWaaC), WOD26 (CpWaaA and CjWaaC), and WOD27 (CpWaaA and AaRfaC1) and KDO$_3$-Lipid A in WOD24. A summary of the activities of the KDO transferases tested and characterized are shown in FIG. 5. In general, it was determined that the heterologous expression of KDO transferases in the WOD02 cell line permitted the generation of mono-, bi-, or trifunctionalized LPS glycologs/analogs.

In order to further modify these initial glycosylated strains, the Kdo transferases were coexpressed with putative heptosyltransferase I enzymes from various species. The WaaC of *Helicobacter pylori* was used because while the Kdo transferase is bifunctional giving two Kdo moieties attached to the Lipid IV$_A$, the distal Kdo is removed by a Kdo hydrolase. This modification is believed to help H. pylori evade the host immune system (See, e.g., Stead et al., (2005) *J. Bacteriol.* 187, 3374-3383). Due to the presence of both Kdo-Lipid IV$_A$ and Kdo$_2$-Lipid IV$_A$ it was postulated that the heptosyltransferase I of *H. pylori* may have enhanced promiscuity. The heptosyltransferase I from *E. coli* was chosen both as a control (e.g., due to it being the best characterized heptosyltransferase I to date) as well as being the only WaaC structure to have been determined (See, e.g., Grizot et al., (2006) *Journal of molecular biology* 363, 383-394). *E. coli* WaaC is also known to transfer a heptose to Kdo$_2$-Lipid A, Kdo$_3$-Lipid A (See, e.g., Gronow et al., (2009) *Innate Immun* 15, 13-23) or a fully deacylated Lipid A analog (See, e.g., Czyzyk et al., (2011) *Biochemistry* 50, 10570-10572). The third heptosyltransferase I chosen was from the *Campylobacter jejuni* whose truncated LPS has been seen to have been composed of Hep-Kdo-Lipid A (See, e.g., Naito et al., (2010) *J. Bacteriol.* 192, 2182-2192) or Hep-Kdo$_2$-Lipid A (See Cullen et al., (2013) *Infect Immun* 81, 430-440) leading to the possibility of enhanced WaaC promiscuity. The last enzymes chosen were RfaC1 (gene: aq_1543) and RfaC2 (gene: aq_145) from the hyperthermophilic *Aquifex aeolicus* as a putative heptosyltransferases. Both genes in *A. aeolicus* are annotated as ADP-heptose: LPS heptosyltransferases. Although the structure of full LPS of *A. aeolicus* is unknown, analysis of the LPS from the related species, *A. pyrophilus*, gave evidence for the presence of two heptose molecules in the LPS core (See, e.g., Plotz et al., (2000) *J. Biol. Chem.* 275, 11222-11228). It is therefore conceivable that *A. aeolicus* rfaC1 and rfaC2 encode not for two heptosyltransferase I enzymes but instead one being a heptosyltransferase I and the other a heptosyltransferase II. The Kdo transferase of *A. aeolicus* is known to transfer only a single Kdo (See, e.g., Mamat et al. (2010) *The Journal of biological chemistry* 284, 22248-22262), and as such it was speculated that the heptosyltransferase I of *A. aeolicus* will only transfer to a single Kdo. Using the aforementioned Kdo transferases coexpressed with HpWaaC yielded heptose modification as follows.

WOD12 (HiWaaA and HpWaaC) and WOD24 displayed the presence of Hep-KDO-Lipid IV$_A$ (exact mass 1816.98 u, calculated mass 1816.975 u). WOD20 (CtWaaA and HpWaaC) displayed the presence of Hep-KDO$_2$-Lipid A (M+1 exact mass 2430.40 u, calculated mass 2429.399 u).

For EcWaaC, the presence of Hep-KDO-Lipid IV$_A$ was observed in WOD13 (HiWaaA and EcWaaC), WOD17 (EcWaaA and EcWaaC), and WOD25 (CpWaaA and EcWaaC). WOD17 and WOD21 (CtWaaA and EcWaaC) both displayed the presence of Hep-KDO$_2$-Lipid A. WOD21 also displayed the presence of the larger Hep-KDO$_3$-Lipid A (M+1 exact mass 2650.46 u, calculated mass 2649.458 u).

CjWaaC was observed to generate Hep-KDO-Lipid IV$_A$ in WOD26, or Hep-KDO$_2$-Lipid A in WOD22 (EcWaaA and CjWaaC).

In contrast, AaRfaC1 displayed the least promiscuity generating only Hep-KDO-Lipid IV$_A$ in WOD15 (HiWaaA and AaRfaC1), WOD19 (EcWaaA and AaRfaC1), WOD23 (CtWaaA and AaRfaC1), and WOD27. A summary of the activities of the heptosyltransferases used in the above experiments are shown in FIG. 3 and FIG. 4. Thus, as described above and in FIGS. 3 and 4, the invention provides that it was possible to generate Hep-Kdo-Lipid IV$_A$, Hep-Kdo$_2$-Lipid A, and Hep-Kdo$_3$-Lipid A in vivo using the WOD02 cell line described herein.

Example 4

WOD02 Displays a Putative 3'-O-Deacylase Activity

LPS samples from a number of the KDO transferase and heptosyltransferase expressing WOD02 cell lines contained peaks which correspond to KDO$_2$-LA$_{Tetra}$ (exact mass 1800.94 u, calculated mass 1800.944 u), which is the 3'-O-deacylated KDO$_2$-Lipid A wherein the 3'-acyloxylacyl moiety has been removed. This peak was observed in all of the tested EcWaaA expressing cell lines (WOD05, WOD17, WOD18, and WOD19), in all CtWaaA expressing cell lines (WOD06, WOD20, WOD21, WOD22, and WOD23), as well as in two of the CtWaaA expressing cell lines (WOD26 and WOD27). Additionally, a peak corresponding to the heptosylated KDO$_2$-LA$_{Tetra}$, Hep-KDO$_2$-LA$_{Tetra}$ (M+1 exact mass 1994.01 u, calculated mass 1993.007 u) was observed in three samples (WOD17, WOD20, and WOD21). KDO$_2$-LA$_{Tetra}$ has previously been reported (See, e.g., Zahringer et al., (2001) *Journal of Endotoxin Research* 7, 133-146) in the mutant *E. coli* F515 which is known to be deficient in heptosyltransferase activity giving KDO$_2$-Lipid A as a maximal LPS structure (See, e.g., Schmidt et al., (1970) Eur J Biochem 16, 382-392).

Endotoxicity. In order to test and verify the lack of endotoxic product in the WOD02 cell line as well as to show the ability to return endotoxicity with the addition of KDO transferases, TLR4/MD-2 activation was assayed by subjecting HEK-BLUE™ hTLR4 and HEK-BLUE™ Null2 cells to purified LPS samples. With HEK-BLUE™ Null2 being the parent strain of HEK-BLUE™ hTLR4 lacking the TLR4, MD-12, and CD14 needed to elicit the NF-κB mediated response. Activation of the TLR4 complex by LPS induces production of the reporter protein, secreted embryonic alkaline phosphatase (SEAP). The phosphatase activity was measured using a colorimetric substrate with an absorbance reading at 655 nm. Percent activation was determined based on the highest reading of the *E. coli* K-12 LPS at 1000 ng/mL.

Activation of hTLR4 for LPS samples purified from WOD03 which lacks all glycosyltransferases for core region biosynthesis was observed to be the lowest of all samples tested with lower than 2% activity compared to full *E. coli* K-12 LPS at the same concentration (See FIG. 3). It was also observed that the addition of KDO transferases helped to return hTLR4 activation to these cells. The addition of only a single KDO (seen in WOD04) returned a low hTLR4 activation while the other cell lines displayed a higher return of hTLR4 activation. A comparison each KDO transferase with each heptosyltransferase indicated that in general, the addition of a heptosyltransferase for EcWaaA, CtWaaA, and to a lesser extent CpWaaA, appeared to have little to no difference on the overall hTLR4 activation (See FIGS. 5B-5E).

The cell lines containing HiWaaA on the other hand appeared to vary more widely based on heptosyltransferase. While the change in activation was quite clear, the underlying reason for this is not currently known (e.g., while an understanding of the mechanism of action is not needed to practice the present invention, and while the present invention is not limited to any particular mechanism of action, in some embodiments, the changes in activation are due to a change in overall lipid yield, and/or activation of late acyltransferases). Regardless, the present invention provides that the LPS produced in the WOD cell line background has very low hTLR4 activation when compared to wild type *E. coli* LPS, and that in general, the addition of a KDO transferase allows a return of hTLR4 activation of the purified LPS from these cells.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

---

What is claimed is:

1. A recombinant *E. coli* cell lacking all endogenous glycosyltransferases involved in the biosynthesis of the core oligosaccharide within lipopolysaccharide (LPS), wherein the cell comprises an exogenous KDO transferase.

2. The recombinant *E. coli* cell of claim 1, wherein the cell lacks endogenous waaF, waaC, waaL, waaU, waaZ, waaY, waaJ, waaR, waaB, waaS, waaP, waaG, waaQ, and waaA genes.

3. The recombinant *E. coli* cell of claim 1, wherein the cell possesses endogenous hldD and coaD genes.

4. The recombinant *E. coli* cell of claim 1, wherein the cell generates sugar precursors of core oligonucleotide biosynthesis but lacks the capability to transfer the sugar precursors to the Lipid $IV_A$ molecule.

5. The recombinant *E. coli* cell of claim 1, wherein the exogenous KDO transferase is from *H. influenzae*.

6. The recombinant *E. coli* cell of claim 1, wherein the KDO transferase is from *C. trachomatis*.

7. The recombinant *E. coli* cell of claim 1, wherein the KDO transferase is from *Chlamydophila psittaci*.

8. The recombinant *E. coli* cell of claim 1, further comprising an exogenous heptosyltransferase.

9. The recombinant *E. coli* cell of claim 8, wherein the heptosyltransferase is from *Helicobacter pylori*.

10. The recombinant *E. coli* cell of claim 8, wherein the heptosyltransferase is from *Campylobacter jejuni*.

11. The recombinant *E. coli* cell of claim 8, wherein the heptosyltransferase is from *Aquifex aeolicus*.

12. A recombinant *E. coli* cell lacking all endogenous glycosyltransferases involved in the biosynthesis of the core oligosaccharide within lipopolysaccharide (LPS), wherein the cell comprises one or more exogenous KDO transferases.

13. The recombinant *E. coli* cell of claim 12, further comprising one or more exogenous heptosyltransferases.

* * * * *

SEQUENCE LISTING

```
<160> NUMBER OF SEQ ID NOS: 20

<210> SEQ ID NO 1
<211> LENGTH: 43
<212> TYPE: DNA
<213> ORGANISM: Artificial sequence
<220> FEATURE:
<223> OTHER INFORMATION: synthetic

<400> SEQUENCE: 1
gattctagaa ttcatatgaa aatagcgatt gtcaggcttt cag              43

<210> SEQ ID NO 2
<211> LENGTH: 44
```

<212> TYPE: DNA
<213> ORGANISM: Artificial sequence
<220> FEATURE:
<223> OTHER INFORMATION: synthetic

<400> SEQUENCE: 2
gaattcggat cctcattctt tttcctttaa aacgtttaaa acgc    44

<210> SEQ ID NO 3
<211> LENGTH: 38
<212> TYPE: DNA
<213> ORGANISM: Artificial sequence
<220> FEATURE:
<223> OTHER INFORMATION: synthetic

<400> SEQUENCE: 3
gattctagaa ttcatatgcg ggttttgatc gttaaaac    38

<210> SEQ ID NO 4
<211> LENGTH: 42
<212> TYPE: DNA
<213> ORGANISM: Artificial sequence
<220> FEATURE:
<223> OTHER INFORMATION: synthetic

<400> SEQUENCE: 4
gaattcggat ccttataatg atgataactt ttccaaaact gc    42

<210> SEQ ID NO 5
<211> LENGTH: 42
<212> TYPE: DNA
<213> ORGANISM: Artificial sequence
<220> FEATURE:
<223> OTHER INFORMATION: synthetic

<400> SEQUENCE: 5
tatacatatg atcttttttt attatttttt aacttggacg gc    42

<210> SEQ ID NO 6
<211> LENGTH: 38
<212> TYPE: DNA
<213> ORGANISM: Artificial sequence
<220> FEATURE:
<223> OTHER INFORMATION: synthetic

<400> SEQUENCE: 6
atatggatcc ttataagctt tttcttgcat caattccc    38

<210> SEQ ID NO 7
<211> LENGTH: 39
<212> TYPE: DNA
<213> ORGANISM: Artificial sequence
<220> FEATURE:
<223> OTHER INFORMATION: synthetic

<400> SEQUENCE: 7
gattctagaa ttcatatgaa gaaggcgtta atagtgagg    39

<210> SEQ ID NO 8
<211> LENGTH: 41
<212> TYPE: DNA
<213> ORGANISM: Artificial sequence
<220> FEATURE:
<223> OTHER INFORMATION: synthetic

<400> SEQUENCE: 8
gaattcggat ccttacggct tggtattcaa aatgtttata g                    41

<210> SEQ ID NO 9
<211> LENGTH: 36
<212> TYPE: DNA
<213> ORGANISM: Artificial sequence
<220> FEATURE:
<223> OTHER INFORMATION: synthetic

<400> SEQUENCE: 9
atatatatca tatgtggcgt tttttttata ccagct                          36

<210> SEQ ID NO 10
<211> LENGTH: 34
<212> TYPE: DNA
<213> ORGANISM: Artificial sequence
<220> FEATURE:
<223> OTHER INFORMATION: synthetic

<400> SEQUENCE: 10
atatctcgag tcatacattg cgctccaaat aagg                            34

<210> SEQ ID NO 11
<211> LENGTH: 29
<212> TYPE: DNA
<213> ORGANISM: Artificial sequence
<220> FEATURE:
<223> OTHER INFORMATION: synthetic

<400> SEQUENCE: 11
actccatatg ctcgaattgc tttacaccg                                  29

<210> SEQ ID NO 12
<211> LENGTH: 29
<212> TYPE: DNA
<213> ORGANISM: Artificial sequence
<220> FEATURE:
<223> OTHER INFORMATION: synthetic

<400> SEQUENCE: 12
cagtctcgag tcaatgcgtt ttcggtggc                                  29

<210> SEQ ID NO 13
<211> LENGTH: 41
<212> TYPE: DNA
<213> ORGANISM: Artificial sequence
<220> FEATURE:
<223> OTHER INFORMATION: synthetic

<400> SEQUENCE: 13
gattctagaa ttcatatgat aagacgttgg ttaacatctc g                    41

<210> SEQ ID NO 14
<211> LENGTH: 40
<212> TYPE: DNA
<213> ORGANISM: Artificial sequence
<220> FEATURE:
<223> OTHER INFORMATION: synthetic

<400> SEQUENCE: 14
gaattcctcg agttagattt tcatgcaagt aatttggctc                      40

<210> SEQ ID NO 15
<211> LENGTH: 28
<212> TYPE: DNA
<213> ORGANISM: Artificial sequence

```
<220> FEATURE:
<223> OTHER INFORMATION: synthetic

<400> SEQUENCE: 15
actgcatatg gtggggcttc ctaggatt                                              28

<210> SEQ ID NO 16
<211> LENGTH: 45
<212> TYPE: DNA
<213> ORGANISM: Artificial sequence
<220> FEATURE:
<223> OTHER INFORMATION: synthetic

<400> SEQUENCE: 16
cactctcgag ctatattttt acacaaggga tatatctttt aaaag                           45

<210> SEQ ID NO 17
<211> LENGTH: 70
<212> TYPE: DNA
<213> ORGANISM: Artificial sequence
<220> FEATURE:
<223> OTHER INFORMATION: synthetic

<400> SEQUENCE: 17
gtgtaacgga atacatggcc tggctgaatc gcgacgcata agagctctgc gtgtaggctg           60
gagctgcttc                                                                  70

<210> SEQ ID NO 18
<211> LENGTH: 70
<212> TYPE: DNA
<213> ORGANISM: Artificial sequence
<220> FEATURE:
<223> OTHER INFORMATION: synthetic

<400> SEQUENCE: 18
taatgggatc gaaagtaccc ggataaatcg cccgtttttg cataacaacc catatgaata           60
tcctccttag                                                                  70

<210> SEQ ID NO 19
<211> LENGTH: 22
<212> TYPE: DNA
<213> ORGANISM: Artificial sequence
<220> FEATURE:
<223> OTHER INFORMATION: synthetic

<400> SEQUENCE: 19
ccgttcaaaa ccgttgctga ag                                                    22

<210> SEQ ID NO 20
<211> LENGTH: 23
<212> TYPE: DNA
<213> ORGANISM: Artificial sequence
<220> FEATURE:
<223> OTHER INFORMATION: synthetic

<400> SEQUENCE: 20
cgcgtcacga tatcgatatg acc                                                   23
```